(12) United States Patent
Harosh et al.

(10) Patent No.: US 9,481,709 B2
(45) Date of Patent: Nov. 1, 2016

(54) BOROPEPTIDE INHIBITORS OF ENTEROPEPTIDASE AND THEIR USES IN TREATMENT OF OBESITY, OVERWEIGHT AND/OR DISEASES ASSOCIATED WITH AN ABNORMAL FAT METABOLISM

(71) Applicant: OBE THERAPY BIOTECHNOLOGY, Evry (FR)

(72) Inventors: Itzik Harosh, Paris (FR); Sandrine Braud, Ieuville-sur-Orge (FR); Marco A. Ciufolini, Vancouver (CA)

(73) Assignee: OBE THERAPY BIOTECHNOLOGY, Evry (FR)

( * ) Notice: Subject to any disclaimer, the term of this patent is extended or adjusted under 35 U.S.C. 154(b) by 0 days.

(21) Appl. No.: 14/107,855

(22) Filed: Dec. 16, 2013

(65) Prior Publication Data

US 2014/0187479 A1    Jul. 3, 2014

Related U.S. Application Data

(62) Division of application No. 12/746,105, filed as application No. PCT/EP2008/066740 on Dec. 3, 2008, now abandoned.

(60) Provisional application No. 60/996,732, filed on Dec. 3, 2007.

(51) Int. Cl.

| | | |
|---|---|---|
| *C07D 345/00* | (2006.01) | |
| *C07D 517/00* | (2006.01) | |
| *C07K 5/08* | (2006.01) | |
| *C07K 5/062* | (2006.01) | |
| *C07K 5/065* | (2006.01) | |
| *C07K 5/072* | (2006.01) | |
| *C07K 5/083* | (2006.01) | |
| *C07K 5/087* | (2006.01) | |
| *C07K 5/09* | (2006.01) | |
| *A61K 38/05* | (2006.01) | |
| *A61K 38/06* | (2006.01) | |
| *C07K 5/06* | (2006.01) | |
| *A61K 38/00* | (2006.01) | |

(52) U.S. Cl.
CPC ............. *C07K 5/08* (2013.01); *A61K 38/005* (2013.01); *A61K 38/05* (2013.01); *A61K 38/06* (2013.01); *C07K 5/06* (2013.01); *C07K 5/0606* (2013.01); *C07K 5/06026* (2013.01); *C07K 5/06043* (2013.01); *C07K 5/06078* (2013.01); *C07K 5/06095* (2013.01); *C07K 5/06104* (2013.01); *C07K 5/06191* (2013.01); *C07K 5/0806* (2013.01); *C07K 5/0812* (2013.01); *C07K 5/0815* (2013.01); *C07K 5/0817* (2013.01); *C07K 5/0827* (2013.01); *A61K 38/00* (2013.01)

(58) Field of Classification Search
CPC .... A61K 38/00; A61K 38/005; A61K 38/05; A61K 38/06; C07K 5/06; C07K 5/06026; C07K 5/06043; C07K 5/0606; C07K 5/06078; C07K 5/06095; C07K 5/06104; C07K 5/08; C07K 5/0806; C07K 5/0812
See application file for complete search history.

(56) References Cited

U.S. PATENT DOCUMENTS

| | | |
|---|---|---|
| 3,867,539 A | 2/1975 | Henkin |
| 4,446,138 A | 5/1984 | Pack |
| 4,588,724 A | 5/1986 | Greenway, III et al. |
| 4,745,122 A | 5/1988 | Lassen |
| 5,019,594 A | 5/1991 | Wurtman et al. |
| 5,187,157 A | 2/1993 | Kettner et al. |
| 5,300,298 A | 4/1994 | LaNoue |
| 5,403,851 A | 4/1995 | D'Orlando et al. |
| 5,567,714 A | 10/1996 | Bruns, Jr. et al. |
| 5,573,774 A | 11/1996 | Keenan |
| 5,578,613 A | 11/1996 | Bryant et al. |
| 5,814,622 A | 9/1998 | de Nanteuil et al. |
| 5,900,411 A | 5/1999 | Morfeldt |
| 6,066,650 A | 5/2000 | Biller et al. |
| 6,121,283 A | 9/2000 | Chang et al. |
| 6,369,075 B1 | 4/2002 | Ruggeri et al. |

FOREIGN PATENT DOCUMENTS

| | | |
|---|---|---|
| EP | 0293881 A2 | 12/1988 |
| WO | 9509634 A1 | 4/1995 |
| WO | 2006050999 A2 | 5/2006 |

OTHER PUBLICATIONS

Of Kettner et al, The Journal of Biological Chemistry, vol. 265, No. 30, Issue of Oct. 25, pp. 18289-18297, 1990.*
Abe et al Regulatory Peptides 138 (2007) 56-58.*
Avellone et al, Diabetes Res. 1994; 25(2):85-92.*
Hadorn, B. et al., (1969) Intestinal enterokinase deficiency. Lancet 1(7599):812-813.
Holyoak, T. et al., (2003) 2.4 Å resolution crystal structure of the prototypical hormone-processing protease Kex2 in complex with an Ala-Lys-Arg boronic acid inhibitor. Biochemistry 42(22):6709-6718.

(Continued)

*Primary Examiner* — Jean Cornet
(74) *Attorney, Agent, or Firm* — Vorys, Sater, Seymour & Pease LLP

(57) ABSTRACT

Novel compounds, particularly derivatives of boroarginine, boroornithine and borolysine that selectively modulate, regulate, and/or inhibit enteropeptidase. Compositions, particularly pharmaceutical compositions, as well as methods to treat excess weight, obesity and diseases associated with an abnormal fat metabolism.

9 Claims, 25 Drawing Sheets

(56) References Cited

OTHER PUBLICATIONS

Imamura, T. And Kitamoto, Y. (2003) Expression of enteropeptidase in differentiated enterocytes, goblet cells, and the tumor cells in human duodenum. Am J Physiol Gastrointest Liver Physiol. 285(6):G1235-1241.

Katz, B. A, et al., (1995) Episelection: novel Ki approximately nanomolar inhibitors of serine proteases selected by binding or chemistry on an enzyme surface. Biochemistry 34(26):8264-8280.

Kettner, C. et al., (1990) The selective inhibition of thrombin by peptides of boroarginine. J Biol Chem 265 (30):18289-18297.

Komiyama, T. et al., (2005) Protection from anthrax toxin-mediated killing of macrophages by the combined effects of furin inhibitors and chloroquine. Antimicrob Agents Chemother 49(9):3875-3882.

Lebarbier, C. et al., (1998) Synthesis of boronic acid analogs of L-arginine as alternate substrates or inhibitors of nitric oxide synthase. Bioorg Med Chem Lett 8(18):2573-2576.

Lentze, M. J. (1982) Intestinal enteropeptidase deficiency associated with exocrine pancreatic insufficiency. Lancet 2 (8296):504.

Mann, N. S. and Mann, S. K. (1994) Enterokinase. Proc Soc Exp Biol Med 206(2):114-118.

Quan, M. L. et al., (1997) Biaryl substituted alkylboronate esters as thrombin inhibitors. Bioorg Med Chem Lett 7 (13):1595-1600.

Roberds, S. L. et al., (2001) BACE knockout mice are healthy despite lacking the primary beta-secretase activity in brain: implications for Alzheimer's disease therapeutics. Hum mol Genet 10(12):1317-1324.

Sharp, D. et al., (1993) Cloning and gene defects in microsomal triglyceride transfer protein associated with abetalipoproteinaemia. Nature 365(6441):65-69.

Stadnicki, A. et al., (1998) Specific inhibition of plasma kallikrein modulates chronic granulomatous intestinal and systemic inflammation in genetically susceptible rats. FASEB J 12(3):325-333.

Wetterau, J. R. et al., (1994) An MTP inhibitor that normalizes atherogenic lipoprotein levels in WHHL rabbits. Science 282(5389):751-754.

Yin, Z. et al., (2006) Peptide inhibitors of Dengue virus NS3 protease. Part 1: Warhead. Bioorg Med Chem Lett 16 (1):36-39.

* cited by examiner

| Enzyme | IC 50 (nM) | | | |
|---|---|---|---|---|
| | OBE 1999 | OBE 2000 | OBE 2001 | OBE 2002 |
| Enteropeptidase | 33.2 | 68 | 7.3 | 33.6 |
| Trypsin | 10.8 | 10.6 | 157 | 10.5 |
| Thrombin | 6400 | 3220 | 4000 | 4000 |
| Plasmin | 29.8 | 7100 | 21.7 | 3800 |
| Kallikrein | 7.5 | 260 | 6.9 | 81.4 |
| Chymotrypsin | No inhibition | No inhibition | No inhibition | No inhibition |
| Elastase | No inhibition | No inhibition | No inhibition | No inhibition |
| Carboxypeptidase A1 | No inhibition | No inhibition | No inhibition | No inhibition |
| Carboxypeptidase B1 | No inhibition | No inhibition | No inhibition | No inhibition |
| α-amylase | No inhibition | No inhibition | No inhibition | No inhibition |
| DPPIV | No inhibition | No inhibition | No inhibition | No inhibition |

Fig. 5

```
accagacagt tcttaaatta gcaagccttc aaaaccaaaa atg ggg tcg aaa aga    55
                                             Met Gly Ser Lys Arg
                                             1               5 ggc ata tct tct agg cat cat tct ctc agc tcc tat gaa atc atg ttt   103
Gly Ile Ser Ser Arg His His Ser Leu Ser Ser Tyr Glu Ile Met Phe
            10              15              20 gca gct ctc ttt gcc ata ttg gta gtg ctc tgt gct gga tta att gca   151
Ala Ala Leu Phe Ala Ile Leu Val Val Leu Cys Ala Gly Leu Ile Ala
        25              30              35 gta tcc tgc ctg aca atc aag gaa tcc caa cga ggt gca gca ctt gga   199
Val Ser Cys Leu Thr Ile Lys Glu Ser Gln Arg Gly Ala Ala Leu Gly
            40              45              50 cag agt cat gaa gcc aga gcg aca ttt aaa ata aca tcc gga gtt aca   247
Gln Ser His Glu Ala Arg Ala Thr Phe Lys Ile Thr Ser Gly Val Thr
        55              60              65 tat aat cct aat ttg caa gac aaa ctc tca gtg gat ttc aaa gtt ctt   295
Tyr Asn Pro Asn Leu Gln Asp Lys Leu Ser Val Asp Phe Lys Val Leu
70              75              80              85 gct ttt gac ctt cag caa atg ata gat gag atc ttt cta tca agc aat   343
Ala Phe Asp Leu Gln Gln Met Ile Asp Glu Ile Phe Leu Ser Ser Asn
            90              95              100 ctg aag aat gaa tat aag aac tca aga gtt tta caa ttt gaa aat ggc   391
Leu Lys Asn Glu Tyr Lys Asn Ser Arg Val Leu Gln Phe Glu Asn Gly
        105             110             115 agc att ata gtc gta ttt gac ctt ttc ttt gcc cag tgg gtg tca gat   439
Ser Ile Ile Val Val Phe Asp Leu Phe Phe Ala Gln Trp Val Ser Asp
            120             125             130 caa aat gta aaa gaa gaa ctg att caa ggc ctt gaa gca aat aaa tcc   487
Gln Asn Val Lys Glu Glu Leu Ile Gln Gly Leu Glu Ala Asn Lys Ser
        135             140             145 agc caa ctg gtc act ttc cat att gat ttg aac agc gtt gat atc cta   535
Ser Gln Leu Val Thr Phe His Ile Asp Leu Asn Ser Val Asp Ile Leu
150             155             160             165 gac aag cta aca acc acc agt cat ctg gca act cca gga aat gtc tca   583
Asp Lys Leu Thr Thr Thr Ser His Leu Ala Thr Pro Gly Asn Val Ser
            170             175             180 ata gag tgc ctg cct ggt tca agt cct tgt act gat gct cta acg tgt   631
Ile Glu Cys Leu Pro Gly Ser Ser Pro Cys Thr Asp Ala Leu Thr Cys
        185             190             195 ata aaa gct gat tta ttt tgt gat gga gaa gta aac tgt cca gat ggt   679
Ile Lys Ala Asp Leu Phe Cys Asp Gly Glu Val Asn Cys Pro Asp Gly
            200             205             210
```

Fig. 6A

```
tct gac gaa gac aat aaa atg tgt gcc aca gtt tgt gat gga aga ttt      727
Ser Asp Glu Asp Asn Lys Met Cys Ala Thr Val Cys Asp Gly Arg Phe
    215                 220                 225 ttg tta act gga tca tct ggg tct ttc cag gct act cat tat cca aaa      775
Leu Leu Thr Gly Ser Ser Gly Ser Phe Gln Ala Thr His Tyr Pro Lys
230                 235                 240                 245 cct tct gaa aca agt gtt gtc tgc cag tgg atc ata cgt gta aac caa      823
Pro Ser Glu Thr Ser Val Val Cys Gln Trp Ile Ile Arg Val Asn Gln
            250                 255                 260 gga ctt tcc att aaa ctg agc ttc gat gat ttt aat aca tat tat aca      871
Gly Leu Ser Ile Lys Leu Ser Phe Asp Asp Phe Asn Thr Tyr Tyr Thr
                265                 270                 275 gat ata tta gat att tat gaa ggt gta gga tca agc aag att tta aga      919
Asp Ile Leu Asp Ile Tyr Glu Gly Val Gly Ser Ser Lys Ile Leu Arg
            280                 285                 290 gct tct att tgg gaa act aat cct ggc aca ata aga att ttt tcc aac      967
Ala Ser Ile Trp Glu Thr Asn Pro Gly Thr Ile Arg Ile Phe Ser Asn
295                 300                 305 caa gtt act gcc acc ttt ctt ata gaa tct gat gaa agt gat tat gtt     1015
Gln Val Thr Ala Thr Phe Leu Ile Glu Ser Asp Glu Ser Asp Tyr Val
310                 315                 320                 325 ggc ttt aat gca aca tat act gca ttt aac agc agt gag ctt aat aat     1063
Gly Phe Asn Ala Thr Tyr Thr Ala Phe Asn Ser Ser Glu Leu Asn Asn
                330                 335                 340 tat gag aaa att aat tgt aac ttt gag gat ggc ttt tgt ttc tgg gtc     1111
Tyr Glu Lys Ile Asn Cys Asn Phe Glu Asp Gly Phe Cys Phe Trp Val
            345                 350                 355 cag gat cta aat gat gat aat gaa tgg gaa agg att cag gga agc acc     1159
Gln Asp Leu Asn Asp Asp Asn Glu Trp Glu Arg Ile Gln Gly Ser Thr
                360                 365                 370 ttt tct cct ttt act gga ccc aat ttt gac cac act ttt ggc aat gct     1207
Phe Ser Pro Phe Thr Gly Pro Asn Phe Asp His Thr Phe Gly Asn Ala
375                 380                 385 tca gga ttt tac att tct acc cca act gga cca ggg aga caa gaa         1255
Ser Gly Phe Tyr Ile Ser Thr Pro Thr Gly Pro Gly Gly Arg Gln Glu
390                 395                 400                 405 cga gtg ggg ctt tta agc ctc cct ttg gac ccc act ttg gag cca gct     1303
Arg Val Gly Leu Leu Ser Leu Pro Leu Asp Pro Thr Leu Glu Pro Ala
                410                 415                 420 tgc ctt agt ttc tgg tat cat atg tat ggt gaa aat gtc cat aaa tta     1351
Cys Leu Ser Phe Trp Tyr His Met Tyr Gly Glu Asn Val His Lys Leu
            425                 430                 435
```

Fig. 6B

```
agc att aat atc agc aat gac caa aat atg gag aag aca gtt ttc caa    1399
Ser Ile Asn Ile Ser Asn Asp Gln Asn Met Glu Lys Thr Val Phe Gln
        440             445                 450 aag gaa gga aat tat gga gac aat tgg aat tat gga caa gta acc cta    1447
Lys Glu Gly Asn Tyr Gly Asp Asn Trp Asn Tyr Gly Gln Val Thr Leu
    455                 460                 465 aat gaa aca gtt aaa ttt aag gtt gct ttt aat gct ttt aaa aac aag    1495
Asn Glu Thr Val Lys Phe Lys Val Ala Phe Asn Ala Phe Lys Asn Lys
470             475                 480                 485 atc ctg agt gat att gcg ttg gat gac att agc cta aca tat ggg att    1543
Ile Leu Ser Asp Ile Ala Leu Asp Asp Ile Ser Leu Thr Tyr Gly Ile
                490                 495                 500 tgc aat ggg agt ctt tat cca gaa cca act ttg gtg cca act cct cca    1591
Cys Asn Gly Ser Leu Tyr Pro Glu Pro Thr Leu Val Pro Thr Pro Pro
            505                 510                 515 cca gaa ctt cct acg gac tgt gga gga cct ttt gag ctg tgg gag cca    1639
Pro Glu Leu Pro Thr Asp Cys Gly Gly Pro Phe Glu Leu Trp Glu Pro
        520                 525                 530 aat aca aca ttc agt tct acg aac ttt cca aac agc tac cct aat ctg    1687
Asn Thr Thr Phe Ser Ser Thr Asn Phe Pro Asn Ser Tyr Pro Asn Leu
    535                 540                 545 gct ttc tgt gtt tgg att tta aat gca caa aaa gga aag aat ata caa    1735
Ala Phe Cys Val Trp Ile Leu Asn Ala Gln Lys Gly Lys Asn Ile Gln
550             555                 560                 565 ctt cat ttt caa gaa ttt gac tta gaa aat att aac gat gta gtt gaa    1783
Leu His Phe Gln Glu Phe Asp Leu Glu Asn Ile Asn Asp Val Val Glu
                570                 575                 580 ata aga gat ggt gaa gaa gct gat tcc ttg ctc tta gct gtg tac aca    1831
Ile Arg Asp Gly Glu Glu Ala Asp Ser Leu Leu Leu Ala Val Tyr Thr
            585                 590                 595 ggg cct ggc cca gta aag gat gtg ttc tct acc acc aac aga atg act    1879
Gly Pro Gly Pro Val Lys Asp Val Phe Ser Thr Thr Asn Arg Met Thr
        600                 605                 610 gtg ctt ctc atc act aac gat gtg ttg gca aga gga ggg ttt aaa gca    1927
Val Leu Leu Ile Thr Asn Asp Val Leu Ala Arg Gly Gly Phe Lys Ala
    615                 620                 625 aac ttt act act ggc tat cac ttg ggg att cca gag cca tgc aag gca    1975
Asn Phe Thr Thr Gly Tyr His Leu Gly Ile Pro Glu Pro Cys Lys Ala
630             635                 640                 645 gac cat ttt caa tgt aaa aat gga gag tgt gtt cca ctg gtg aat ctc    2023
Asp His Phe Gln Cys Lys Asn Gly Glu Cys Val Pro Leu Val Asn Leu
                650                 655                 660
```

Fig. 6C

```
tgt gac ggt cat ctg cac tgt gag gat ggc tca gat gaa gca gat tgt    2071
Cys Asp Gly His Leu His Cys Glu Asp Gly Ser Asp Glu Ala Asp Cys
            665                 670                 675 gtg cgt ttt ttc aat ggc aca acg aac aat ggt tta gtg cgg ttc        2119
Val Arg Phe Phe Asn Gly Thr Thr Asn Asn Asn Gly Leu Val Arg Phe
        680                 685                 690 aga atc cag agc ata tgg cat aca gct tgt gct gag aac tgg acc acc    2167
Arg Ile Gln Ser Ile Trp His Thr Ala Cys Ala Glu Asn Trp Thr Thr
    695                 700                 705 cag att tca aat gat gtt tgt caa ctg ctg gga cta ggg agt gga aac    2215
Gln Ile Ser Asn Asp Val Cys Gln Leu Leu Gly Leu Gly Ser Gly Asn
710                 715                 720                 725 tca tca aag cca atc ttc tct acc gat ggt gga cca ttt gtc aaa tta    2263
Ser Ser Lys Pro Ile Phe Ser Thr Asp Gly Gly Pro Phe Val Lys Leu
            730                 735                 740 aac aca gca cct gat ggc cac tta ata cta aca ccc agt caa cag tgt    2311
Asn Thr Ala Pro Asp Gly His Leu Ile Leu Thr Pro Ser Gln Gln Cys
        745                 750                 755 tta cag gat tcc ttg att cgg tta cag tgt aac cat aaa tct tgt gga    2359
Leu Gln Asp Ser Leu Ile Arg Leu Gln Cys Asn His Lys Ser Cys Gly
    760                 765                 770 aaa aaa ctg gca gct caa gac atc acc cca aag att gtt gga gga agt    2407
Lys Lys Leu Ala Ala Gln Asp Ile Thr Pro Lys Ile Val Gly Gly Ser
775                 780                 785 aat gcc aaa gaa ggg gcc tgg ccc tgg gtt gtg ggt ctg tat tat ggc    2455
Asn Ala Lys Glu Gly Ala Trp Pro Trp Val Val Gly Leu Tyr Tyr Gly
790                 795                 800                 805 ggc cga ctg ctc tgc ggc gca tct ctc gtc agc agt gac tgg ctg gtg    2503
Gly Arg Leu Leu Cys Gly Ala Ser Leu Val Ser Ser Asp Trp Leu Val
            810                 815                 820 tcc gcc gca cac tgc gtg tat ggg aga aac tta gag cca tcc aag tgg    2551
Ser Ala Ala His Cys Val Tyr Gly Arg Asn Leu Glu Pro Ser Lys Trp
        825                 830                 835 aca gca atc cta ggc ctg cat atg aaa tca aat ctg acc tct cct caa    2599
Thr Ala Ile Leu Gly Leu His Met Lys Ser Asn Leu Thr Ser Pro Gln
    840                 845                 850 aca gtc cct cga tta ata gat gaa att gtc ata aac cct cat tac aat    2647
Thr Val Pro Arg Leu Ile Asp Glu Ile Val Ile Asn Pro His Tyr Asn
855                 860                 865 agg cga aga aag gac aac gac att gcc atg atg cat ctg gaa ttt aaa    2695
Arg Arg Arg Lys Asp Asn Asp Ile Ala Met Met His Leu Glu Phe Lys
870                 875                 880                 885
```

Fig. 6D

```
gtg aat tac aca gat tac ata caa cct att tgt tta ccg gaa gaa aat       2743
Val Asn Tyr Thr Asp Tyr Ile Gln Pro Ile Cys Leu Pro Glu Glu Asn
            890                 895                 900 caa gtt ttt cct cca gga aga aat tgt tct att gct ggt tgg ggg acg       2791
Gln Val Phe Pro Pro Gly Arg Asn Cys Ser Ile Ala Gly Trp Gly Thr
        905                 910                 915 gtt gta tat caa ggt act act gca aac ata ttg caa gaa gct gat gtt       2839
Val Val Tyr Gln Gly Thr Thr Ala Asn Ile Leu Gln Glu Ala Asp Val
        920                 925                 930 cct ctt cta tca aat gag aga tgc caa cag cag atg cca gaa tat aac       2887
Pro Leu Leu Ser Asn Glu Arg Cys Gln Gln Gln Met Pro Glu Tyr Asn
    935                 940                 945 att act gaa aat atg ata tgt gca ggc tat gaa gaa gga gga ata gat       2935
Ile Thr Glu Asn Met Ile Cys Ala Gly Tyr Glu Glu Gly Gly Ile Asp
950                 955                 960                 965 tct tgt cag ggg gat tca gga gga cca tta atg tgc caa gaa aac aac       2983
Ser Cys Gln Gly Asp Ser Gly Gly Pro Leu Met Cys Gln Glu Asn Asn
                970                 975                 980 agg tgg ttc ctt gct ggt gtg acc tca ttt gga tac aag tgt gcc ctg       3031
Arg Trp Phe Leu Ala Gly Val Thr Ser Phe Gly Tyr Lys Cys Ala Leu
            985                 990                 995 cct aat cgc ccc gga gtg tat gcc agg gtc tca agg ttt acc gaa           3076
Pro Asn Arg Pro Gly Val Tyr Ala Arg Val Ser Arg Phe Thr Glu
        1000                1005                1010 tgg ata caa agt ttt cta cat tag cgcatttctt aaactaaaca ggaaagtcgc      3130
Trp Ile Gln Ser Phe Leu His
            1015 attattttcc cattctactc tagaaagcat ggaaattaag tgtttcgtac aaaaatttta     3190
aaaagttacc aaaggttttt attcttacct atgtcaatga atgctaggg ggccagggaa      3250
acaaaatttt aaaaataata aaattcacca tagcaataca gaataacttt aaaataccat    3310
taaatacatt tgtatttcat tgtgaacagg tatttcttca cagatctcat ttttaaaatt    3370
cttaatgatt attttattta cttactgttg tttaaaggga tgttatttta aagcatatac    3430
catacactta agaaatttga gcagaattta aaaagaaag aaaataaatt gttttcccca     3490
aagtatgtca ctgttggaaa taaactgcca taaattttct agttccagtt tagtttgctg    3550
ctattagcag aaactcaatt gtttctctgt cttttctatc aaaatttttca acatatgcat   3610
aaccttagta ttttcccaac caatagaaac tatttattgt aagcttatgt cacaggcctg    3670
gactaaattg attttacgtt cctctt                                          3696
```

Fig. 6E

Step 1:
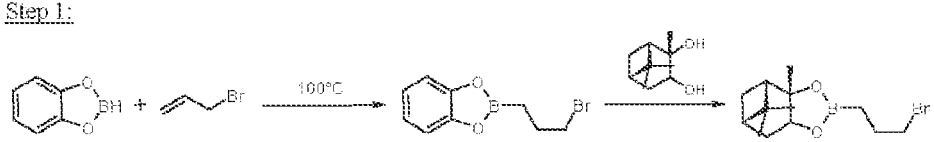
Step 2:
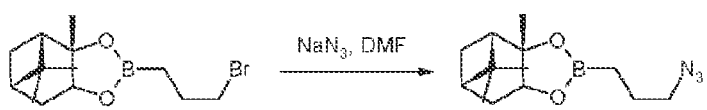
Step 3:
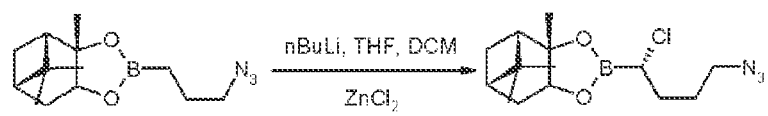
Step 4:
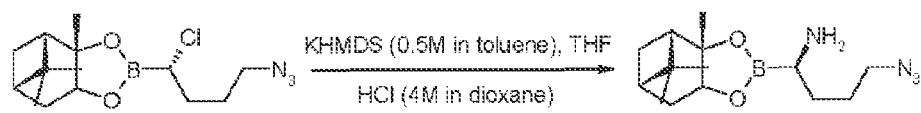
Step 5:
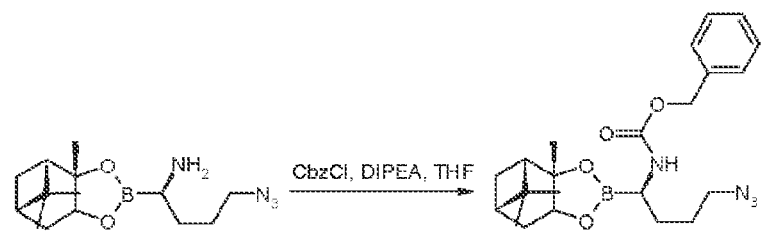
Step 6:
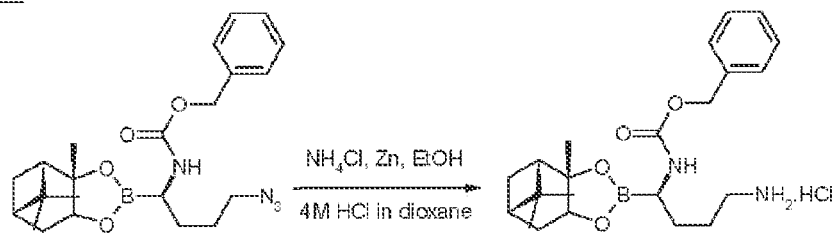
Step 7:
Fig. 7B Step 8:
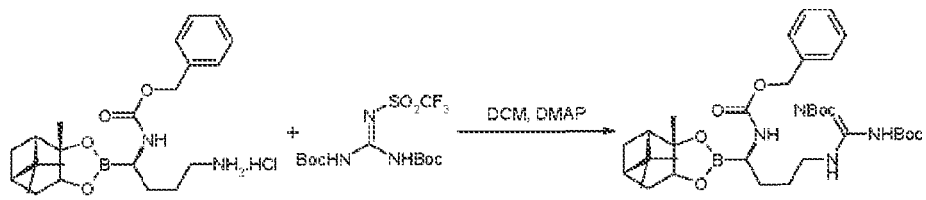
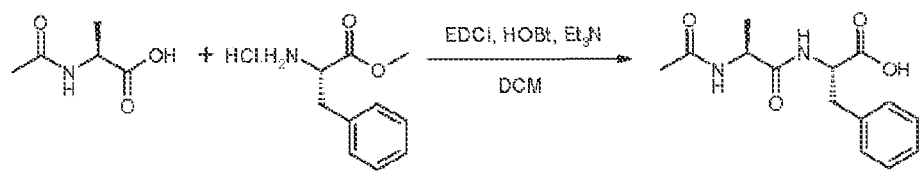
Step 9:
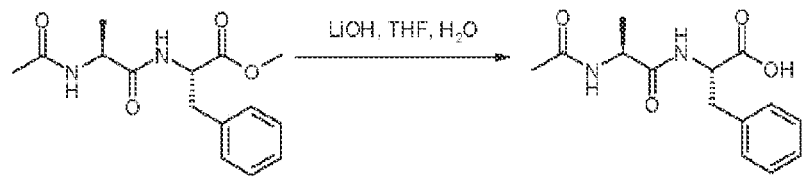
Step 10:
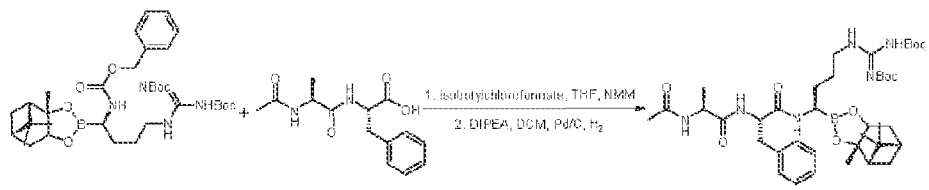
Step 11:
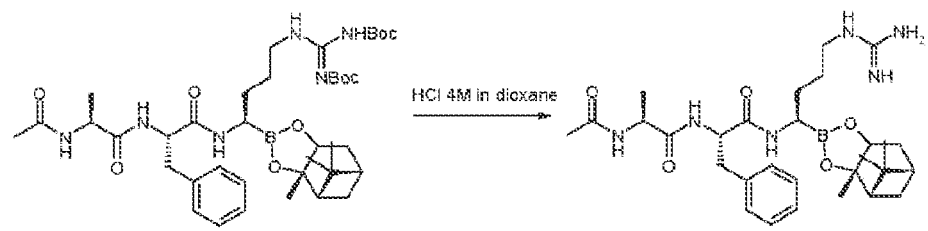
Fig. 7C

```
cggccgccctgtcagttgccgggatgagcttaagtcctttgtccatcattcttagatcc
tcccttttcctttcttccaggaaagcaaggagacacttcatcaaagactccactccatt
atcatctgagtgccttgcagaaagtttaaattccaatctggtacacatggcgggttctct
cattccataccatttccaaaataactctccttcccttaactagtagaacattttttagtg
aatgattaagcacaattgaggccacatggatatcttaactacttttcttaccatttaaaa
tccttcctcttcataaactttgcctgacttactttctcttcatgctggatatacctggt
aacattatgttgatcttattgattagaaggaatatccatagaatgtgtaatttggaattt
tatttatcaccacaacactcaaattgatatgaagcaagtgttttgcatcataatgctca
aggctttagaagtagatcttttgtctttaaagagttctgcaaatcgacaggatggtgga
atgttgcaaaggtgtatctgtgagtgggggccaaaagctattaggggttgaactgtggga
accttgggcccacataaggactaaacataggggctgtggatagaccaagtgaaagatta
tttccaggaaacgaaggcaaagaaatgcagatcttgacatttgatcttggggatacttac
aggcacttttaccgtagccagaacaatgactactatgggaaagaacaaactgaatcccag
gcacaatcccataagggcctaggtctcgttctagggaatggaacttacatgtcagaccta
tcttggaggaagaactcacaagcccccgagtccgtgaatgtgcatctgccttggacatac
attgattcgagagagaggcacaatgaacctttcagtacacaaaggacttaaatccagttt
aggaagactaaaggaaaaaaaaaacaatagatggttacttgcacctaggactggagcat
gtgtttgggaacgattggacactaattgtatcaacaattatatcagagtgcccataaagc
gagattcagaaacctggccaaagaaaacaaggtttattgggggagggggaatgggaggt
tttagtactctgctgggcactgttgcacatgcgtgtttgagctctatggttagtgaaaag
atacaaatatgcaaatatgcttgtctgttctcaacacttataagaactgtttgccatttt
tacatcttggaataatctagacttttttttgtaggaatggaaagtattctcaggaggga
agaagaactcataatatctgtctgactgtctccatttggaccgagacacatttagtttga
tacgactcaagaactgaatttatttcttcttatgttttttttccagtaaaggaagatcaa
aaactagcccgaatcagtctacactgtggatttcaaaaagcacgaggaaggaaagtggca
tggaggtataataatgaactggcattgttctggaaaaataaaatagttttgtaatcgttg
atcaatgtaaggaatggcatcatcaccttggaatggcttgaaatctcaaaggatctgcaa
gatggactgtaagctcccccttgaggcaaatgtcaaaataattttttagaagtttatagtt
tcacttacaacatatgctgagtgagacctggttactctcctaaaggatacacctaaattt
catgtaaaagaaatggaccatgcggatataatttctgtggaccaatctggaatacctgtg
ttgggagtagttactcttgctctctttcttttttcatcttcataaattttgatctatgtc
atgtaatataaattgtatttcaatttacggtgtgcagaaacattctacctttgcaaaagt
gtttgatgaaaatagagtgttctgatatttatatttatgacatttgattttttacatatat
agtgttttcattaaaaactgaattcacacagacacaaagaaatccttgcatagggaaaac
atttctttggtaggatagttcatgtttgttctgtttctttgctttgggttcgataaagtt
taggaagtatcttcagaaataagaaactatttcattgactgtgctgttaatctgctgaaa
cactttacttagaggcaagaactgtctaacttcaattgtgcaagacacgtgccttacaat
tattcttaatttaaaattaaacagattttttgtaataaagtatctttaataatacttgtat
agacaccaatagagttaaccttgaaaaaaatggcatctgcagtacaaatcacaggtcttc
acatgttgcctatagaattgcaaatagctcccagagtgtcaggaatcaatgtggctcct
cccttcaatcaaacagagtaactatttgaaggctttggagtcagacagttgctgtttgg
ctgaggttctcctaactgaatttagcctgtataatatataaagctcaatggtttccagca
gtgtgatgctaagcagaacacactgatattaatgattaaagaagaagaagaagaaaaac
aaaactacaaatcacatcatttaatgggccagggactcgaggttgctgatgtttgcttat
ctttgatgagtgttgtttgtggttgtgaactgtggcttccttctgtctgatggagtttcc
tcaacacgtagcacttgttcttctcaagagagttgtaactattttgtcttcaaatgtccc
tgtgtcacttttagccaaataaagagttcttgtttctgaagaatgatctttggtgttgtc
tacattcttaagggaccaaggcccagatgtgtttcatcattacctgaggatgaaatcaaa
cattgcatgtgaagagcccagacagcggcagatctgaaggaacagggatgtttcttcttt
ctctgtcagtcttgttcagttagacagtccttaagtagacttggttttccaaacaagag
gcaaaaatgggctctcagatcttttcctgctgccttgagactgaatggacaactgcattc
taagctcagctgcccccacttagctccatccttttgggtcaaatgggaggccagctgttt
ggatctatgttttgcctgtatgccaactccactcgtttctccatttagctatccagaact
ctaacagctgaaggatggaagcacaaactgaaggggaaggctggtgtttcttttattat
caaggtcaggaaagcatccagtgttaatggcaaactccatctgtgacaagggtgggaaaa
caattctctgtcctcttaaagatggtgatgataccatctttgaaagggtttgtaaagt
tttagctggcccttgcaaaaccggtacatgatgtaactgctctgtattttcagaacata
```

Fig. 12B

```
gtgttaatatatgttgggaaatgatccattcaagtattcacaaacaaaccacacactcgc
ttcttcttcttattttcccttctaggttgaggttattggcaaggttttcctgagaagagt
gtgcagagacctttgattattagtgtcagtgcttgtgggaacatgcagtcccctatcatc
tgggcgaatcttcttttattgaaatgttttccatgctctgactgtcttcagttagaacat
gattgtctcgaaacctctgtcctccattttcagggtcactgtcacctgtagagttgtctc
tagtgtctcttaaacgcatcgaattgtaattatcccatctaaagcatagctcaagctttc
tcccttccccaaagcaaatattagcagttgcttttttaaaaaaaattttttaaatacaact
catttgaaccctattcattcttgcattggattaattcatgaaagaaaaatgaaaacaatg
aatgtgtttatgttgatgaaatatgtctgtgtcagtgttagtgtgtgtgtgtgtgtgtgt
gtgtgtgtgtgtgtgtgtgtatgtatttgtgtcaagttagcatggatttcagcagattct
gtgtgataaactgaactgacatttgcattttctctggaaataatccaagagattaaagaa
gtggagcaaattaatttattacacattttttgcctttagtggggaattcagctgtgtctg
aacaaattttttcacatgttcaggatagtctctaaactgtacaattttcgcggctcgagc
ctaggggtaaccgaagttcctatacttttctagagaataggaacttcggaataggaacttc
ttataatctagaactagtggatcgatccacgattcgagggcccctgcaggtcaattctac
cgggtaggggaggcgcttttcccaaggcagtctggagcatgcgctttagcagcccgctg
ggcacttggcgctacacaagtggcctctggcctcgcacacattccacatccaccggtagg
cgccaaccggctccgttctttggtggccccttcgcgccaccttctactcctcccctagtc
aggaagttccccccccgccccgcagctcgcgtcgtgcaggacgtgacaaatggaagtagca
cgtctcactagtctcgtgcagatggacagcaccgctgagcaatggaagcgggtaggcctt
tggggcagcggccaatagcagctttgctccttcgctttctgggctcagaggctgggaagg
ggtgggtccggggcgggctcaggggcgggctcaggggcggggcgggcgcccgaaggtcc
tccggaggccccggcattctgcacgcttcaaaagcgcacgtctgccgcgctgttctcctct
tcctcatctccgggcctttcgacctgcagccaatatgggatcggccattgaacaagatgg
attgcacgcaggttctccggccgcttgggtggagaggctattcggctatgactgggcaca
acagacaatcggctgctctgatgccgccgtgttccggctgtcagcgcaggggcgcccggt
tcttttttgtcaagaccgacctgtccggtgccctgaatgaactgcaggacgaggcagcgcg
gctatcgtggctggccacgacgggcgttccttgcgcagctgtgctcgacgttgtcactga
agcgggaagggactggctgctattgggcgaagtgccggggcaggatctcctgtcatctca
ccttgctcctgccgagaaagtatccatcatggctgatgcaatgcggcggctgcatacgct
tgatccggctacctgcccattcgaccaccaagcgaaacatcgcatcgagcgagcacgtac
tcggatggaagccggtcttgtcgatcaggatgatctggacgaagagcatcaggggctcgc
gccagccgaactgttcgccaggctcaaggcgcgcatgcccgacggcgaggatctcgtcgt
gacccatggcgatgcctgcttgccgaatatcatggtggaaaatggccgcttttctggatt
catcgactgtggccggctgggtgtggcggaccgctatcaggacatagcgttggctacccg
tgatattgctgaagagcttggcggcgaatgggctgaccgcttcctcgtgctttacggtat
cgccgctcccgattcgcagcgcatcgccttctatcgccttcttgacgagttcttctgagg
ggatcgatccgctgtaagtctgcagaaattgatgatctattaaacaataaagatgtccac
taaaatggaagttttcctgtcatactttgttaagaagggtgagaacagagtacctacat
tttgaatggaaggattggagctacggggtggggtggggtggattagataaatgcctg
ctctttactgaaggctctttactattgctttatgataatgtttcatagttggatatcata
atttaaacaagcaaaaccaaattaagggccagctcattcctcccactcatgatctataga
tctatagatctctcgtgggatcattgtttttctcttgattcccactttgtggttctaagt
actgtggtttccaaatgtgtcagtttcatagcctgaagaacgagatcagcagcctctgtt
ccacatacacttcattctcagtattgttttgccaagttctaattccatcagaagctgact
ctagatcctgcaggaattaattcatatgaagttcctatactttctagagaataggaactt
cggaataggaacttcaaaatgtcgcggcgcgccatgtcttgtggttcctgaagactgtg
agaaatgtttgcttttgattacttttatcacgaattattttgatttcagcaaacatggat
ttcactactttctcattcctagggaatatgtttcaattactctagtctatatctaaaacc
acttacagtgctaaacctgtgttcaacatggtctctttcaatcaagtacttgtgacaca
tcacggttgtaaatctgaattttgggcttaggtgatggatagtaacgcaaattgattat
ttttcttctctacttttttttttcttttggtgaatagataacacatgctaatgccaggct
gtaatttttaagcaatattagcatatgacttttcttttctctccttactaagtagaaaact
tttacttaaagaaacagtctttctgtagtctggtactactcttgggcaaagcatggctta
cgtggagaaaagaactgaacgctgcaagtaatcttgggaattaaattaatttctgaagga
tcagcggaaaggtaacgcatgctttgttcttgccacaacaagagatggttcactccggac
tcagtgagattgcctagtgctcccgagattggtaataactgaagctaatgaactgctaat
```

Fig. 12C

```
gtatggatttacccttttaatacttttagactatgattggccatttggtgacagacgtagt
agaaacaaactgtaagaaaaagatgaactgatgaagacccgcttccagtctcatctactt
cagggctgttcagtgacaagcccttctatgaggctgtgaaattcattctggaaagcaaat
gggcttacgctggtaaaagaggcagacatgtgcgtagcgactataaaataacgactacgc
gtaaactactgaaatcacatcgcctatagttttgaaatttggttttttccaaagccaggaa
aacttacattaaaaaataaaattgtttacgaggttttatacaatttgaccagcagagggc
aatgttacaccaggaatcataacactgccactattctgcctctgcggatatcccacacat
taaatatttgtatatgtgtgcccacacatagaattaaatgctctacacttatgtacttac
ttaaatgacgtgtgcatgttgcttgagtactcttactttggaaaaaggataaaagaaaaa
aaaaaaacacaaaacaaagctatgtgctcactaaaagcaactccatagttttagaacacg
aatggtaaagcttatttaaaaagaacgtacgacattctattatcaacattctcttttaat
atataagacaacttcaatagaaatataagaaaatgtactttgtgaatgatcagtatttct
atatacctctctataaaatgcctcgaaaatctcaattaatttcccttttgatgctcacgt
gtgtttgaaagaaaagtaggctacaggatgcattgtaggatactttcaagtctcacaaat
gcgcttttcaaatctacagtgctcattaataaaaatccatattcagaatggctcctggga
cagtgttactggccttagaaagggcaaacagtgcttaaatattttaatcaagcacataa
gcagttaatagctcattgccatctcacaagaaatttcacattttctccgataacttcttc
cttattttgttacagcttttagaagaaggatacccctccaaagcactattttttccatctt
acactaaatgccacaattatataacattaattaactaagggactgaataaaatcaatatgt
ctcaattttgcctgctcagtataataggggccaattaaagaaaggattgaagacatttagc
taactggcttttttggtgtaaatgagcataaaggtacatctatataaagtctttcttttt
ttcaactaccatgaatataagtataatcgtggcactaatatattgttgaaactgtcacctg
actcctacaactttgtagcagatgctcagctgggtcttcatgtgggtccctgacaattg
tagcaggcactgtctctgaatctattgcctgaacctggatccccttcctctagctgaact
gccttgttgggcctcagtggaaggggtgcacttagtcctgcaacagtttgatctgcttgg
gcaggttggtacccggatgtgtgtgaggccttcctatctcaggagggatagttggggagg
ggctggggaggatgagcctgggaggagaggagggagggtgctgcaatcagggatgtaaag
tgaataaataaattaagaaaaaagaaaaaaaaggaaataatacggttttctctgaaaga
ggcattcaattaatttgaatggctttaaactttgttttctctttcttactaatatttaca
tctaggaaacctgaataggtagaattctcagcataccggagaaccatgggctctcagaac
gccttattagaaaggaagttgtgaaacctgtgtgaaaactttcaggtggattggctcaaa
cccactgggatcgctatctgtcaacactgacagacagtgctaaaccccaagattctctcg
cagatactaaatgtagagcttacaaatttgttttattgcttgagctttggggagtgctga
ctttcctgagcagtggaataagctgatgctgttttaacgtcaagtctgttaagtaaagtg
tactggtaacaggatgctaactgttaagagtgcaattctgatgtctctttgcagtcattt
ctcatcccgagtttatctgtagtgggaatatgagattcagaggccaatttcctcagtctc
aaacaaaaatcactactaatgtctaaataggagaaattacataatatactatgacagaat
ttttgaatagaggaaggatgctgatttttaatacttcacaaaaaagggtataagagaaga
tctagcttaaaatagcaaaaaaagatacaatataggactaattatattattttttaaatt
atattcatatttgtttgctaagaaagataaccccttgattctcacgtaaccccttgtctt
ttgatggttgtctgaggcgtatttatcctatttattctaaaacttacaatttatttcat
gatatttagagctttagagtatgagactaagaacagtattatggtatatcatcttcctct
ctgtatgtcataacagcaatggcttaaaacagtaaattagactgtcttatacaaatgaag
atcaaacaatcctatcaggaaaaaacaaacccatatgtttgttgacattacacaaataaa
agccaggcagtggtggcacatacctttaatcccagcacttgggaggcagaggcaggcgga
tttctgagtttgagaccagcctggtctacagagtgagttccaggacagccagggctacac
agagaaaccctgtctcaaaacaaacaaaaagcaagcaagcaagcaagcaagcaagcaacc
aacaagcaaaagaaattgaaaaaaatttcaaatgtatgtggtcaatgtgtggtggcact
gacacattaatggctctctctctctctctctctctctctctctctctctctctctatatata
tatatatatatatatatatatatatatatatatatatatatatatatatatatatatatt
cctatgtaccaaataaaataaaacatcctggcacccacctaggagttagtatcaagctt
ccattaggggcttggtttactctcacaaatggtccacctccggtagatgatattggcatt
gatgagtttgcactcctaaggtagaataaacgacatatgaacaggagataaaattaccaa
cattaatgctacattttcattattggatgagacataattggaagtaaattatgttaatac
ttgggaaaagtggagggcagagaaactgggcaggatctattgtataagggaagaatccat
tttcaatagatataatatcaaacaatattatagaccgttagcaaaattattacttaggac
attaaatattgtcagttttttgggaaagcctttagtacacgtttgaatatcgtacattata
```

Fig. 12D

```
ttacaaggtcgctacacatttctctcgaggatctgatttctgttctgttctgttttcccc
ttttcaatgctgttgagaggatgtgaatagtttaatggatcagctcatataaaatttgaa
ttaagtttgaatgagaaaaataaatacaccgattataatttaagcctttctttaaggagg
tataactcatctttcaagaaaatcaaatcgcctaagaactacacagagtagttctagctt
tagtagttcggagtttagctttctagttttttttttgcttttgttatctcattaaattta
aagtcaaagcagtcccaaatccaaggacgaagacaagcggttgctccgagggcctccata
acctccatctgcagttgccaactggtgagccaccgcagggtgacaaaagacacctccatg
taacacagcatccaatcctctaggctacaacctgtggcatctgcaccatctgctgtgagg
cttagtgaaggtttctcttaattaattttactttttattttaaaatttaactaaatttagt
taaattaaaatctgacccttttaaaataattcttttactcaatcaatatcttagtatta
ataaaaactatgcctttaaatgtgaaagtcagtgggctgaacctgcaaaggggaaaagt
gatggttaaaagtgatacaatatgcatgtgggaaatcgtcagcagttaaatcaccatcac
catcaccatcatcatcaccatcaccatcaccatcatcaccatcaccatcaccaccctcac
cctcaccctcaccctcacactcaccctcaccctcaccctcaccatcatcattaccatcac
cacgtttgcctctggattctaggtatattaattttactgttctctatggttgttaggaga
caatgtaacctctagctactgaaataacaagttgagtgtgcttgttgcctctccagaata
tttaatgtctctcctggatgatagcaaacaataacaatgtgtttaggtgcacgggaaatg
gaccaggagcacccaaaattcttatgagcagtgaaaagaaaaaacaaatgttcaagaggt
agttcctctcctttccaaagccttcgtcagacttagcctttatttgctgccttccagcca
ctgaacattatgttgggaaaatagatgctctgtctaatgtcccaatatttggtatatttc
acttccacttgataagcaaacaaatgcaatgaaagaacacaaagccattaatcttcctt
aacaaaatatcaaatagattttccgaatcaaagagaagtcttgctgttgttatttttgga
tttgatactatcttctccaaccacatgagcagaagagttatttcatttaaatagctctat
gcaatgtatttgctgaagcttaggggaaaaaaggggggggcagaagtggatgtagaag
cttagggatgcttgagtcatagaaacttctaccgatataaactagtcacaggtgaagaac
cacacatttttgtgagagcaaatgtagatcaaggcctctatgttttatcagggtgtggc
ttctggtagatcgcatcaacgcacccaggtaaagtatcaggcctcctgaatgttggcttc
aggcttcagttctggaattggttagtgcacctgcatgccgggggcgcggggtggggtggg
gtaaagtccacagtgatgattactctctaatctctcttcagacagcgttcttctcttgtt
tactcgagttacagttccttattctgcctacggtttgcagccttggagcacttttctacg
tagctctctaagtctcttatctttcaggagacattgtcacagtgctctgtcaacagtagc
ggcggtcgctccagaagattaaaaattaaaacgataaactacccagagccacttagatc
aaatgggattggaaagtcaggttgcccatccagcgtgctacagtaagaaaccttcaaat
gatcctaatatttgctatagaaaaggaaacgaggtcgggccggccaagcttaaggaattc
gctagcatgcatgttaacggatccttaattaatgtacagggtcccgtttaaacagtaacg
ctagggataacagggtaatataatcgagctgcaggattcgagggccccggcaggtcaatt
ctaccgggtaggggaggcgcttttcccaaggcagtctggagcatgcgctttagcagcccc
gctgggcacttggcgctacacaagtggcctctggcctcgcacacattccacatccaccgg
taggcgccaaccggctccgttctttggtggccccttcgcgccaccttctactcctcccct
agtcaggaagttccccccgcccgcagctcgcgtcgtgcaggacgtgacaaatggaagt
agcacgtctcactagtctcgtgcagatggacagcaccgctgagcaatggaagcgggtagg
ccttgggcagcggccaatagcagctttgctccttcgctttctgggctcagaggctggg
aaggggtgggtcgggggcgggctcaggggcgggctcaggggcggggcgggcgccgaag
gtcctccggaggccggcattctgcacgcttcaaaagcgcacgtctgccgcgctgttctc
ctcttcctcatctcgggcctttcgacctgcagccaatgcaccgtccttgccatcatggc
ctcgtaccccggccatcaacacgcgtctgcgttcgaccaggctgcgcgttctcgcggcca
tagcaaccgacgtacggcgttgcgcctcgccggcagcaagaagccacggaagtccgccc
ggagcagaaaatgccacgctactgcgggtttatatagacggtccccacgggatggggaa
aaccaccaccacgcaactgctggtggccctgggttcgcgcgacgatatcgtctacgtacc
cgagccgatgacttactggcgggtgctgggggcttccgagacaatcgcgaacatctacac
cacacaacacgcctcgaccagggtgagatatcggccgggacgcggcggtggtaatgac
aagcgcccagataacaatgggcatgccttatgccgtgaccgacgccgttctggctcctca
tatcgggggggaggctgggagctcacatgccccgccccggccctcaccctcatcttcga
ccgccatcccatcgccgccctcctgtgctaccggccgcgcggtaccttatgggcagcat
gacccccaggccgtgctggcgttcgtggccctcatcccgccgaccttgccggcaccaa
catcgtgcttggggcccttccggaggacagacacatcgaccgcctggccaaacgccagcg
cccccggcgagcggctggacctggctatgctggctgcgattcgccgcgtttacgggctact
```

Fig. 12E

```
tgccaatacggtgcggtatctgcagtgcggcgggtcgtggcgggaggactggggacagct
ttcggggacggccgtgccgcccaggggtgccgagcccagagcaacgcgggcccacgacc
ccatatcggggacacgttatttaccctgtttcgggccccgagttgctggccccaacgg
cgacctgtataacgtgtttgctgggccttggacgtcttggccaaacgcctccgttccat
gcacgtctttatcctggattacgaccaatcgccgccggctgccgggacgccctgctgca
acttaccctcgggatggtccagaccacgtcaccaccccggctccataccgacgatatg
cgacctggcgcgcacgtttgcccgggagatgggggaggctaactgaggggatcgatccgt
cctgtaagtctgcagaaattgatgatctattaaacaataaagatgtccactaaaatggaa
gttttcctgtcatactttgttaagaagggtgagaacagagtacctacattttgaatgga
aggattggagctacggggtgggggtgggggtgggattagataaatgcctgctctttactg
aaggctctttactattgctttatgataatgtttcatagttggatatcataatttaaacaa
gcaaaaccaaattaagggccagctcattcctcccactcatgatctatagatctatagatc
tctcgtgggatcattgttttctcttgattcccactttgtggttctaagtactgtggttt
ccaaatgtgtcagtttcatagcctgaagaacgagatcagcagcctctgttccacatacac
ttcattctcagtattgttttgccaagttctaattccatcagaagctgactctaggccgga
cgcccggggcgaccggcgagctccaattcgccctatagtgagtcgtattacaattcactg
gccgtcgttttacaacgtcgtgactgggaaaaccctggcgttacccaacttaatcgcctt
gcagcacatccccttcgccagctggcgtaatagcgaagaggcccgcaccgatcgcct
tcccaacagttgcgcagcctgaatgcgaatgggacgcgcctgtagcggcgcattaagc
gcggcgggtgtggtggttacgcgcagcgtgaccgctacacttgccagcgccctagcgccc
gctcctttcgctttcttcccttcctttctcgccacgttcgccggctttccccgtcaagct
ctaaatcggggggctcccttagggttccgatttagtgctttacggcacctcgaccccaaa
aaacttgattagggtgatggttcacgtagtgggccatcgccctgatagacggttttcgc
cctttgacgttggagtccacgttctttaatagtggactcttgttccaaactggaacaaca
ctcaaccctatctcggtctattcttttgatttataagggattttgccgatttcggcctat
tggttaaaaaatgagctgatttaacaaaaatttaacgcgaattttaacaaaatattaacg
cttacaatttaggtggcacttttcggggaaatgtgcgcggaacccctatttgtttatttt
tctaaatacattcaaatatgtatccgctcatgagacaataaccctgataaatgcttcaat
aatattgaaaaaggaagagtatgagtattcaacatttccgtgtcgcccttattccctttt
ttgcggcattttgccttcctgttttgctcacccagaaacgctggtgaaagtaaaagatg
ctgaagatcagttgggtgcacgagtgggttacatcgaactggatctcaacagcggtaaga
tccttgagagttttcgccccgaagaacgttttccaatgatgagcacttttaaagttctgc
tatgtggcgcggtattatcccgtattgacgccgggcaagagcaactcggtcgccgcatac
actattctcagaatgacttggttgagtactcaccagtcacagaaaagcatcttacggatg
gcatgacagtaagagaattatgcagtgctgccataaccatgagtgataacactgcggcca
acttacttctgacaacgatcggaggaccgaaggagctaaccgcttttttgcacaacatgg
gggatcatgtaactcgccttgatcgttgggaaccggagctgaatgaagccataccaaacg
acgagcgtgacaccacgatgcctgtagcaatggcaacaacgttgcgcaaactattaactg
gcgaactacttactctagcttcccggcaacaattaatagactggatggaggcggataaag
ttgcaggaccacttctgcgctcggcccttccggctggctggtttattgctgataaatctg
gagccggtgagcgtgggtctcgcggtatcattgcagcactggggccagatggtaagccct
cccgtatcgtagttatctacacgacggggagtcaggcaactatggatgaacgaaatagac
agatcgctgagataggtgcctcactgattaagcattggtaactgtcagaccaagtttact
catatatactttagattgatttaaaacttcattttaatttaaaaggatctaggtgaaga
tcctttttgataatctcatgaccaaaatcccttaacgtgagttttcgttccactgagcgt
cagaccccgtagaaaagatcaaaggatcttcttgagatccttttttctgcgcgtaatct
gctgcttgcaaacaaaaaaaccaccgctaccagcggtggtttgtttgccggatcaagagc
taccaactctttttccgaaggtaactggcttcagcagagcgcagataccaaatactgtcc
ttctagtgtagccgtagttaggccaccacttcaagaactctgtagcaccgcctacatacc
tcgctctgctaatcctgttaccagtggctgctgccagtggcgataagtcgtgtcttaccg
ggttggactcaagacgatagttaccggataaggcgcagcggtcgggctgaacggggggtt
cgtgcacacagcccagcttggagcgaacgacctacaccgaactgagatacctacagcgtg
agctatgagaaagcgccacgcttcccgaagggagaaaggcggacaggtatccggtaagcg
gcagggtcggaacaggagagcgcacgagggagcttccaggggaaacgcctggtatcttt
atagtcctgtcgggtttcgccacctctgacttgagcgtcgatttttgtgatgctcgtcag
ggggcggagcctatggaaaaacgccagcaacgcggcctttttacggttcctggccttt
gctggccttttgctcacatgttctttcctgcgttatcccctgattctgtggataaccgta
```

Fig. 12F

```
ttaccgcctttgagtgagctgataccgctcgccgcagccgaacgaccgagcgcagcgagt
cagtgagcgaggaagcggaagagcgcccaatacgcaaaccgcctctccccgcgcgttggc
cgattcattaatgcagctggcacgacaggtttcccgactggaaagcgggcagtgagcgca
acgcaattaatgtgagttagctcactcattaggcaccccaggctttacactttatgcttc
cggctcgtatgttgtgtggaattgtgagcggataacaatttcacacaggaaacagctatg
accatgattacgccaagctcgaaattaaccctcactaaagggaacaaaagctgtcgagat
ctagatatcgatggccatag
```

Fig. 12G

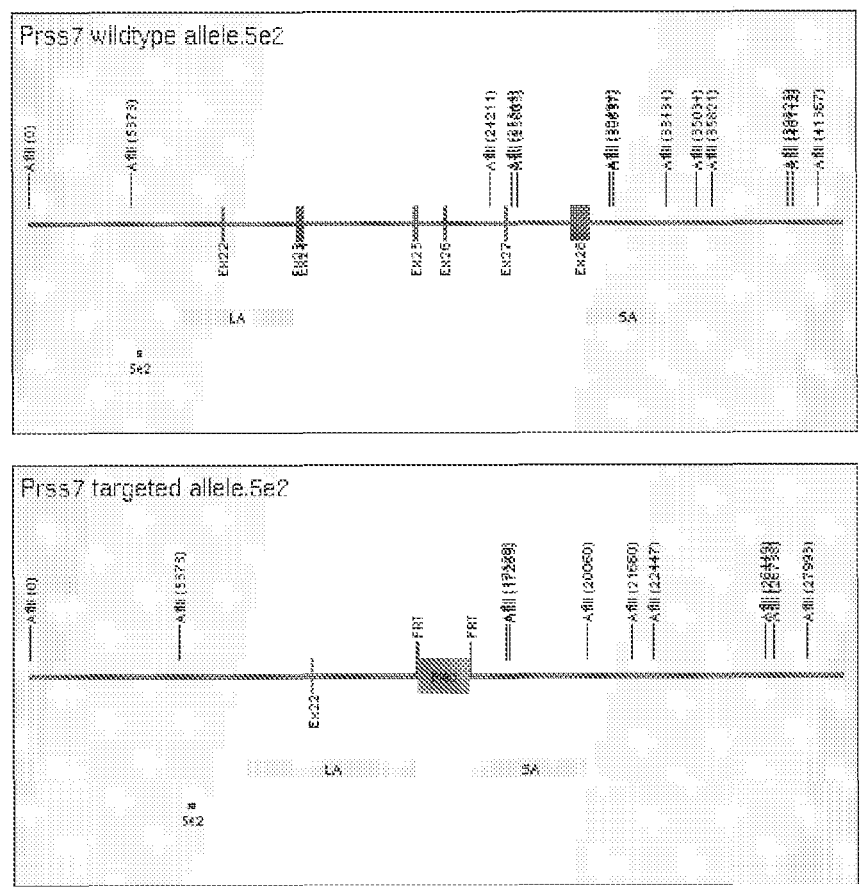

Fig. 13

| | |
|---|---|
| accacc atg aat cca ctc ctg atc ctt acc ttt gtg gca gct gct ctt<br>       Met Asn Pro Leu Leu Ile Leu Thr Phe Val Ala Ala Ala Leu<br>       1                     5                          10 | 48 |
| gct gcc ccc ttt gat gat gat gac aag atc gtt ggg ggc tac aac tgt<br>Ala Ala Pro Phe Asp Asp Asp Asp Lys Ile Val Gly Gly Tyr Asn Cys<br>15                    20                    25                    30 | 96 |
| gag gag aat tct gtc ccc tac cag gtg tcc ctg aat tct ggc tac cac<br>Glu Glu Asn Ser Val Pro Tyr Gln Val Ser Leu Asn Ser Gly Tyr His<br>                  35                    40                    45 | 144 |
| ttc tgt ggt ggc tcc ctc atc aac gaa cag tgg gtg gta tca gca ggc<br>Phe Cys Gly Gly Ser Leu Ile Asn Glu Gln Trp Val Val Ser Ala Gly<br>                50                    55                    60 | 192 |
| cac tgc tac aag tcc cgc atc cag gtg aga ctg gga gag cac aac atc<br>His Cys Tyr Lys Ser Arg Ile Gln Val Arg Leu Gly Glu His Asn Ile<br>         65                    70                    75 | 240 |
| gaa gtc ctg gag ggg aat gag cag ttc atc aat gca gcc aag atc atc<br>Glu Val Leu Glu Gly Asn Glu Gln Phe Ile Asn Ala Ala Lys Ile Ile<br>80                    85                    90 | 288 |
| cgc cac ccc caa tac gac agg aag act ctg aac aat gac atc atg tta<br>Arg His Pro Gln Tyr Asp Arg Lys Thr Leu Asn Asn Asp Ile Met Leu<br>95                    100                  105              110 | 336 |
| atc aag ctc tcc tca cgt gca gta atc aac gcc cgc gtg tcc acc atc<br>Ile Lys Leu Ser Ser Arg Ala Val Ile Asn Ala Arg Val Ser Thr Ile<br>                  115                    120                125 | 384 |
| tct ctg ccc acc gcc cct cca gcc act ggc acg aag tgc ctc atc tct<br>Ser Leu Pro Thr Ala Pro Pro Ala Thr Gly Thr Lys Cys Leu Ile Ser<br>                130                    135                  140 | 432 |
| ggc tgg ggc aac act gcg agc tct ggc gcc gac tac cca gac gag ctg<br>Gly Trp Gly Asn Thr Ala Ser Ser Gly Ala Asp Tyr Pro Asp Glu Leu<br>                145                    150                  155 | 480 |
| cag tgc ctg gac gct cct gtg ctg agc cag gct aag tgt gaa gcc tcc<br>Gln Cys Leu Asp Ala Pro Val Leu Ser Gln Ala Lys Cys Glu Ala Ser<br>                160                    165                  170 | 528 |
| tac cct gga aag att acc agc aac atg ttc tgt gtg ggc ttc ctt gag<br>Tyr Pro Gly Lys Ile Thr Ser Asn Met Phe Cys Val Gly Phe Leu Glu<br>175                    180                    185                190 | 576 |
| gga ggc aag gat tca tgt cag ggt gat tct ggt ggc cct gtg gtc tgc<br>Gly Gly Lys Asp Ser Cys Gln Gly Asp Ser Gly Gly Pro Val Val Cys<br>                    195                    200                205 | 624 |
| aat gga cag ctc caa gga gtt gtc tcc tgg ggt gat ggc tgt gcc cag<br>Asn Gly Gln Leu Gln Gly Val Val Ser Trp Gly Asp Gly Cys Ala Gln<br>                210                    215                  220 | 672 |

Fig. 18A

```
aag aac aag cct gga gtc tac acc aag gtc tac aac tat gtg aaa tgg      720
Lys Asn Lys Pro Gly Val Tyr Thr Lys Val Tyr Asn Tyr Val Lys Trp
        225                 230                 235 att aag aac acc ata gct gcc aat agc taa agccccagt atctcttcag          770
Ile Lys Asn Thr Ile Ala Ala Asn Ser
    240                 245 tctctatacc aataaagtga ccctgttctc                                      800
```

Fig. 18B

SEQUENCE LISTING

```
<160> NUMBER OF SEQ ID NOS: 11

<210> SEQ ID NO 1
<211> LENGTH: 3696
<212> TYPE: DNA
<213> ORGANISM: Artificial Sequence
<220> FEATURE:
<223> OTHER INFORMATION: Human enteropeptidase
<220> FEATURE:
<221> NAME/KEY: CDS
<222> LOCATION: (41)..(3100)

<400> SEQUENCE: 1
accagacagt tcttaaatta gcaagccttc aaaaccaaaa atg ggg tcg aaa aga            55
                                              Met Gly Ser Lys Arg
                                                1               5 ggc ata tct tct agg cat cat tct ctc agc tcc tat gaa atc atg ttt          103
Gly Ile Ser Ser Arg His His Ser Leu Ser Ser Tyr Glu Ile Met Phe
         10                  15                  20 gca gct ctc ttt gcc ata ttg gta gtg ctc tgt gct gga tta att gca          151
Ala Ala Leu Phe Ala Ile Leu Val Val Leu Cys Ala Gly Leu Ile Ala
             25                  30                  35 gta tcc tgc ctg aca atc aag gaa tcc caa cga ggt gca gca ctt gga          199
Val Ser Cys Leu Thr Ile Lys Glu Ser Gln Arg Gly Ala Ala Leu Gly
         40                  45                  50 cag agt cat gaa gcc aga gcg aca ttt aaa ata aca tcc gga gtt aca          247
Gln Ser His Glu Ala Arg Ala Thr Phe Lys Ile Thr Ser Gly Val Thr
     55                  60                  65 tat aat cct aat ttg caa gac aaa ctc tca gtg gat ttc aaa gtt ctt          295
Tyr Asn Pro Asn Leu Gln Asp Lys Leu Ser Val Asp Phe Lys Val Leu
 70                  75                  80                  85 gct ttt gac ctt cag caa atg ata gat gag atc ttt cta tca agc aat          343
Ala Phe Asp Leu Gln Gln Met Ile Asp Glu Ile Phe Leu Ser Ser Asn
                 90                  95                 100 ctg aag aat gaa tat aag aac tca aga gtt tta caa ttt gaa aat ggc          391
Leu Lys Asn Glu Tyr Lys Asn Ser Arg Val Leu Gln Phe Glu Asn Gly
             105                 110                 115 agc att ata gtc gta ttt gac ctt ttc ttt gcc cag tgg gtg tca gat          439
Ser Ile Ile Val Val Phe Asp Leu Phe Phe Ala Gln Trp Val Ser Asp
         120                 125                 130
```

```
caa aat gta aaa gaa gaa ctg att caa ggc ctt gaa gca aat aaa tcc        487
Gln Asn Val Lys Glu Glu Leu Ile Gln Gly Leu Glu Ala Asn Lys Ser
    135                 140                 145 agc caa ctg gtc act ttc cat att gat ttg aac agc gtt gat atc cta        535
Ser Gln Leu Val Thr Phe His Ile Asp Leu Asn Ser Val Asp Ile Leu
150                 155                 160                 165 gac aag cta aca acc acc agt cat ctg gca act cca gga aat gtc tca        583
Asp Lys Leu Thr Thr Thr Ser His Leu Ala Thr Pro Gly Asn Val Ser
            170                 175                 180 ata gag tgc ctg cct ggt tca agt cct tgt act gat gct cta acg tgt        631
Ile Glu Cys Leu Pro Gly Ser Ser Pro Cys Thr Asp Ala Leu Thr Cys
                185                 190                 195 ata aaa gct gat tta ttt tgt gat gga gaa gta aac tgt cca gat ggt        679
Ile Lys Ala Asp Leu Phe Cys Asp Gly Glu Val Asn Cys Pro Asp Gly
            200                 205                 210 tct gac gaa gac aat aaa atg tgt gcc aca gtt tgt gat gga aga ttt        727
Ser Asp Glu Asp Asn Lys Met Cys Ala Thr Val Cys Asp Gly Arg Phe
            215                 220                 225 ttg tta act gga tca tct ggg tct ttc cag gct act cat tat cca aaa        775
Leu Leu Thr Gly Ser Ser Gly Ser Phe Gln Ala Thr His Tyr Pro Lys
230                 235                 240                 245 cct tct gaa aca agt gtt gtc tgc cag tgg atc ata cgt gta aac caa        823
Pro Ser Glu Thr Ser Val Val Cys Gln Trp Ile Ile Arg Val Asn Gln
            250                 255                 260 gga ctt tcc att aaa ctg agc ttc gat gat ttt aat aca tat tat aca        871
Gly Leu Ser Ile Lys Leu Ser Phe Asp Asp Phe Asn Thr Tyr Tyr Thr
                265                 270                 275 gat ata tta gat att tat gaa ggt gta gga tca agc aag att tta aga        919
Asp Ile Leu Asp Ile Tyr Glu Gly Val Gly Ser Ser Lys Ile Leu Arg
            280                 285                 290 gct tct att tgg gaa act aat cct ggc aca ata aga att ttt tcc aac        967
Ala Ser Ile Trp Glu Thr Asn Pro Gly Thr Ile Arg Ile Phe Ser Asn
295                 300                 305 caa gtt act gcc acc ttt ctt ata gaa tct gat gaa agt gat tat gtt       1015
Gln Val Thr Ala Thr Phe Leu Ile Glu Ser Asp Glu Ser Asp Tyr Val
310                 315                 320                 325 ggc ttt aat gca aca tat act gca ttt aac agc agt gag ctt aat aat       1063
Gly Phe Asn Ala Thr Tyr Thr Ala Phe Asn Ser Ser Glu Leu Asn Asn
            330                 335                 340 tat gag aaa att aat tgt aac ttt gag gat ggc ttt tgt ttc tgg gtc       1111
Tyr Glu Lys Ile Asn Cys Asn Phe Glu Asp Gly Phe Cys Phe Trp Val
                345                 350                 355 cag gat cta aat gat gat aat gaa tgg gaa agg att cag gga agc acc       1159
Gln Asp Leu Asn Asp Asp Asn Glu Trp Glu Arg Ile Gln Gly Ser Thr
            360                 365                 370 ttt tct cct ttt act gga ccc aat ttt gac cac act ttt ggc aat gct       1207
Phe Ser Pro Phe Thr Gly Pro Asn Phe Asp His Thr Phe Gly Asn Ala
375                 380                 385 tca gga ttt tac att tct acc cca act gga cca ggg gga aga caa gaa       1255
Ser Gly Phe Tyr Ile Ser Thr Pro Thr Gly Pro Gly Gly Arg Gln Glu
390                 395                 400                 405 cga gtg ggg ctt tta agc ctc cct ttg gac ccc act ttg gag cca gct       1303
Arg Val Gly Leu Leu Ser Leu Pro Leu Asp Pro Thr Leu Glu Pro Ala
            410                 415                 420 tgc ctt agt ttc tgg tat cat atg tat ggt gaa aat gtc cat aaa tta       1351
Cys Leu Ser Phe Trp Tyr His Met Tyr Gly Glu Asn Val His Lys Leu
            425                 430                 435 agc att aat atc agc aat gac caa aat atg gag aag aca gtt ttc caa       1399
Ser Ile Asn Ile Ser Asn Asp Gln Asn Met Glu Lys Thr Val Phe Gln
            440                 445                 450
```

-continued

| | | |
|---|---|---|
| aag gaa gga aat tat gga gac aat tgg aat tat gga caa gta acc cta<br>Lys Glu Gly Asn Tyr Gly Asp Asn Trp Asn Tyr Gly Gln Val Thr Leu<br>455                     460                     465 | 1447 |
| aat gaa aca gtt aaa ttt aag gtt gct ttt aat gct ttt aaa aac aag<br>Asn Glu Thr Val Lys Phe Lys Val Ala Phe Asn Ala Phe Lys Asn Lys<br>470                     475                     480                     485 | 1495 |
| atc ctg agt gat att gcg ttg gat gac att agc cta aca tat ggg att<br>Ile Leu Ser Asp Ile Ala Leu Asp Asp Ile Ser Leu Thr Tyr Gly Ile<br>                    490                     495                     500 | 1543 |
| tgc aat ggg agt ctt tat cca gaa cca act ttg gtg cca act cct cca<br>Cys Asn Gly Ser Leu Tyr Pro Glu Pro Thr Leu Val Pro Thr Pro Pro<br>                505                     510                     515 | 1591 |
| cca gaa ctt cct acg gac tgt gga gga cct ttt gag ctg tgg gag cca<br>Pro Glu Leu Pro Thr Asp Cys Gly Gly Pro Phe Glu Leu Trp Glu Pro<br>520                     525                     530 | 1639 |
| aat aca aca ttc agt tct acg aac ttt cca aac agc tac cct aat ctg<br>Asn Thr Thr Phe Ser Ser Thr Asn Phe Pro Asn Ser Tyr Pro Asn Leu<br>535                     540                     545 | 1687 |
| gct ttc tgt gtt tgg att tta aat gca caa aaa gga aag aat ata caa<br>Ala Phe Cys Val Trp Ile Leu Asn Ala Gln Lys Gly Lys Asn Ile Gln<br>550                     555                     560                     565 | 1735 |
| ctt cat ttt caa gaa ttt gac tta gaa aat att aac gat gta gtt gaa<br>Leu His Phe Gln Glu Phe Asp Leu Glu Asn Ile Asn Asp Val Val Glu<br>                    570                     575                     580 | 1783 |
| ata aga gat ggt gaa gaa gct gat tcc ttg ctc tta gct gtg tac aca<br>Ile Arg Asp Gly Glu Glu Ala Asp Ser Leu Leu Leu Ala Val Tyr Thr<br>                    585                     590                     595 | 1831 |
| ggg cct ggc cca gta aag gat gtg ttc tct acc acc aac aga atg act<br>Gly Pro Gly Pro Val Lys Asp Val Phe Ser Thr Thr Asn Arg Met Thr<br>600                     605                     610 | 1879 |
| gtg ctt ctc atc act aac gat gtg ttg gca aga gga ggg ttt aaa gca<br>Val Leu Leu Ile Thr Asn Asp Val Leu Ala Arg Gly Gly Phe Lys Ala<br>615                     620                     625 | 1927 |
| aac ttt act act ggc tat cac ttg ggg att cca gag cca tgc aag gca<br>Asn Phe Thr Thr Gly Tyr His Leu Gly Ile Pro Glu Pro Cys Lys Ala<br>630                     635                     640                     645 | 1975 |
| gac cat ttt caa tgt aaa aat gga gag tgt gtt cca ctg gtg aat ctc<br>Asp His Phe Gln Cys Lys Asn Gly Glu Cys Val Pro Leu Val Asn Leu<br>                    650                     655                     660 | 2023 |
| tgt gac ggt cat ctg cac tgt gag gat ggc tca gat gaa gca gat tgt<br>Cys Asp Gly His Leu His Cys Glu Asp Gly Ser Asp Glu Ala Asp Cys<br>                    665                     670                     675 | 2071 |
| gtg cgt ttt ttc aat ggc aca acg aac aac aat ggt tta gtg cgg ttc<br>Val Arg Phe Phe Asn Gly Thr Thr Asn Asn Asn Gly Leu Val Arg Phe<br>680                     685                     690 | 2119 |
| aga atc cag agc ata tgg cat aca gct tgt gct gag aac tgg acc acc<br>Arg Ile Gln Ser Ile Trp His Thr Ala Cys Ala Glu Asn Trp Thr Thr<br>695                     700                     705 | 2167 |
| cag att tca aat gat gtt tgt caa ctg ctg gga cta ggg agt gga aac<br>Gln Ile Ser Asn Asp Val Cys Gln Leu Leu Gly Leu Gly Ser Gly Asn<br>710                     715                     720                     725 | 2215 |
| tca tca aag cca atc ttc tct acc gat ggt gga cca ttt gtc aaa tta<br>Ser Ser Lys Pro Ile Phe Ser Thr Asp Gly Gly Pro Phe Val Lys Leu<br>                    730                     735                     740 | 2263 |
| aac aca gca cct gat ggc cac tta ata cta aca ccc agt caa cag tgt<br>Asn Thr Ala Pro Asp Gly His Leu Ile Leu Thr Pro Ser Gln Gln Cys<br>                    745                     750                     755 | 2311 |
| tta cag gat tcc ttg att cgg tta cag tgt aac cat aaa tct tgt gga<br>Leu Gln Asp Ser Leu Ile Arg Leu Gln Cys Asn His Lys Ser Cys Gly<br>760                     765                     770 | 2359 |

| | |
|---|---|
| aaa aaa ctg gca gct caa gac atc acc cca aag att gtt gga gga agt<br>Lys Lys Leu Ala Ala Gln Asp Ile Thr Pro Lys Ile Val Gly Gly Ser<br>775                      780                      785 | 2407 |
| aat gcc aaa gaa ggg gcc tgg ccc tgg gtt gtg ggt ctg tat tat ggc<br>Asn Ala Lys Glu Gly Ala Trp Pro Trp Val Val Gly Leu Tyr Tyr Gly<br>790                      795                      800                      805 | 2455 |
| ggc cga ctg ctc tgc ggc gca tct ctc gtc agc agt gac tgg ctg gtg<br>Gly Arg Leu Leu Cys Gly Ala Ser Leu Val Ser Ser Asp Trp Leu Val<br>                     810                      815                      820 | 2503 |
| tcc gcc gca cac tgc gtg tat ggg aga aac tta gag cca tcc aag tgg<br>Ser Ala Ala His Cys Val Tyr Gly Arg Asn Leu Glu Pro Ser Lys Trp<br>                     825                      830                      835 | 2551 |
| aca gca atc cta ggc ctg cat atg aaa tca aat ctg acc tct cct caa<br>Thr Ala Ile Leu Gly Leu His Met Lys Ser Asn Leu Thr Ser Pro Gln<br>                     840                      845                      850 | 2599 |
| aca gtc cct cga tta ata gat gaa att gtc ata aac cct cat tac aat<br>Thr Val Pro Arg Leu Ile Asp Glu Ile Val Ile Asn Pro His Tyr Asn<br>855                      860                      865 | 2647 |
| agg cga aga aag gac aac gac att gcc atg atg cat ctg gaa ttt aaa<br>Arg Arg Arg Lys Asp Asn Asp Ile Ala Met Met His Leu Glu Phe Lys<br>870                      875                      880                      885 | 2695 |
| gtg aat tac aca gat tac ata caa cct att tgt tta ccg gaa gaa aat<br>Val Asn Tyr Thr Asp Tyr Ile Gln Pro Ile Cys Leu Pro Glu Glu Asn<br>                     890                      895                      900 | 2743 |
| caa gtt ttt cct cca gga aga aat tgt tct att gct ggt tgg ggg acg<br>Gln Val Phe Pro Pro Gly Arg Asn Cys Ser Ile Ala Gly Trp Gly Thr<br>                     905                      910                      915 | 2791 |
| gtt gta tat caa ggt act act gca aac ata ttg caa gaa gct gat gtt<br>Val Val Tyr Gln Gly Thr Thr Ala Asn Ile Leu Gln Glu Ala Asp Val<br>                     920                      925                      930 | 2839 |
| cct ctt cta tca aat gag aga tgc caa cag cag atg cca gaa tat aac<br>Pro Leu Leu Ser Asn Glu Arg Cys Gln Gln Gln Met Pro Glu Tyr Asn<br>935                      940                      945 | 2887 |
| att act gaa aat atg ata tgt gca ggc tat gaa gaa gga gga ata gat<br>Ile Thr Glu Asn Met Ile Cys Ala Gly Tyr Glu Glu Gly Gly Ile Asp<br>950                      955                      960                      965 | 2935 |
| tct tgt cag ggg gat tca gga gga cca tta atg tgc caa gaa aac aac<br>Ser Cys Gln Gly Asp Ser Gly Gly Pro Leu Met Cys Gln Glu Asn Asn<br>                     970                      975                      980 | 2983 |
| agg tgg ttc ctt gct ggt gtg acc tca ttt gga tac aag tgt gcc ctg<br>Arg Trp Phe Leu Ala Gly Val Thr Ser Phe Gly Tyr Lys Cys Ala Leu<br>                     985                      990                      995 | 3031 |
| cct aat cgc ccc gga gtg tat gcc agg gtc tca agg ttt acc gaa<br>Pro Asn Arg Pro Gly Val Tyr Ala Arg Val Ser Arg Phe Thr Glu<br>                     1000                    1005                    1010 | 3076 |
| tgg ata caa agt ttt cta cat tag cgcatttctt aaactaaaca ggaaagtcgc<br>Trp Ile Gln Ser Phe Leu His<br>             1015 | 3130 |
| attattttcc cattctactc tagaaagcat ggaaattaag tgtttcgtac aaaaattta | 3190 |
| aaaagttacc aaaggttttt attcttacct atgtcaatga aatgctaggg ggccagggaa | 3250 |
| acaaaatttt aaaataata aaattcacca tagcaataca gaataacttt aaaataccat | 3310 |
| taaatacatt tgtatttcat tgtgaacagg tatttcttca cagatctcat ttttaaaatt | 3370 |
| cttaatgatt attttatta cttactgttg tttaagggga tgttatttta aagcatatac | 3430 |
| catacactta agaaatttga gcagaattta aaaagaaag aaataaatt gttttccca | 3490 |
| aagtatgtca ctgttggaaa taactgcca taaattttct agttccagtt tagtttgctg | 3550 |
| ctattagcag aaactcaatt gtttctctgt cttttctatc aaaattttca acatatgcat | 3610 |

-continued

```
aaccttagta ttttcccaac caatagaaac tatttattgt aagcttatgt cacaggcctg    3670
gactaaattg atttttacgtt cctctt                                        3696
```

<210> SEQ ID NO 2
<211> LENGTH: 1019
<212> TYPE: PRT
<213> ORGANISM: Artificial Sequence
<220> FEATURE:
<223> OTHER INFORMATION: Synthetic Construct

<400> SEQUENCE: 2

```
Met Gly Ser Lys Arg Gly Ile Ser Ser Arg His His Ser Leu Ser Ser
1               5                   10                  15

Tyr Glu Ile Met Phe Ala Ala Leu Phe Ala Ile Leu Val Val Leu Cys
                20                  25                  30

Ala Gly Leu Ile Ala Val Ser Cys Leu Thr Ile Lys Glu Ser Gln Arg
            35                  40                  45

Gly Ala Ala Leu Gly Gln Ser His Glu Ala Arg Ala Thr Phe Lys Ile
        50                  55                  60

Thr Ser Gly Val Thr Tyr Asn Pro Asn Leu Gln Asp Lys Leu Ser Val
65                  70                  75                  80

Asp Phe Lys Val Leu Ala Phe Asp Leu Gln Gln Met Ile Asp Glu Ile
                85                  90                  95

Phe Leu Ser Ser Asn Leu Lys Asn Glu Tyr Lys Asn Ser Arg Val Leu
            100                 105                 110

Gln Phe Glu Asn Gly Ser Ile Ile Val Val Phe Asp Leu Phe Phe Ala
        115                 120                 125

Gln Trp Val Ser Asp Gln Asn Val Lys Glu Glu Leu Ile Gln Gly Leu
130                 135                 140

Glu Ala Asn Lys Ser Ser Gln Leu Val Thr Phe His Ile Asp Leu Asn
145                 150                 155                 160

Ser Val Asp Ile Leu Asp Lys Leu Thr Thr Thr Ser His Leu Ala Thr
                165                 170                 175

Pro Gly Asn Val Ser Ile Glu Cys Leu Pro Gly Ser Ser Pro Cys Thr
            180                 185                 190

Asp Ala Leu Thr Cys Ile Lys Ala Asp Leu Phe Cys Asp Gly Glu Val
        195                 200                 205

Asn Cys Pro Asp Gly Ser Asp Glu Asp Asn Lys Met Cys Ala Thr Val
    210                 215                 220

Cys Asp Gly Arg Phe Leu Leu Thr Gly Ser Ser Gly Ser Phe Gln Ala
225                 230                 235                 240

Thr His Tyr Pro Lys Pro Ser Glu Thr Ser Val Val Cys Gln Trp Ile
                245                 250                 255

Ile Arg Val Asn Gln Gly Leu Ser Ile Lys Leu Ser Phe Asp Asp Phe
            260                 265                 270

Asn Thr Tyr Tyr Thr Asp Ile Leu Asp Ile Tyr Glu Gly Val Gly Ser
        275                 280                 285

Ser Lys Ile Leu Arg Ala Ser Ile Trp Glu Thr Asn Pro Gly Thr Ile
    290                 295                 300

Arg Ile Phe Ser Asn Gln Val Thr Ala Thr Phe Leu Ile Glu Ser Asp
305                 310                 315                 320

Glu Ser Asp Tyr Val Gly Phe Asn Ala Thr Tyr Thr Ala Phe Asn Ser
                325                 330                 335

Ser Glu Leu Asn Asn Tyr Glu Lys Ile Asn Cys Asn Phe Glu Asp Gly
            340                 345                 350
```

-continued

```
Phe Cys Phe Trp Val Gln Asp Leu Asn Asp Asp Asn Glu Trp Glu Arg
            355                 360                 365
Ile Gln Gly Ser Thr Phe Ser Pro Phe Thr Gly Pro Asn Phe Asp His
    370                 375                 380
Thr Phe Gly Asn Ala Ser Gly Phe Tyr Ile Ser Thr Pro Thr Gly Pro
385                 390                 395                 400
Gly Gly Arg Gln Glu Arg Val Gly Leu Leu Ser Leu Pro Leu Asp Pro
                405                 410                 415
Thr Leu Glu Pro Ala Cys Leu Ser Phe Trp Tyr His Met Tyr Gly Glu
            420                 425                 430
Asn Val His Lys Leu Ser Ile Asn Ile Ser Asp Gln Asn Met Glu
    435                 440                 445
Lys Thr Val Phe Gln Lys Glu Gly Asn Tyr Gly Asp Asn Trp Asn Tyr
450                 455                 460
Gly Gln Val Thr Leu Asn Glu Thr Val Lys Phe Lys Val Ala Phe Asn
465                 470                 475                 480
Ala Phe Lys Asn Lys Ile Leu Ser Asp Ile Ala Leu Asp Asp Ile Ser
                485                 490                 495
Leu Thr Tyr Gly Ile Cys Asn Gly Ser Leu Tyr Pro Glu Pro Thr Leu
            500                 505                 510
Val Pro Thr Pro Pro Glu Leu Pro Thr Asp Cys Gly Gly Pro Phe
    515                 520                 525
Glu Leu Trp Glu Pro Asn Thr Thr Phe Ser Ser Thr Asn Phe Pro Asn
    530                 535                 540
Ser Tyr Pro Asn Leu Ala Phe Cys Val Trp Ile Leu Asn Ala Gln Lys
545                 550                 555                 560
Gly Lys Asn Ile Gln Leu His Phe Gln Glu Phe Asp Leu Glu Asn Ile
                565                 570                 575
Asn Asp Val Val Glu Ile Arg Asp Gly Glu Glu Ala Asp Ser Leu Leu
            580                 585                 590
Leu Ala Val Tyr Thr Gly Pro Gly Pro Val Lys Asp Val Phe Ser Thr
        595                 600                 605
Thr Asn Arg Met Thr Val Leu Leu Ile Thr Asn Asp Val Leu Ala Arg
    610                 615                 620
Gly Gly Phe Lys Ala Asn Phe Thr Thr Gly Tyr His Leu Gly Ile Pro
625                 630                 635                 640
Glu Pro Cys Lys Ala Asp His Phe Gln Cys Lys Asn Gly Glu Cys Val
                645                 650                 655
Pro Leu Val Asn Leu Cys Asp Gly His Leu His Cys Glu Asp Gly Ser
            660                 665                 670
Asp Glu Ala Asp Cys Val Arg Phe Asn Gly Thr Asn Asn Asn
        675                 680                 685
Gly Leu Val Arg Phe Arg Ile Gln Ser Ile Trp His Thr Ala Cys Ala
    690                 695                 700
Glu Asn Trp Thr Thr Gln Ile Ser Asn Asp Val Cys Gln Leu Leu Gly
705                 710                 715                 720
Leu Gly Ser Gly Asn Ser Ser Lys Pro Ile Phe Ser Thr Asp Gly Gly
                725                 730                 735
Pro Phe Val Lys Leu Asn Thr Ala Pro Asp Gly His Leu Ile Leu Thr
            740                 745                 750
Pro Ser Gln Gln Cys Leu Gln Asp Ser Leu Ile Arg Leu Gln Cys Asn
        755                 760                 765
```

His Lys Ser Cys Gly Lys Lys Leu Ala Ala Gln Asp Ile Thr Pro Lys
    770             775                 780

Ile Val Gly Gly Ser Asn Ala Lys Glu Gly Ala Trp Pro Trp Val Val
785             790                 795                 800

Gly Leu Tyr Tyr Gly Gly Arg Leu Leu Cys Gly Ala Ser Leu Val Ser
                805                 810                 815

Ser Asp Trp Leu Val Ser Ala Ala His Cys Val Tyr Gly Arg Asn Leu
            820                 825                 830

Glu Pro Ser Lys Trp Thr Ala Ile Leu Gly Leu His Met Lys Ser Asn
        835                 840                 845

Leu Thr Ser Pro Gln Thr Val Pro Arg Leu Ile Asp Glu Ile Val Ile
    850                 855                 860

Asn Pro His Tyr Asn Arg Arg Lys Asp Asn Asp Ile Ala Met Met
865             870                 875                 880

His Leu Glu Phe Lys Val Asn Tyr Thr Asp Tyr Ile Gln Pro Ile Cys
                885                 890                 895

Leu Pro Glu Glu Asn Gln Val Phe Pro Pro Gly Arg Asn Cys Ser Ile
            900                 905                 910

Ala Gly Trp Gly Thr Val Val Tyr Gln Gly Thr Thr Ala Asn Ile Leu
        915                 920                 925

Gln Glu Ala Asp Val Pro Leu Leu Ser Asn Glu Arg Cys Gln Gln Gln
    930                 935                 940

Met Pro Glu Tyr Asn Ile Thr Glu Asn Met Ile Cys Ala Gly Tyr Glu
945             950                 955                 960

Glu Gly Gly Ile Asp Ser Cys Gln Gly Asp Ser Gly Gly Pro Leu Met
                965                 970                 975

Cys Gln Glu Asn Asn Arg Trp Phe Leu Ala Gly Val Thr Ser Phe Gly
            980                 985                 990

Tyr Lys Cys Ala Leu Pro Asn Arg  Pro Gly Val Tyr Ala  Arg Val Ser
        995                 1000                1005

Arg Phe  Thr Glu Trp Ile Gln  Ser Phe Leu His
    1010                1015

<210> SEQ ID NO 3
<211> LENGTH: 17480
<212> TYPE: DNA
<213> ORGANISM: Artificial Sequence
<220> FEATURE:
<223> OTHER INFORMATION: Vector

<400> SEQUENCE: 3
cggccgcccc tgtcagttgc cgggatgagc ttaagtcctt tgtccatcat tcttagatcc    60
tccccttttc ctttcttcca ggaaagcaag gagacacttc atcaaagact ccactccatt   120
atcatctgag tgccttgcag aaagtttaaa ttccaatctg gtacacatgg cgggttctct   180
cattccatac catttccaaa ataactctcc ttcccttaac tagtagaaca ttttttagtg   240
aatgattaag cacaattgag gccacatgga tatcttaact actttttctta ccatttaaaa   300 tcccttcctc ttcataaact ttgcctgact tactttctct tcatgctgga tatacctggt   360
aacattatgt tgatcttatt gattagaagg aatatccata gaatgtgtaa tttggaattt   420
tatttatcac cacaacactc aaattgatat gaagcaagtg ttttttgcatc ataatgctca   480 aggctttaga agtagatctt tttgtcttta aagagttctg caaatcgaca ggatggtgga   540
atgttgcaaa ggtgtatctg tgagtggggg ccaaaaagcta ttaggggttg aactgtggga   600
accttgggcc cacataagga ctaaacatag ggggctgtgg atagaccaag tgaaagatta   660

```
tttccaggaa acgaaggcaa agaaatgcag atcttgacat ttgatcttgg ggatacttac    720
aggcactttt accgtagcca gaacaatgac tactatggga agaacaaac tgaatcccag     780
gcacaatccc ataagggcct aggtctcgtt ctagggaatg gaacttacat gtcagaccta    840
tcttggagga agaactcaca agcccccgag tccgtgaatg tgcatctgcc ttggacatac    900
attgattcga gagagaggca caatgaacct ttcagtacac aaaggactta aatccagttt    960
aggaagacta aggaaaaaaa aaaaacaata gatggttact tgcacctagg actggagcat   1020
gtgtttggga acgattggac actaattgta tcaacaatta tatcagagtg cccataaagc   1080
gagattcaga aacctggcca agaaaaacaa ggtttattgg gggagggggg aatgggaggt   1140
tttagtactc tgctgggcac tgttgcacat gcgtgtttga gctctatggt tagtgaaaag   1200
atacaaatat gcaaatatgc ttgtctgttc tcaacactta taagaactgt ttgccatttt   1260
tacatcttgg aataatctag actttttttt tgtaggaatg gaaagtattc tcaggaggga   1320
agaagaactc ataatatctg tctgactgtc tccatttgga ccgagacaca tttagtttga   1380
tacgactcaa gaactgaatt tatttcttct tatgtttttt ttccagtaaa ggaagatcaa   1440
aaactagccc gaatcagtct acactgtgga tttcaaaaag cacgaggaag gaaagtggca   1500
tggaggtata ataatgaact ggcattgttc tggaaaaata aatagttttt gtaatcgttg   1560
atcaatgtaa ggaatggcat catcaccttg gaatggcttg aaatctcaaa ggatctgcaa   1620
gatggactgt aagctccccc ttgaggcaaa tgtcaaaata attttttagaa gtttatagtt   1680
tcacttacaa catatgctga gtgagacctg gttactctcc taaaggatac acctaaattt   1740
catgtaaaag aaatggacca tgcggatata atttctgtgg accaatctgg aatacctgtg   1800
ttgggagtag ttactcttgc tctctttctt ttttcatctt cataaatttt gatctatgtc   1860
atgtaatata aattgtattt caatttacgg tgtgcagaaa cattctacct ttgcaaaagt   1920
gtttgatgaa aatagagtgt tctgatattt atatttatga catttgattt ttacatatat   1980
agtgttttca ttaaaaactg aattcacaca gacacaaaga aatccttgca tagggaaaac   2040
atttctttgg taggatagtt catgtttgtt ctgtttcttt gctttgggtt cgataaagtt   2100
taggaagtat cttcagaaat aagaaactat ttcattgact gtgctgttaa tctgctgaaa   2160
cactttactt agaggcaaga actgtctaac ttcaattgtg caagacacgt gccttacaat   2220
tattcttaat ttaaaattaa acagattttt gtaataaagt atctttaata atacttgtat   2280
agacaccaat agagttaacc ttgaaaaaaa tggcatctgc agtacaaatc acaggtcttc   2340
acatgttgcc tatagaattg caaatagctc cccagagtgt caggaatcaa tgtggctcct   2400
ccctttcaat caaacagagt aactatttga aggctttgga gtcagacagt tgctgtttgg   2460
ctgaggttct cctaactgaa tttagcctgt ataatatata aagctcaatg gtttccagca   2520
gtgtgatgct aagcagaaca cactgatatt aatgattaaa agaagaagaa gaagaaaaac   2580
aaaactacaa atcacatcat ttaatgggcc agggactcga ggttgctgat gtttgcttat   2640
ctttgatgag tgttgtttgt ggttgtgaac tgtggcttcc ttctgtctga tggagtttcc   2700
tcaacacgta gcacttgttc ttctcaagag agttgtaact attttgtctt caaatgtccc   2760
tgtgtcactt ttagccaaat aaaagagttct tgtttctgaa gaatgatctt tggtgttgtc   2820
tacattctta agggaccaag gcccagatgt gtttcatcat tacctgagga tgaaatcaaa   2880
cattgcatgt gaagagccca gacagcggca gatctgaagg aacagggatg tttcttcttt   2940
ctctgtcagt cttgttcagt tagacagtcc ttaagtagac ttggtttttc caaacaagag   3000
gcaaaaatgg gctctcagat cttttcctgc tgccttgaga ctgaatggac aactgcattc   3060
```

-continued

```
taagctcagc tgcccccact tagctccatc cttttgggtc aaatgggagg ccagctgttt      3120
ggatctatgt tttgcctgta tgccaactcc actcgtttct ccatttagct atccagaact      3180
ctaacagctg aaggatggaa gcacaaactg aaagggaag gctggtgttt cttttattat       3240
caaggtcagg aaagcatcca gtgttaatgg caaactccat ctgtgacaag ggtgggaaaa      3300
caattctctg tcctcttaaa agatggtgat gataccatct ttgaaaaggg tttgtaaagt      3360
tttagctggc ccttgcaaaa ccggtacatg atgtaactgc tctgtatttt tcagaacata     3420
gtgttaatat atgttgggaa atgatccatt caagtattca caaacaaacc acacactcgc      3480
ttcttcttct tattttccct tctaggttga ggttattggc aaggttttcc tgagaagagt      3540
gtgcagagac ctttgattat tagtgtcagt gcttgtggga acatgcagtc ccctatcatc      3600
tgggcgaatc ttcttttatt gaaatgtttt ccatgctctg actgtcttca gttagaacat      3660
gattgtctcg aaacctctgt cctccatttt cagggtcact gtcacctgta gagttgtctc      3720
tagtgtctct taaacgcatc gaattgtaat tatcccatct aaagcatagc tcaagctttc      3780
tcccttcccc aaagcaaata ttagcagttg ctttttttaaa aaaattttt aaatacaact      3840
catttgaacc ctattcattc ttgcattgga ttaattcatg aaagaaaaat gaaaacaatg      3900
aatgtgttta tgttgatgaa atatgtctgt gtcagtgtta tgtgtgtgt gtgtgtgtgt       3960
gtgtgtgtgt gtgtgtgtgt atgtatttgt gtcaagttag catggatttc agcagattct      4020
gtgtgataaa ctgaactgac atttgcattt tctctggaaa taatccaaga gattaaagaa      4080
gtggagcaaa ttaatttatt acacattttt tgcctttagt ggggaattca gctgtgtctg     4140
aacaaatttt tcacatgttc aggatagtct ctaaactgta caattttccg cggctcgagc      4200
ctaggggtaa ccgaagttcc tatactttct agagaatagg aacttcggaa taggaacttc      4260
ttataatcta gaactagtgg atcgatccac gattcgaggg cccctgcagg tcaattctac      4320
cgggtagggg aggcgctttt cccaaggcag tctggagcat gcgctttagc agccccgctg      4380
ggcacttggc gctacacaag tggcctctgg cctcgcacac attccacatc caccggtagg      4440
cgccaaccgg ctccgttctt tggtggcccc ttcgcgccac cttctactcc tcccctagtc      4500
aggaagttcc ccccgcccc gcagctcgcg tcgtgcagga cgtgacaaat ggaagtagca      4560
cgtctcacta gtctcgtgca gatggacagc accgctgagc aatggaagcg ggtaggcctt     4620
tggggcagcg gccaatagca gctttgctcc ttcgcttct gggctcagag ctgggaagg       4680
ggtgggtccg ggggcgggct caggggcggg ctcaggggcg gggcgggcgc ccgaaggtcc      4740
tccggaggcc cggcattctg cacgcttcaa aagcgcacgt ctgccgcgct gttctcctct      4800
tcctcatctc cgggcctttc gacctgcagc caatatggga tcggccattg aacaagatgg      4860
attgcacgca ggttctccgg ccgcttgggt ggagaggcta ttcggctatg actgggcaca      4920
acagacaatc ggctgctctg atgccgccgt gttccggctg tcagcgcagg ggcgcccggt      4980
tcttttgtc aagaccgacc tgtccggtgc cctgaatgaa ctgcaggacg aggcagcgcg       5040
gctatcgtgg ctggccacga cgggcgttcc ttgcgcagct gtgctcgacg ttgtcactga      5100
agcgggaagg gactggctgc tattgggcga agtgccgggg caggatctcc tgtcatctca      5160
ccttgctcct gccgagaaag tatccatcat ggctgatgca atgcggcggc tgcatacgct      5220
tgatccggct acctgcccat tcgaccacca agcgaaacat cgcatcgagc gagcacgtac      5280
tcggatggaa gccggtcttg tcgatcagga tgatctggac gaagagcatc aggggctcgc      5340
gccagccgaa ctgttcgcca ggctcaaggc gcgcatgccc gacggcgagg atctcgtcgt      5400
gacccatggc gatgcctgct tgccgaatat catggtggaa aatggccgct ttctggatt      5460
```

```
catcgactgt ggccggctgg gtgtggcgga ccgctatcag gacatagcgt tggctacccg    5520
tgatattgct gaaagagcttg gcggcgaatg ggctgaccgc ttcctcgtgc tttacggtat    5580
cgccgctccc gattcgcagc gcatcgcctt ctatcgcctt cttgacgagt tcttctgagg    5640
ggatcgatcc gctgtaagtc tgcagaaatt gatgatctat aaacaataa agatgtccac     5700
taaaatggaa gttttcctg tcatactttg ttaagaaggg tgagaacaga gtacctacat     5760
tttgaatgga aggattggag ctacgggggt ggggtgggg tgggattaga taaatgcctg     5820
ctctttactg aaggctcttt actattgctt tatgataatg tttcatagtt ggatatcata    5880
atttaaacaa gcaaaccaa attaagggcc agctcattcc tcccactcat gatctataga     5940
tctatagatc tctcgtggga tcattgtttt tctcttgatt cccactttgt ggttctaagt    6000
actgtggttt ccaaatgtgt cagtttcata gcctgaagaa cgagatcagc agcctctgtt    6060
ccacatacac ttcattctca gtattgtttt gccaagttct aattccatca gaagctgact    6120
ctagatcctg caggaattaa ttcatatgaa gttcctatac tttctagaga ataggaactt    6180
cggaatagga acttcaaaat gtcgcggcgc gccatgtctt gtggtttcct gaagactgtg    6240
agaaatgttt gcttttgatt acttttatca cgaattattt tgatttcagc aaacatggat    6300
ttcactactt tctcattcct agggaatatg tttcaattac tctagtctat atctaaaacc    6360
acttacagtg ctaaaccctg tgttcaacat ggtctctttc aatcaagtac ttgtgacaca    6420
tcacggttgt aaatcctgaa ttttgggctt aggtgatgga tagtaacgca aattgattat    6480
ttttcttctc tactttttt ttcttttgg tgaatagata acacatgcta atgccaggct      6540
gtaattttta agcaatatta gcatatgact tttctttctc tccttactaa gtagaaaact    6600
tttacttaaa gaaacagtct ttctgtagtc tggtactact cttgggcaaa gcatggctta    6660
cgtggagaaa agaactgaac gctgcaagta atcttgggaa ttaaattaat ttctgaagga    6720
tcagcggaaa ggtaacgcat gctttgttct tgccacaaca agagatggtt cactccggac    6780
tcagtgagat tgcctagtgc tcccgagatt ggtaataact gaagctaatg aactgctaat    6840
gtatggattt acccttaat acttttagac tatgattggc catttggtga cagacgtagt     6900
agaaacaaac tgtaagaaaa agatgaactg atgaagaccc gcttccagtc tcatctactt    6960
cagggctgtt cagtgacaag cccttctatg aggctgtgaa attcattctg gaaagcaaat    7020
gggcttacgc tggtaaaaga ggcagacatg tgcgtagcga ctataaaata acgactacgc    7080
gtaaactact gaaatcacat cgcctatagt tttgaaattt ggttttttcca aagccaggaa   7140
aacttacatt aaaaaataaa attgtttacg aggttttata caatttgacc agcagagggc    7200
aatgttacac caggaatcat aacactgcca ctattctgcc tctgcggata tcccacacat    7260
taaatatttg tatatgtgtg cccacacata gaattaaatg ctctacactt atgtacttac    7320
ttaaatgacg tgtgcatgtt gcttgagtac tcttactttg gaaaaggat aaaagaaaaa     7380
aaaaaaacac aaaacaaagc tatgtgctca ctaaaagcaa ctccatagtt ttagaacacg    7440
aatggtaaag cttatttaaa aagaacgtac gacattctat tatcaacatt ctctttaat    7500
atataagaca acttcaatag aaatataaga aaatgtactt tgtgaatgat cagtatttct    7560
atatacctct ctataaaatg cctcgaaaat ctcaattaat ttcccttttg atgctcacgt    7620
gtgtttgaaa gaaaagtagg ctacaggatg cattgtagga tactttcaag tctcacaaat    7680
gcgcttttca aatctacagt gctcattaat aaaaatccat attcagaatg gctcctggga    7740
cagtgttact ggcctagaa agggcaaaca gtgcttaaat atttttaatc aagcacataa     7800
gcagttaata gctcattgcc atctcacaag aaatttcaca ttttctccga taacttcttc    7860
```

```
cttattttg  ttacagcttt  tagaagaagg  ataccctcca  aagcactatt  tttccatctt   7920
acactaaatg  ccacaattat  ataacattaa  ttaactaagg  gactgaataa  atcaatatgt   7980
ctcaattttg  cctgctcagt  ataatagggc  caattaaaga  aaggattgaa  gacatttagc   8040
taactggctt  ttttggtgta  aatgagcata  aagggtacat  ctatataaag  tctttctttt   8100
ttcaactacc  atgaatataa  gtataatcgt  ggcactaata  ttagttgaaa  ctgtcacctg   8160
actcctacaa  ctttgtagca  gatgctcagc  tgggtcttca  tgtgggtccc  ctgacaattg   8220
tagcaggcac  tgtctctgaa  tctattgcct  gaacctggat  ccccttcctc  tagctgaact   8280
gccttgttgg  gcctcagtgg  aagggtgca  cttagtcctg  caacagtttg  atctgcttgg    8340
gcaggttggt  acccggatgt  gtgtgaggcc  ttcctatctc  aggagggata  gttggggagg   8400
ggctggggag  gatgagcctg  ggaggagagg  agggagggtg  ctgcaatcag  ggatgtaaag   8460
tgaataaata  aattaagaaa  aagaaaaaa   aaggaaataa  tacggttttt  ctctgaaaga   8520
ggcattcaat  taatttgaat  ggctttaaac  tttgttttct  ctttcttact  aatatttaca   8580
tctaggaaac  ctgaataggt  agaattctca  gcataccgga  gaaccatggg  ctctcagaac   8640
gccttattag  aaaggaagtt  gtgaaacctg  tgtgaaaact  ttcaggtgga  ttggctcaaa   8700
cccactggga  tcgctatctg  tcaacactga  cagacagtgc  taaaccccaa  gattctctcg   8760
cagatactaa  atgtagagct  tacaaatttg  ttttattgct  tgagctttgg  ggagtgctga   8820 cttcctgag  cagtggaata  agctgatgct  gttttaacgt  caagtctgtt  aagtaaagtg    8880
tactggtaac  aggatgctaa  ctgttaagag  tgcaattctg  atgtctcttt  gcagtcattt   8940
ctcatcccga  gtttatctgt  agtgggaata  tgagattcag  aggccaattt  cctcagtctc   9000
aaacaaaaat  cactactaat  gtctaaatag  gagaaattac  ataatatact  atgacagaat   9060
ttttgaatag  aggaaggatg  ctgatttta   atacttcaca  aaaagggta   taagagaaga   9120 tctagcttaa  aatagcaaaa  aaaagataca  atataggact  aattatatta  tttttaaatt   9180
atattcatat  ttgtttgcta  agaaagataa  cccttgatt   ctcacgtaac  cccttgtctt   9240
ttgatggttg  tctgaggcgt  atttatccta  tttattctaa  aacttacaat  ttatttcat    9300 gatatttaga  gctttagagt  atgagactaa  gaacagtatt  atggtatatc  atcttcctct   9360
ctgtatgtca  taacagcaat  ggcttaaaac  agtaaattag  actgtcttat  acaaatgaag   9420
atcaaacaat  cctatcagga  aaaaacaaac  ccatatgttt  gttgacatta  cacaaataaa   9480
agccaggcag  tggtggcaca  tacctttaat  cccagcactt  gggaggcaga  ggcaggcgga   9540
tttctgagtt  tgagaccagc  ctggtctaca  gagtgagttc  caggacagcc  agggctacac   9600
agagaaaccc  tgtctcaaaa  caaacaaaaa  gcaagcaagc  aagcaagcaa  gcaagcaacc   9660
aacaagcaaa  agaaattgaa  aaaaaatttc  aaatgtatgt  ggtcaatgtg  tggtggcact   9720
gacacattaa  tggctctctc  tctctctctc  tctctctctc  tctctctctc  tctatatata   9780
tatatatata  tatatatata  tatatatata  tatatatata  tatatatata  tatatatatt   9840
cctatgtacc  aaataaaaat  aaaacatcct  ggcacccacc  taggagttag  tatcaagctt   9900
ccattagggg  cttggtttac  tctcacaaat  ggtccacctc  cggtagatga  tattggcatt   9960
gatgagtttg  cactcctaag  gtagaataaa  cgacatatga  acaggagata  aaattaccaa  10020
cattaatgct  acattttcat  tattggatga  gacataattg  gaagtaaatt  atgttaatac  10080
ttgggaaaag  tggagggcag  agaaactggg  caggatctat  tgtataaggg  aagaatccat  10140
tttcaataga  tataatatca  aacaatatta  tagaccgtta  gcaaaattat  tacttaggac  10200
attaaatatt  gtcagttttt  gggaaagcct  ttagtacacg  tttgaatatc  gtacattata  10260
```

```
ttacaaggtc gctacacatt tctctcgagg atctgatttc tgttctgttc tgttttcccc    10320
ttttcaatgc tgttgagagg atgtgaatag tttaatggat cagctcatat aaaatttgaa    10380
ttaagtttga atgagaaaaa taaatacacc gattataatt taagcctttc tttaaggagg    10440
tataactcat ctttcaagaa aatcaaatcg cctaagaact acacagagta gttctagctt    10500
tagtagttcg gagtttagct ttctagtttt ttttttgctt ttgttatctc attaaattta    10560
aagtcaaagc agtcccaaat ccaaggacga agacaagcgg ttgctccgag ggcctccata    10620
acctccatct gcagttgcca actggtgagc caccgcaggg tgacaaaaga cacctccatg    10680
taacacagca tccaatcctc taggctacaa cctgtggcat ctgcaccatc tgctgtgagg    10740
cttagtgaag gtttctctta attaatttta cttttatttt aaaatttaac taaatttagt    10800
taaattaaaa tctgacccct tttaaaataa ttcttttact caatcaatat cttagtatta    10860
atataaaact atgcctttaa atgtgaaagt cagtgggctg aacctgcaaa ggggaaaagt    10920
gatggttaaa agtgatacaa tatgcatgtg ggaaatcgtc agcagttaaa tcaccatcac    10980
catcaccatc atcatcacca tcaccatcac catcatcacc atcaccatca ccaccctcac    11040
cctcaccctc accctcacac tcaccctcac cctcacccctc accatcatca ttaccatcac    11100
cacgtttgcc tctggattct aggtatatta attttactgt tctctatggt tgttaggaga    11160
caatgtaacc tctagctact gaaataacaa gttgagtgtg cttgttgcct ctccagaata    11220
tttaatgtct ctcctggatg atagcaaaca ataacaatgt gtttaggtgc acggaaatg    11280
gaccaggagc acccaaaatt cttatgagca gtgaaaagaa aaacaaatg ttcaagaggt    11340
agttcctctc ctttccaaag ccttcgtcag acttagcctt tatttgctgc cttccagcca    11400
ctgaacatta tgttgggaaa atagatgctc tgtctaatgt cccaatattt ggtatatttc    11460
acttccactt gataagcaaa caatgcaat gaaagaacac aaagccatta atcttccttt    11520
aacaaaatat caaatagatt ttccgaatca aagagaagtc ttgctgttgt tattttggga    11580
tttgatacta tcttctccaa ccacatgagc agaaagagtta tttcatttaa atagctctat    11640
gcaatgtatt tgctgaagct taggggaaaa aagggggggg ggcagaagtg gatgtagaag    11700
cttagggatg cttgagtcat agaaacttct accgatataa actagtcaca ggtgaagaac    11760
cacacatttt ttgtgagagc aaatgtagat caaggcctct atgttttatc agggtgtggc    11820
ttctggtaga tcgcatcaac gcacccaggt aaagtatcag gcctcctgaa tgttggcttc    11880
aggcttcagt tctggaattg gttagtgcac ctgcatgccg ggggcgcggg gtggggtggg    11940
gtaaagtcca cagtgatgat tactctctaa tctctcttca gacagcgttc ttctcttgtt    12000
tactcgagtt acagttcctt attctgccta cggtttgcag ccttggagca cttttctacg    12060
tagctctcta agtctcttat cttcagagg acattgtcac agtgctctgt caacagtagc    12120
ggcggtcgct ccagaagatt aaaaattaaa acgataaact acccagagcc actttagatc    12180
aaatgggatt ggaaagtcag gttgcccatc cagcgtgcta cagtaagaaa cctttcaaat    12240
gatcctaata tttgctatag aaaaggaaac gaggtcgggc cggccaagct taaggaattc    12300
gctagcatgc atgttaacgg atccttaatt aatgtacagg gtcccgttta aacagtaacg    12360
ctagggataa cagggtaata taatcgagct gcaggattcg agggcccggg caggtcaatt    12420
ctaccgggta ggggaggcgc ttttcccaag gcagtctgga gcatgcgctt tagcagcccc    12480
gctgggcact tggcgctaca caagtggcct ctggcctcgc acacattcca catccaccgg    12540
taggcgccaa ccggctccgt tctttggtgg cccccttcgcg ccaccttcta ctcctcccct    12600
agtcaggaag ttccccccccg ccccgcagct cgcgtcgtgc aggacgtgac aaatggaagt    12660
```

```
agcacgtctc actagtctcg tgcagatgga cagcaccgct gagcaatgga agcgggtagg   12720 cctttgggc agcggccaat agcagctttg ctccttcgct ttctgggctc agaggctggg    12780
aaggggtggg tccgggggcg ggctcagggg cgggctcagg ggcggggcgg gcgcccgaag   12840
gtcctccgga ggcccggcat tctgcacgct caaaagcgc acgtctgccg cgctgttctc    12900
ctcttcctca tctccgggcc tttcgacctg cagccaatgc accgtccttg ccatcatggc   12960
ctcgtacccc ggccatcaac acgcgtctgc gttcgaccag gctgcgcgtt ctcgcggcca   13020
tagcaaccga cgtacggcgt tgcgccctcg ccggcagcaa gaagccacgg aagtccgccc   13080
ggagcagaaa atgcccacgc tactgcgggt ttatatagac ggtccccacg ggatggggaa   13140
aaccaccacc acgcaactgc tggtggccct gggttcgcgc gacgatatcg tctacgtacc   13200
cgagccgatg acttactggc gggtgctggg ggcttccgag acaatcgcga acatctacac   13260
cacacaacac cgcctcgacc agggtgagat atcggccggg gacgcggcgg tggtaatgac   13320
aagcgcccag ataacaatgg gcatgcctta tgccgtgacc gacgccgttc tggctcctca   13380
tatcgggggg gaggctggga gctcacatgc cccgccccg gccctcaccc tcatcttcga    13440
ccgccatccc atcgccgccc tcctgtgcta cccggccgcg cggtacccta tgggcagcat   13500
gaccccccag gccgtgctgg cgttcgtggc cctcatcccg ccgaccttgc ccggcaccaa   13560
catcgtgctt ggggcccttc cggaggacag acacatcgac cgcctggcca acgccagcg   13620 ccccggcgag cggctggacc tggctatgct ggctgcgatt cgccgcgttt acgggctact   13680
tgccaatacg gtgcggtatc tgcagtgcgg cgggtcgtgg cgggaggact ggggacagct   13740
ttcggggacg gccgtgccgc ccagggtgc cgagccccag agcaacgcgg gcccacgacc    13800
ccatatcggg gacacgttat ttaccctgtt tcggcccccc gagttgctgg cccccaacgg   13860
cgacctgtat aacgtgtttg cctgggcctt ggacgtcttg gccaaacgcc tccgttccat   13920
gcacgtcttt atcctggatt acgaccaatc gcccgccggc tgccgggacg ccctgctgca   13980
acttacctcc gggatggtcc agacccacgt caccaccccc ggctccatac cgacgatatg   14040
cgacctggcg cgcacgtttg cccgggagat gggggaggct aactgagggg atcgatccgt   14100
cctgtaagtc tgcagaaatt gatgatctat taaacaataa agatgtccac taaaatggaa   14160 gttttttcctg tcatactttg ttaagaaggg tgagaacaga gtacctacat tttgaatgga   14220
aggattggag ctacggggt gggggtggg tgggattaga taaatgcctg ctcttactg     14280 aaggctcttt actattgctt tatgataatg tttcatagtt ggatatcata atttaaacaa   14340
gcaaaaccaa attaagggcc agctcattcc tcccactcat gatctataga tctatagatc   14400
tctcgtggga tcattgttt tctcttgatt cccactttgt ggttctaagt actgtggttt    14460
ccaaatgtgt cagtttcata gcctgaagaa cgagatcagc agcctctgtt ccacatacac   14520
ttcattctca gtattgtttt gccaagttct aattccatca gaagctgact ctaggccgga   14580
cgcccgggcg accggccgag ctccaattcg ccctatagtg agtcgtatta caattcactg   14640
gccgtcgttt tacaacgtcg tgactgggaa accctggcg ttacccaact taatcgcctt    14700
gcagcacatc cccctttcgc cagctggcgt aatagcgaag aggcccgcac cgatcgccct   14760
tcccaacagt tgcgcagcct gaatggcgaa tgggacgcgc cctgtagcgg cgcattaagc   14820
gcggcgggtg tggtggttac gcgcagcgtg accgctacac ttgccagcgc cctagcgccc   14880
gctcctttcg ctttcttccc ttcctttctc gccacgttcg ccggctttcc ccgtcaagct   14940
ctaaatcggg ggtccccttt agggttccga tttagtgctt tacggcacct cgaccccaaa   15000
aaacttgatt agggtgatgg ttcacgtagt gggccatcgc cctgatagac ggtttttcgc   15060
```

```
cctttgacgt tggagtccac gttctttaat agtggactct tgttccaaac tggaacaaca    15120 ctcaaccota tctcggtcta ttcttttgat ttataaggga ttttgccgat ttcggcctat    15180
tggttaaaaa atgagctgat ttaacaaaaa tttaacgcga attttaacaa atatattaacg    15240 cttacaattt aggtggcact tttcggggaa atgtgcgcgg aaccctatt tgtttatttt     15300 tctaaataca ttcaaatatg tatccgctca tgagacaata accctgataa atgcttcaat    15360
aatattgaaa aggaagagt atgagtattc aacatttccg tgtcgccctt attcccttt      15420 ttgcggcatt ttgccttcct gtttttgctc acccagaaac gctggtgaaa gtaaaagatg    15480
ctgaagatca gttgggtgca cgagtgggtt acatcgaact ggatctcaac agcggtaaga    15540
tccttgagag ttttcgcccc gaagaacgtt ttccaatgat gagcactttt aaagttctgc    15600
tatgtggcgc ggtattatcc cgtattgacg ccgggcaaga gcaactcggt cgccgcatac    15660
actattctca gaatgacttg gttgagtact caccagtcac agaaaagcat cttacggatg    15720
gcatgacagt aagagaatta tgcagtgctg ccataaccat gagtgataac actgcggcca    15780
acttacttct gacaacgatc ggaggaccga aggagctaac cgcttttttg cacaacatgg    15840
gggatcatgt aactcgcctt gatcgttggg aaccggagct gaatgaagcc ataccaaacg    15900
acgagcgtga caccacgatg cctgtagcaa tggcaacaac gttgcgcaaa ctattaactg    15960
gcgaactact tactctagct tcccggcaac aattaataga ctggatggag gcggataaag    16020
ttgcaggacc acttctgcgc tcggcccttc cggctggctg gtttattgct gataaatctg    16080
gagccggtga gcgtgggtct cgcggtatca ttgcagcact ggggccagat ggtaagccct    16140
cccgtatcgt agttatctac acgacgggga gtcaggcaac tatggatgaa cgaaatagac    16200
agatcgctga gataggtgcc tcactgatta agcattggta actgtcagac caagtttact    16260
catatatact ttagattgat ttaaaacttc attttttaatt taaaaggatc taggtgaaga    16320
tcctttttga taatctcatg accaaaatcc cttaacgtga gttttcgttc cactgagcgt    16380
cagaccccgt agaaaagatc aaaggatctt cttgagatcc ttttttctg cgcgtaatct    16440 gctgcttgca acaaaaaaa ccaccgctac cagcggtggt ttgtttgccg atcaagagc     16500 taccaactct ttttccgaag gtaactggct tcagcagagc gcagatacca atactgtcc    16560 ttctagtgta gccgtagtta ggccaccact tcaagaactc tgtagcaccg cctacatacc    16620
tcgctctgct aatcctgtta ccagtggctg ctgccagtgg cgataagtcg tgtcttaccg    16680
ggttggactc aagacgatag ttaccggata aggcgcagcg gtcgggctga acggggggtt    16740
cgtgcacaca gcccagcttg gagcgaacga cctacaccga actgagatac ctacagcgtg    16800
agctatgaga aagcgccacg cttcccgaag ggagaaaggc ggacaggtat ccggtaagcg    16860
gcagggtcgg aacaggagag cgcacgaggg agcttccagg gggaaacgcc tggtatcttt    16920
atagtcctgt cgggtttcgc cacctctgac ttgagcgtcg atttttgtga tgctcgtcag    16980
gggggcggag cctatggaaa aacgccagca acgcggcctt tttacggttc ctggccttt    17040 gctggccttt tgctcacatg ttctttcctg cgttatcccc tgattctgtg ataaccgta    17100 ttaccgcctt tgagtgagct gataccgctc gccgcagccg aacgaccgag cgcagcgagt    17160
cagtgagcga ggaagcggaa gagcgcccaa tacgcaaacc gcctctcccc gcgcgttggc    17220
cgattcatta atgcagctgg cacgacaggt ttcccgactg gaaagcgggc agtgagcgca    17280
acgcaattaa tgtgagttag ctcactcatt aggcacccca ggctttacac tttatgcttc    17340
cggctcgtat gttgtgtgga attgtgagcg ataacaatt tcacacagga aacagctatg    17400
```

```
accatgatta cgccaagctc gaaattaacc ctcactaaag ggaacaaaag ctgtcgagat    17460
ctagatatcg atggccatag                                                17480
```

<210> SEQ ID NO 4
<211> LENGTH: 20
<212> TYPE: DNA
<213> ORGANISM: Artificial Sequence
<220> FEATURE:
<223> OTHER INFORMATION: Probe 5e2

<400> SEQUENCE: 4

```
gccgcactat ttgcagcatg                                                   20
```

<210> SEQ ID NO 5
<211> LENGTH: 22
<212> TYPE: DNA
<213> ORGANISM: Artificial Sequence
<220> FEATURE:
<223> OTHER INFORMATION: Primer 1472_23

<400> SEQUENCE: 5

```
cgttactatc catcacctaa gc                                                22
```

<210> SEQ ID NO 6
<211> LENGTH: 22
<212> TYPE: DNA
<213> ORGANISM: Artificial Sequence
<220> FEATURE:
<223> OTHER INFORMATION: Primer 1472_24

<400> SEQUENCE: 6

```
gggaattcag ctgtgtctga ac                                                22
```

<210> SEQ ID NO 7
<211> LENGTH: 20
<212> TYPE: DNA
<213> ORGANISM: Artificial Sequence
<220> FEATURE:
<223> OTHER INFORMATION: Primer 1260_1

<400> SEQUENCE: 7

```
gagactctgg ctactcatcc                                                   20
```

<210> SEQ ID NO 8
<211> LENGTH: 21
<212> TYPE: DNA
<213> ORGANISM: Artificial Sequence
<220> FEATURE:
<223> OTHER INFORMATION: Primer 1260_2

<400> SEQUENCE: 8

```
ccttcagcaa gagctgggga c                                                 21
```

<210> SEQ ID NO 9
<211> LENGTH: 20
<212> TYPE: DNA
<213> ORGANISM: Artificial Sequence
<220> FEATURE:
<223> OTHER INFORMATION: Primer PRRS7

<400> SEQUENCE: 9

```
atcaaggaat cttgggagca                                                   20
```

```
<210> SEQ ID NO 10
<211> LENGTH: 17
<212> TYPE: DNA
<213> ORGANISM: Artificial Sequence
<220> FEATURE:
<223> OTHER INFORMATION: Actin forward primer

<400> SEQUENCE: 10
cggaaccgcy cattggc                                                17

<210> SEQ ID NO 11
<211> LENGTH: 20
<212> TYPE: DNA
<213> ORGANISM: Artificial Sequence
<220> FEATURE:
<223> OTHER INFORMATION: Actin backward primer

<400> SEQUENCE: 11
acccacactg tgcccatcta                                             20
```

BOROPEPTIDE INHIBITORS OF ENTEROPEPTIDASE AND THEIR USES IN TREATMENT OF OBESITY, OVERWEIGHT AND/OR DISEASES ASSOCIATED WITH AN ABNORMAL FAT METABOLISM

FIELD OF THE INVENTION

The present invention relates to novel non-absorbable oligopeptides based on boroanalogs of amino acids incorporating a protonatable function on their side chain, such as boroarginine, borolysine, boroornithine, and related compounds, that selectively modulate, regulate, and/or inhibit enteropeptidase. These compounds are used individually, in combination or in association with other known compounds for the treatment of excess weight, obesity and diseases associated with an abnormal fat metabolism.

BACKGROUND AND RELATED PRIOR ART

Obesity is a multi-faceted chronic condition and is the most prevalent nutritional problem in the United States today. Obesity, a condition caused by an excess of energy intake as compared to energy expenditure, contributes to the pathogenesis of hypertension, type II or non-insulin dependent diabetes mellitus, hypercholesterolemia, hyperlipidemia, hypertriglyceridemia, heart disease, pancreatitis, and such common forms of cancer such as breast cancer, prostate cancer, uterine cancer and colon cancer.

At present, only a limited number of drugs for treating obesity are commercially available. Unfortunately, while some of these drugs may bring short-term relief to the patient, a long-term successful treatment has not yet been achieved. Exemplary methods of treating obesity are also disclosed in U.S. Pat. Nos. 3,867,539; 4,446,138; 4,588,724; 4,745,122; 5,019,594; 5,300,298; 5,403,851; 5,567,714; 5,573,774; 5,578,613; and 5,900,411.

One of the presently available drugs for treating obesity, developed by Hoffman-LaRoche, is an inhibitor of pancreatic lipase (PL). Pancreatic lipase is responsible for the degradation of triglycerides to monoglycerides. However, it has been associated with side-effects such as severe diarrhea resulting in absorption inhibition of only one specific fraction of fatty acids and, has been known to induce allergic reactions. Treatment with PL inhibitors is thus highly disadvantageous and may even expose the treated subject to life-threatening risks.

Recently, it has been suggested that fat absorption may be reduced by inhibiting the activity of the microsomal triglyceride-transfer protein (MTP), which is involved in the formation and secretion of very light density lipoproteins (VLDL) and chylomicrons. Sharp et al., [Nature (1993) 365:65-69] and Wetterau et al., [Science (1994) 282:751-754,] demonstrated that the mtp gene is responsible for abetalipoproteinemia disease. U.S. Pat. Nos. 6,066,650, 6,121,283 and 6,369,075 describe compositions that include MTP inhibitors, which are aimed at treating various conditions associated with excessive fat absorption. However, patients treated with MTP inhibitors suffer major side effects including hepatic steatosis, which are attributed to reduced MTP activity in both intestine and liver. This is not surprising since people naturally deficient for MTP activity were shown to develop fatty livers [Kane and Havel (1989); Disorders of the biogenesis and secretion of lipoproteins containing the apolipoprotein B. pp. 1139-1164 in: "The metabolic basis of inherited disease" (Scrivers et al., eds.). McGraw-Hill, New York]. In fact, the company Brystol Myers Squibb, that developed MTP inhibitors for the treatment of obesity, has recently decided to abandon this target, due to this fatty liver side effect.

The presently known targets for the treatment of obesity and related disorders can be divided into four main classes: (i) appetite blockers, which include for example the NPY (neuropeptide Y); (ii) satiety stimulators, which include, for example, the product of the ob, db and agouti genes; (iii) energy or fatty acid burning agents, which include the UCPs (Uncoupling Proteins); and (iv) fat absorption inhibitors such as those acting on PL and MTP in the intestine, described above.

As discussed herein, the use of these targets is highly limited by their redundancy, their multiple targeting and/or their lack of tissue specificity.

There is thus a widely recognized need for, and it would be highly advantageous to have compositions and methods for treating obesity and related diseases and disorders devoid of the above limitations.

Serine proteases are involved in a large number of important physiological processes. Selective inhibition of a given serine protease is one of the strategies for the treatment of pathological conditions associated with the activity or overactivity of these serine proteases. Below is a non-exhaustive list of serine protease inhibitors disclosed in the literature:

phosphorus-based inhibitors such as the diisopropylphosphofuloridate (DFP) (Jansen et al., (1952) Adv. Enzymol. 13: 321-343) or diphenyl phosphonate ester analogues;

fluorine-containing serine proteases, such as trifluoromethyl ketones (TFMKs);

peptide-based aldehydes, chloromethyl ketones, fluoromethyl ketones, dimethyl sulphonium salts, α-keto-acids and amides, α-keto esters and α-keto-aldehydes (glyoxals);

natural products such as the cyclotheonamides, derived from the Japanese marine sponge *Theonella* sp.;

molecules based on heterocyclic structure;

N-hydroxysuccimide heteorcycles and related compounds;

isocoumarins such as 3,4-dichloroisocoumarin;

β lactam-based inhibitors;

metal-potentiated compounds;

aprotinin (Trasylol®), used to reduce bleeding; and serpins (serine protease inhibitors) such as antithrombin and α-1-antitrypsin having a role in coagulation/thrombosis and emphysema/A1AT respectively.

However, few compounds have been described as serine protease inhibitors with a specific and selective inhibition of a unique target. Moreover, no compounds have been disclosed or suggested, to selectively and specifically inhibit the enteropeptidase, and to be used in the treatment of obesity, excess weight or diseases associated with an abnormal fat metabolism.

Enteropeptidase is a serine protease situated on the surface of epithelial intestinal cells (enterocytes) (Lancet. 1969 Apr. 19; 1(7599):812-3; Am J Physiol Gastrointest Liver Physiol. 2003 December; 285(6):G1235-41; Proc Soc Exp Biol Med. 1994 June; 206(2):114-8; Ciba Found Symp. 1979 Jan. 16-18; (70):169-87; Lancet. 1982 Aug. 28; 2(8296):504). The substrate of enteropeptidase is trypsinogen, a precursor to trypsin. Enteropeptidase converts trypsinogen into a molecule of trypsin. In turn, trypsin, which is also a serine protease, converts the precursors of a series of digestive enzymes, such as procarboxypeptidases A and B, chymotrypsinogen, pancreatic prolipase and proelastase, into the active forms of the enzymes (carboxypeptidases A and B, chymotrypsin, pancreatic lipase and elastase). The latter active forms of such digestive enzymes are required for the processing and ultimate absorption of protein and fat matter in the gastrointestinal (GI) tract.

Because enteropeptidase is located in the intestinal lumen, inhibition of this enzyme requires that the compounds selectively inhibit enteropeptidase without interfering with circulating serine proteases, such as thrombin, kalikrein, and the like.

Thus, there is a need for compounds to treat obesity, excess overweight as well as diseases associated with an abnormal fat metabolism, on a long term basis that have a specific target.

It is an object of the present invention to provide compounds that inhibit enteropeptidase, and more particular that selectively inhibit enteropeptidase. In particular, these compounds are non-absorbable i.e., they do not pass from the intestine into the blood.

It is another object of the present invention to provide compounds that are derivatives of boroanalogs of amino acids incorporating a protonatable functionality on their side chain, such as borolysine, boroornithine, boroarginine and the like, and are strong, non-absorbable inhibitors of enteropeptidase.

Yet another object of the invention, are compositions, especially pharmaceutical compositions, comprising at least one of the compounds disclosed in the present invention.

It is also another object of the invention to provide methods to treat obesity, excess weight or diseases associated with an abnormal fat metabolism, comprising administrating, to a mammal in need thereof, at least one of the compounds disclosed in the present invention or a composition described in the present invention.

Yet another object of the present invention is the use of at least one of the compounds or of the composition disclosed herein, for the treatment of obesity, excess weight and diseases associated with an abnormal fat metabolism. A compound or a composition of the invention for use in the treatment of obesity, excess weight and diseases associated with an abnormal fat metabolism, is also provided.

These and other objects are achieved by the present invention as evidence by the summary of the invention, description of the preferred embodiments and the claims.

SUMMARY OF THE INVENTION

In one aspect, the invention relates to a compound having the following formula (I):

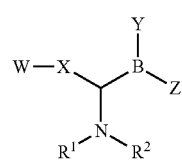

I wherein
B represents a boron atom;
W is a nitrogen-containing functionality group, sustaining a positive charge either through protonation or quaternization, this group being selected from:
(i) an amino group of the formula:

wherein $G^1$ and $G^2$ are, independently, H, or linear or branched or cyclic alkyl groups containing from 1 to 10 carbon atoms, or branches of a ring system that incorporates the N atom and that contains a total of up to 15 atoms;
(ii) a quaternary ammonium group of formula:

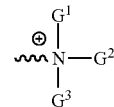

wherein $G^1$, $G^2$ and $G^3$ are, independently, H, or linear or branched or cyclic alkyl groups containing from 1 to 10 carbon atoms, or branches of a ring system that incorporates the N atom and that contains a total of up to 15 atoms; or
(iii) a guanidine group of formula:

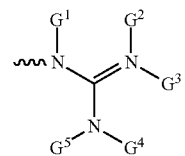

wherein $G^1$, $G^2$, $G^3$, $G^4$ and $G^5$ are, independently, H, or linear or branched or cyclic alkyl groups containing from 1 to 10 carbon atoms, or branches of a ring system that incorporates one or more of the guanidine N atoms and that contains a total of up to 15 atoms;
X is a linker unit having the formula $(CX^1X^2)_p$, wherein $1<p<10$, and wherein $X^1$ and $X^2$ are, independently, H, or linear or branched alkyl groups containing from 1 to 10 carbon atoms, or branches of a ring residue containing from 3 to 10 atoms;
Y is an OH, or is an OR group wherein R is a linear, branched or cyclic alkyl group incorporating from 1 to 10 carbon atoms, or is a branch of a homocyclic or heterocyclic structure which incorporates the B atom and which contains up to 20 atoms chosen from C, O, N, and S atoms;
Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;
R1 is chosen among:
(i) an aminoacyl residue derived from an amino acid.
(ii) a derivative of the foregoing aminoacyl residue in which the amino group is additionally acylated, or sulfonylated, or phosphorylated to form an amide, or peptide, or sulfonamide, or phosphoramide bond;
(iii) an acyl group of general formula R'—CO, wherein R' is:
 a. a linear, branched or cyclic alkyl group that contains from 1 to 10 C atoms;
 b. a saturated heterocyclic ring incorporating up to 20 atoms chosen from C, O, N, and S atoms;
 c. an aryl group selected from phenyl or a substituted variant thereof bearing any combination, at any one ring position, of one or more substituents selected from halogen, alkyl groups containing from 1 to 10 carbon atoms, trifluoromethyl and alkoxy groups; or
d. a heteroaryl group;
R² is either H, or a linear or branched or cyclic alkyl group containing from 1 to 10 carbon atoms, or an OR group wherein R may be H or a linear or branched or cyclic alkyl group containing from 1 to 10 carbon atoms.

In another aspect, the invention also concerns a compound having the formula II.

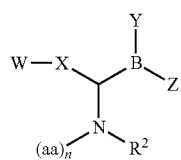

II wherein
B represents a boron atom;
W is a nitrogen-containing functionality group, sustaining a positive charge either through protonation or quaternization, this group being selected from:
(i) an amino group of the formula:

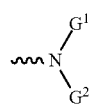

wherein G¹ and G² are, independently, H, or linear or branched or cyclic alkyl groups containing from 1 to 10 carbon atoms, or branches of a ring system that incorporates the N atom and that contains a total of up to 15 atoms;
(ii) a quaternary ammonium group of formula:

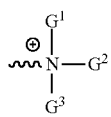

wherein G¹, G² and G³ are, independently, H, or linear or branched or cyclic alkyl groups containing from 1 to 10 carbon atoms, or branches of a ring system that incorporates the N atom and that contains a total of up to 15 atoms; or
(iii) a guanidine group of formula:

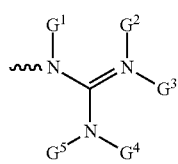

wherein G¹, G², G³, G⁴ and G⁵ are, independently, H, or linear or branched or cyclic alkyl groups containing from 1 to 10 carbon atoms, or branches of a ring system that incorporates one or more of the guanidine N atoms and that contains a total of up to 15 atoms;
X is a linker unit having the formula $(CX^1X^2)_p$, wherein $1<p<10$, and wherein $X^1$ and $X^2$ are, independently, H, or linear or branched alkyl groups containing from 1 to 10 carbon atoms, or branches of a ring residue containing from 3 to 10 atoms;
Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;
Z is an OH, or an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;
R² is either H, or a linear or branched or cyclic alkyl group containing from 1 to 10 carbon atoms; or an OR group, wherein R may be H or a or a linear or branched or cyclic alkyl group containing from 1 to 10 carbon atoms; and
"aa" refers to any amino acyl residue or derivative thereof, and n is at least two.

In a yet another aspect, the invention is directed to the following compounds having formula (III) or (IV):

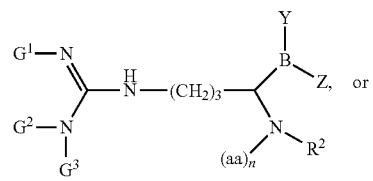

III

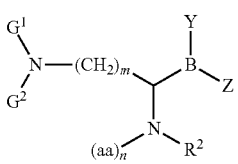

IV wherein:
B represents a boron atom;
Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;
Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;
R² is either H, or a linear or branched or cyclic alkyl group containing from 1 to 10 carbon atoms or an OR group wherein R may be H or a linear or branched or cyclic alkyl group containing from 1 to 10 carbon atoms;

G¹, G² and G³ or G¹ and G² are, independently, H, or linear or branched or cyclic alkyl groups containing from 1 to 10 carbon atoms, or branches of a ring system that incorporates one or more of the guanidine N atoms and that contains a total of up to 15 atoms;

"aa" refers to any amino acid residue or derivative thereof, and n is at least two; and the index, m, equals 3 or 4.

In another aspect, the invention also concerns a pharmaceutical composition comprising at least one compound as described above.

In a last aspect, the invention also refers to a method comprising administering to a mammal in need of said treatment, at least one compound or a composition of the invention for treating a patient having obesity, having excess weight or suffering from abnormal fat metabolism.

BRIEF DESCRIPTION OF THE DRAWINGS

FIG. 5 is a Table showing the IC 50 (in nM) of enteropeptidase, various serine proteases and other enzyme families, in the presence of compounds OBE 1999, OBE 2000, OBE 2001 or OBE 2002.

FIGS. 6A-6E represent the nucleotide and protein sequences of the human enteropeptidase (PRSS7). The first line indicates the nucleotide sequence, grouped by codons; the second line indicates the amino acid sequence corresponding to the above codons with the three-letter code. The first codon of translation and the stop codon are shown in bold. Numbering of the nucleic acid is at the right end of the first line, and numbering of the amino acids is indicated under amino acid residue (third line).

FIGS. 7A-E represent examples of processes to synthesize the compounds of the invention. (FIG. 7A): example of a process for the synthesis of the Acetyl-Ala-Phe-BoroLysine (*pin: pinandiol group); (FIG. 7B and FIG. 7C): first example of a process for the synthesis of the Acetyl-Ala-Phe-BoroArginine; (FIG. 7D): second example of a process for the synthesis of the Acetyl-Ala-Phe-BoroArginine; this second process also enables the synthesis of the Acetyl-Ala-Phe-BoroOrnithine (compound 8), since Acetyl-Ala-Phe-BoroOrnithine is an intermediate compound in the synthesis of Acetyl-Ala-Phe-BoroArginine by this process; (FIG. 7E): synthesis of the Acetyl-Ala-Phe-OH group, to be inserted in step 10 of the process in FIG. 7C or in step 7 of the process in FIG. 7D.

FIGS. 12B-G represent the 17,480 bp nucleotide sequence of this vector.

FIG. 13 is the Afill restriction map of the wild type enteropeptidase allele (above) and the knockout (KO) enteropeptidase allele (below).

FIGS. 18A-B represent the nucleotide and protein sequences of human trypsin.

DESCRIPTION OF THE PREFERRED EMBODIMENTS OF THE INVENTION

Figure 1:
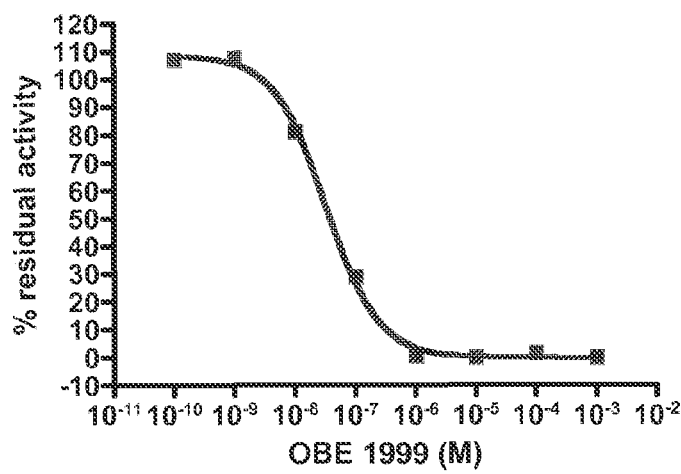
FIG. 1 is a graph showing the activity of the enteropeptidase according to increasing concentrations of compound OBE 1999.
Figure 2:
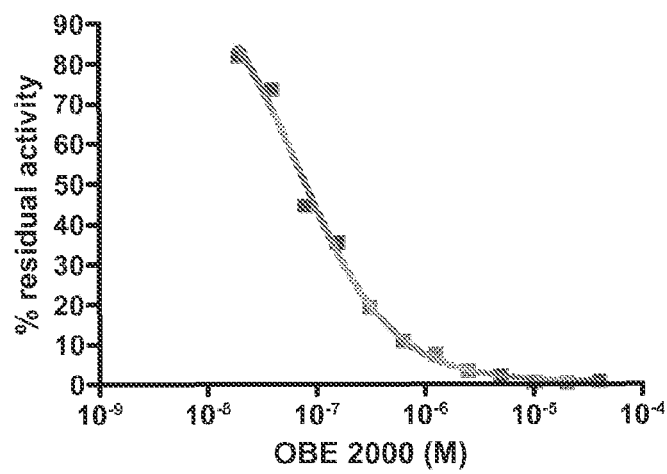
FIG. 2 is a graph showing the activity of the enteropeptidase according to increasing concentrations of compound OBE 2000.
Figure 3:
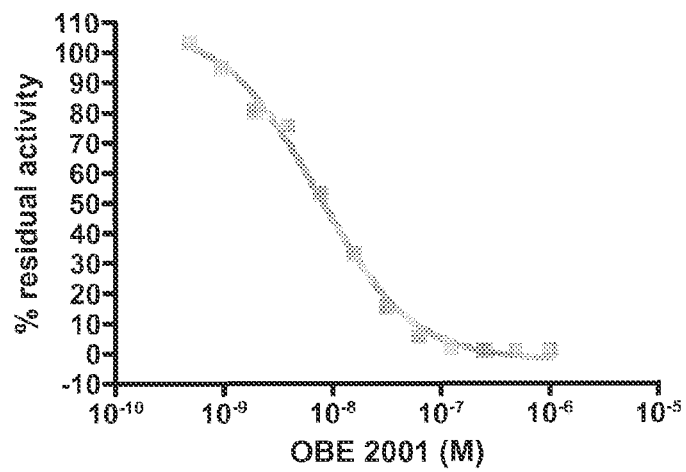
FIG. 3 is a graph showing the activity of the enteropeptidase according to increasing concentrations of compound OBE 2001.
Figure 4:
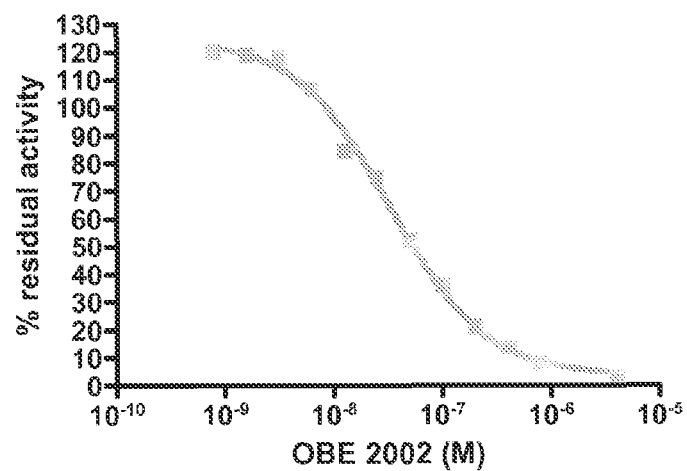
FIG. 4 is a graph showing the activity of the enteropeptidase according to increasing concentrations of compound OBE 2002.

As used herein the term "protecting group" means a chemical group used to modify the compound of the invention, in one of its functional groups, in order to obtain in a subsequent chemical reaction and to avoid unwanted reactions. Examples of protecting groups are as follows:

Alcohol protecting groups: Acetyl (Ac), β-Methoxyethoxymethyl ether (MEM), Methoxymethyl ether (MOM), p-Methoxybenzyl ether (PMB), Methylthiomethyl ether, Pivaloyl (Piv), Tetrahydropyran (THP), Silyl ether (most popular ones include trimethylsilyl (TMS), tert-butyldimethylsilyl (TBDMS), and triisopropylsilyl (TIPS) ethers) and methyl ethers;

Amine protecting groups: Acetyl (Ac), Benzoyl (Bz), Pivaloyl (Pv) Methanesulfonyl (Ms), Benzenesulfonyl (PhSO$_2$), para-Toluenesulfonyl (Ts), Phosphoryl [(HO)$_2$P(O)], Dibenzyloxyphosphoryl [(BnO)$_2$P(O)], Benzyloxy-methanephosphonyl [(CH$_3$)(BnO)P(O)], Carbobenzyloxy (Cbz) group, tert-Butyloxycarbonyl (BOC) group, 9-Fluorenylmethyloxycarbonyl (FMOC) group, Benzyl (Bn) group and p-methoxyphenyl (PMP) group;

Carbonyl protecting groups: Acetals and Ketals, Acylals and Dithianes; and

Carboxylic acid protecting groups: Methyl esters, Benzyl esters, tert-Butyl esters and Silyl esters.

"Chemoselectivity" as used herein means the preferential outcome of one instance of a generalized reaction over a set of other plausible reactions.

"An amino acid residue" is defined in the present invention as one of the following 21 amino acid acyl residues: glycine, alanine, valine, leucine, isoleucin, phenylalanine, tyrosine, tryptophan, methionine, cystine, cysteine, serine, threonine, histidine, aspartic acid, glutamic acid, asparagine, glutamine, lysine, arginine and proline.

A "derivative of an amino acid residue" means an amino acid residue as defined in the previous paragraph, for which the amino group is additionally acylated, or sulfonylated, or phosphorylated to form an amide, or carbamate, or urea, or N-substituted urea, or peptide, or sulfonamide, or phosphoramide bond. Additionally, the amino group may be further substituted with a small alkyl group containing from 1 to 5 C atoms. Particular derivatives of amino acids are exemplified by, but not limited to, the following representative structures, (i)-(iii), wherein the wavy line represents the bond that connects these structures to the other part of the molecule:

structural type (i)

| $R^1$ | $R^2$ | $R^3$ | name |
|---|---|---|---|
| $CH_3$ | $CH_3$ | H | N-acetylalanyl |
| $CH_3$ | $CH_3$ | $CH_3$ | N-methyl-N-acetylalanyl |
| $CH_3$ | $(CH_2)_2COOH$ | H | N-acetylglutamyl |
| $CH_3$ | $CH-C_6H_5$ | H | N-acetylphenylalanyl |
| $(CH_3)_3C$ | $CH_3$ | $CH_3$ | N-methyl-N-pivaloylalanyl |
| $C_6H_5$ | $(CH_2)COOH$ | H | N-benzoylglutamyl |
| $4\text{-}Cl\text{-}C_6H_4$ | $(CH_2)COOH$ | H | N-(4-chlorobenzoyl)glutamyl |
| $OCH_2C_6H_5$ | $CH_3$ | H | N-(carbobenzyloxy)alanyl |
| $NH_2$ | $CH-C_6H_5$ | H | N-(carbamoyl)phenylalanyl |
| $N(CH_2CH_3)_2$ | $CH_3$ | H | N-(diethylcarbamoyl)alanyl | structural type (ii)

| $R^1$ | $R^2$ | $R^3$ | name |
|---|---|---|---|
| $CH_3$ | $CH_3$ | H | N-methanesulfonylalanyl |
| $CH_3$ | $CH_3$ | $CH_3$ | N-methyl-N-methanesulfonylalanyl |
| $4\text{-}CH_3\text{-}C_6H_4$ | $(CH_2)_2COOH$ | H | N-p-toluenesulfonylglutamyl |
| $CH_3$ | $CH-C_6H_5$ | H | N-methansulfonylphenylalanyl |
| $C_6H_5$ | $CH_3$ | $CH_3$ | N-methyl-N-benzenesulfonylalanyl | structural type (iii)

| $R^1$ | $R^2$ | $R^3$ | $R^4$ | name |
|---|---|---|---|---|
| OH | OH | $CH_3$ | H | N-phosphorylalanyl |
| $OCH_2C_6H_4$ | $OCH_2C_6H_4$ | $CH_3$ | H | N-(dibenzyloxyphosphoryl)alanyl |
| $OCH_2C_6H_4$ | $OCH_2C_6H_4$ | $CH_3$ | $CH_3$ | N-methyl-N-(dibenzyloxyphosphoryl)alanyl |
| $CH_3$ | OH | $CH_3$ | H | N-(methanephosphonyl)alanyl |

The expression "pharmaceutically acceptable salt" means an acid salt or a basic salt that is suitable or compatible with the treatment of the subject.

By "inhibition of the activity of the enteropeptidase", is meant that a decrease of 50% of the in vitro activity of the enteropeptidase is obtained, with a concentration of the compound of the invention that is less than 10 µM, less than 1 µM, less than 100 nM, less than 10 nM or less than 1 nM, for 1 nM of enteropeptidase. Said concentration can be determined as described in details in point 2.1. below, and particularly using Np Tosyl Gly Pro Arg pNa as a substrate.

The expression "specific inhibition of the trypsin-like serine protease" refers to the inhibition of proteases from the serine protease family and more particularly to serine protease of the trypsin-like subtype only. In contrast, the activity of other proteases such as cysteine peptidases, aspartate peptidases, metallo-proteases, lipases and/or glucosidases are not altered by the compound of the invention. In another embodiment, in combination with the previous one, the activity of chymotrypsin-like serine proteases is not altered by compound of the invention.

The expression "selective inhibition of the enteropeptidase" refers to the inhibition of the enteropeptidase only (in vivo), whereas the activity of other proteases from the same subtype (trypsin-like subtype) are not altered by the compounds of the invention. This distinction between the specificity and selectivity has been rendered possible by the fact that the compounds of the invention are non-absorbable and therefore the inhibition is limited to the enteropeptidase whose location is intestinal.

The determination of the $IC_{50}$ of the compounds of the invention on enteropeptidase or on other serine protease may be tested in vitro as described in the examples below.

The term "treatment" as used herein refers not only to the loss of weight of the mammal following the administration of at least one compound or the composition of the invention, but also to the maintenance of the weight such that there is no weight increase.

The term "mammal" encompasses any of various warm-blooded vertebrate animals of the class Mammalia, including humans, characterized by a covering of hair on the skin and, in the female, milk-producing mammary glands for nourishing the young.

"Pharmaceutically acceptable vehicles or carriers" encompass any substance that enables the formulation of the compounds of the invention within a composition. A vehicle is any substance or combination of substance physiologically acceptable i.e., appropriate for its use in a composition in contact with a mammal, and thus non-toxic. Examples of such vehicles are phosphate buffered saline solutions, distilled water, emulsions such as an oil/water emulsions, various types of wetting agents sterile solutions and the like.

"Obesity" is in general defined in human by at least 20% over the average weight for the person's age, sex and height. Obesity is defined by a body mass index (BMI=kg/m$^2$) over 30. Obesity can also be defined by absolute waist circumference (>102 cm in men and >88 cm in women) or Waist-to-hip ratio (WHR) (WHR more than 0.7 for women and more than 0.9 for men). "Excessive weight" is defined by a BMI that is comprised between 25 and 29.9.

More specifically, in a first embodiment, the present invention relates to compounds having an inhibitory activity on the enzymatic activity of enteropeptidase. In another aspect, compounds are provided that have a selective inhibitory activity on the enzymatic activity of enteropeptidase.

The compounds of the invention have the following formula I:

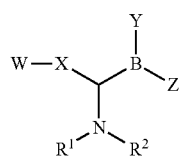

wherein:
B represents a boron atom;
W is a nitrogen-containing functionality group, sustaining a positive charge either through protonation or quaternization, this group being selected from:
(i) an amino group having the formula:

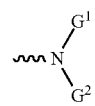

wherein $G^1$ and $G^2$ are, independently, H, or linear or branched or cyclic alkyl groups containing from 1 to 10 carbon atoms, or branches of a ring system that incorporates the N atom and that contains a total of up to 15 atoms.
(ii) a quaternary ammonium group having the formula:

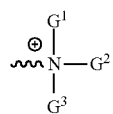

wherein $G^1$, $G^2$ and $G^3$ are, independently, H, or linear or branched or cyclic alkyl groups containing from 1 to 10 carbon atoms, or branches of a ring system that incorporates the N atom and that contains a total of up to 15 atoms;
(iii) a guanidine group having the formula:

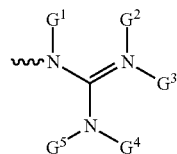

wherein $G^1$, $G^2$, $G^3$, $G^4$ and $G^5$ are, independently, H, or linear or branched or cyclic alkyl groups containing from 1 to 10 carbon atoms, or branches of a ring system that incorporates one or more of the guanidine N atoms and that contains a total of up to 15 atoms;
X is a linker unit having the formula $(CX^1X^2)_p$, wherein 1<p<10, and wherein $X^1$ and $X^2$ are, independently, H, or linear or branched alkyl groups containing from 1 to 10 carbon atoms, or branches of a ring residue containing from 3 to 10 atoms.
Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;
Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;
R1 is selected from:
(i) an aminoacyl residue derived from an amino acid.
(ii) a derivative of the foregoing aminoacyl residue in which the amino group is additionally acylated, or sulfonylated, or phosphorylated to form an amide, or peptide, or sulfonamide, or phosphoramide bond;
(iii) an acyl group of general formula R'—CO, wherein R' is:
  a. a linear, branched or cyclic alkyl group that contains from 1 to 10 C atoms;
  b. a saturated heterocyclic ring incorporating up to 20 atoms chosen from C, O, N, and S atoms;
  c. an aryl group selected from phenyl or a substituted variant thereof bearing any combination, at any one ring position, of one or more substituents selected from halogen, alkyl groups containing from 1 to 10 carbon atoms, trifluoromethyl and alkoxy groups; or
  d. a heteroaryl group.

For compounds of formula (I) above, examples of a heteroaryl group ($R^1$) is a 2,3, or 4-pyridyl group, which may additionally bear any combination of one or more substituents such as halogen, alkyl groups containing from 1 to 10 carbon atoms, trifluoromethyl, alkoxy, alkylthio, alkylsulfonyl, etc. Similarly, examples of a five-membered ring aromatic heterocyclic group ($R^1$) are 2-thienyl, 3-thienyl, 2-thiazolyl, 4-thiazolyl and 5-thiazolyl groups. These groups may additionally bear any combination of one or more substituents such as halogen, an alkyl group containing from 1 to 10 carbon atoms, trifluoromethyl, alkoxy, alkylthio, alkylsulfonyl, etc.

In another embodiment, the present invention relates to the compound having the formula II:

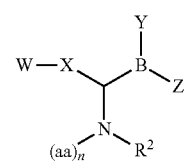

wherein
B represents a boron atom;
W is a nitrogen-containing functionality group, sustaining a positive charge either through protonation or quaternization, this group being selected from:
(i) an amino group having the formula:

wherein $G^1$ and $G^2$ are, independently, H, or linear or branched or cyclic alkyl groups containing from 1 to 10 carbon atoms, or branches of a ring system that incorporates the N atom and that contains a total of up to 15 atoms;

(ii) a quaternary ammonium group having the formula:

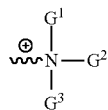

wherein $G^1$, $G^2$ and $G^3$ are, independently, H, or linear or branched or cyclic alkyl groups containing from 1 to 10 carbon atoms, or branches of a ring system that incorporates the N atom and that contains a total of up to 15 atoms;

(iii) a guanidine group having the formula:

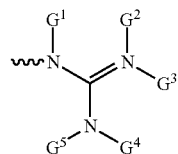

wherein $G^1$, $G^2$, $G^3$, $G^4$ and $G^5$ are, independently, H, or linear or branched or cyclic alkyl groups containing from 1 to 10 carbon atoms, or branches of a ring system that incorporates one or more of the guanidine N atoms and that contains a total of up to 15 atoms;

X is a linker unit having the formula $(CX^1X^2)_p$, wherein $1<p<10$, and wherein $X^1$ and $X^2$ are, independently, H, or linear or branched alkyl groups containing from 1 to 10 carbon atoms, or branches of a ring residue containing from 3 to 10 atoms;

Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;

Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;

$R^2$ is either H, or a linear or branched or cyclic alkyl group containing from 1 to 10 carbon atoms, or an OR group wherein R may be H or a linear or branched or cyclic alkyl group containing from 1 to 10 carbon atoms; and "aa" refers to any amino acyl residue or derivative thereof, and n is at least two, or in another embodiment n is between 2 and 20, in another embodiment between 2 and 15, in another embodiment between 2 and 10, and in another embodiment between 2 and 5.

With respect to the compounds of formula (II), in another aspect, n is 2, 3 or 4. The at least two amino acid residues are selected among the following: Ala, Arg, Asn, Asp, Cys, Cystine, Glu, Gln, Gly, His, Ile, Leu, Lys, Met, Phe, Pro, Ser, Thr, Trp, Tyr and Val.

In the case where n=2, a combination of amino acid residues is Tyr and Pro, Ala and Phe, Arg and Glu, Glu and Gly, Trp and Glu, Thr and Pro, and Leu and Leu.

In the case where n=3, a combination of amino acid residues is Phe, Arg and Val, Arg, Cys and Thr, Gly, Cys and Pro, Gly, Cys and Asn and Lys, Gly and Asp.

In yet another embodiment, the amino group of the first N-terminal amino acid residue bears a protecting group selected from the group of acyl, sulfonyl, or phosphoryl, as specified on page 10, and it may further bear an alkyl group containing from 1 to 5 C atoms, as indicated in the table that appears on page 11.

In yet another embodiment, the amino group of the first N-terminal amino acid residue can be derivatized with an acyl, sulfonyl, or phosphoryl group to form an amide, or carbamate, or urea, or N-substituted urea, or peptide, or sulfonamide, or phosphoramide bond, and it may be further substituted with a small alkyl group containing from 1 to 5 C atoms, as indicated in the table that appears on page 11.

With respect to the compounds of formula (I) or (II) as defined above:

When $G^1$ to $G^5$ are, independently, branches of a ring system that incorporates the N atom and that contains a total of up to 15 atoms, these 15 atoms include any permutation of carbon, oxygen, nitrogen, and sulfur atoms, Examples of ring residues for the amino group (W) are pyrrolidine, piperidine, morpholine, thiomorpholine, piperazine, and N-methylpiperazine. Representative embodiments are as follows:

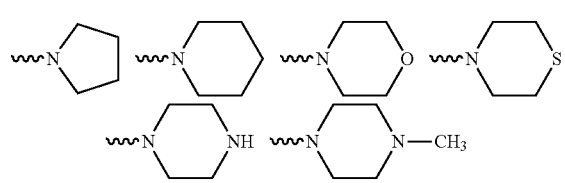

Examples of $G^1$ and $G^2$ for the amino group (W) are the following: hydrogen, methyl, ethyl, propyl, isopropyl, cyclopropyl, butyl, isobutyl, tert-butyl, cyclobutyl, pentyl, cyclopentyl, hexyl, cyclohexyl, phenyl, etc. Representative embodiments are as follows:

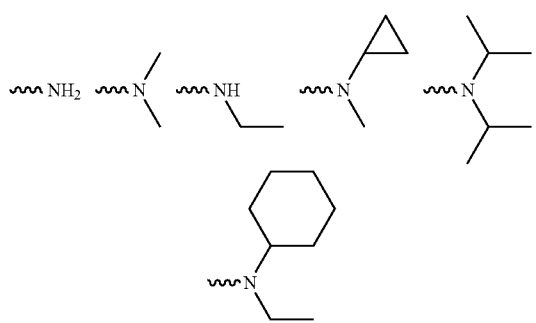

Examples of ring residues for the quaternary ammonium group (W) are pyrrolidine, piperidine, morpholine, thiomorpholine, piperazine, and N-methylpiperazine. Representative embodiments are as follows:

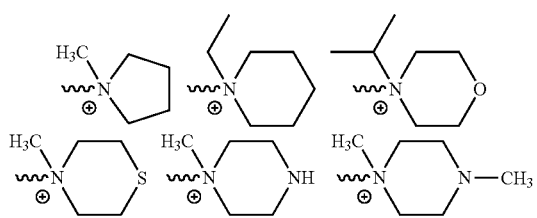

Examples of G¹, G² and G³ for the quaternary ammonium group (W) are the following: methyl, ethyl, propyl, isopropyl, cyclopropyl, butyl, isobutyl, tert-butyl, cyclobutyl, pentyl, cyclopentyl, hexyl, cyclohexyl, phenyl, etc, Representative embodiments are as follows:

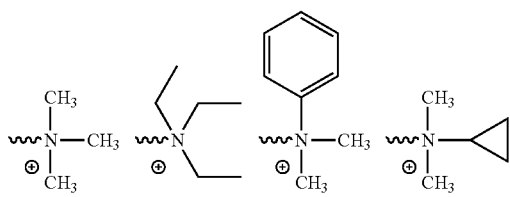

Examples of ring residues for the guanidine group (W) are pyrrolidine, piperidine, morpholine thiomorpholine, piperazine, N-methylpiperazine, and tetrahydropyrimidine. In addition, G² may also be a lone pair of electrons. Representative embodiments are as follows.

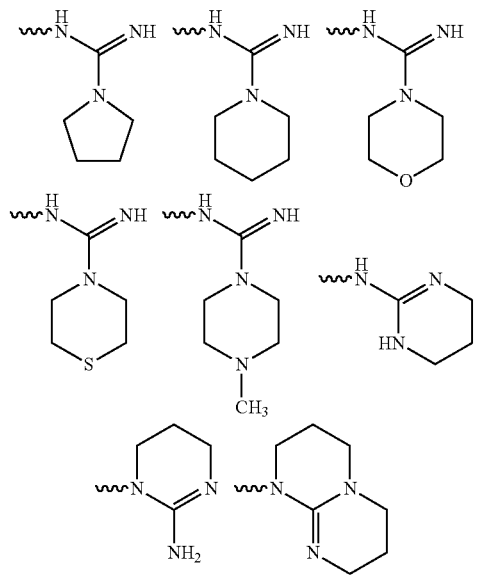

Examples of G¹, G², G³, G⁴ and G⁵ for the guanidine group (W) are the following: methyl, ethyl, propyl, isopropyl, cyclopropyl, butyl, isobutyl, tert-butyl, cyclobutyl, pentyl, cyclopentyl, hexyl, cyclohexyl, phenyl, etc, In addition, G² may also be a lone pair of electrons. Representative embodiments are as follows:

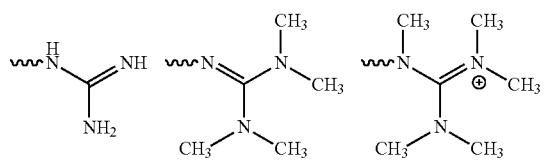

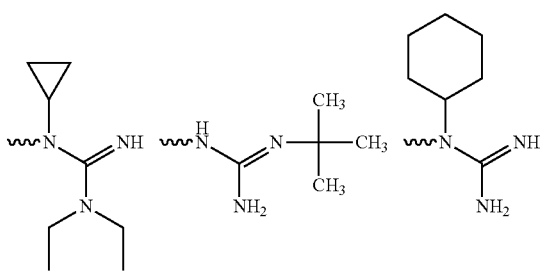

Examples of ring residues contained in X are cyclopropane, cylobutane, cyclopentane, cyclohexane or phenyl. Examples of X are shown in the following representative embodiments, where the wavy lines represent the bonds that connect X to the W part and the bore-containing part:

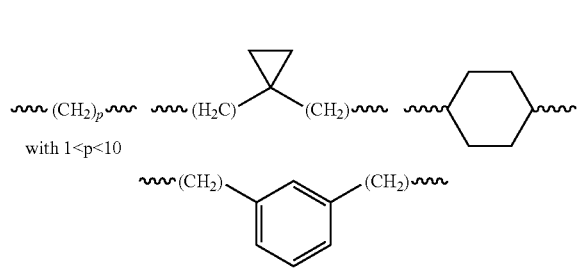

with 1<p<10

In yet another embodiment, Y and/or Z are OH or OR. When R is a cyclic alkyl group, this group optionally incorporates one or more heteroatoms such as N, O, S and halogen.

Examples of such Y and Z groups are shown in the following representative embodiments, where the wavy lines represent the bond connecting the boron atom to the other part of the molecule:

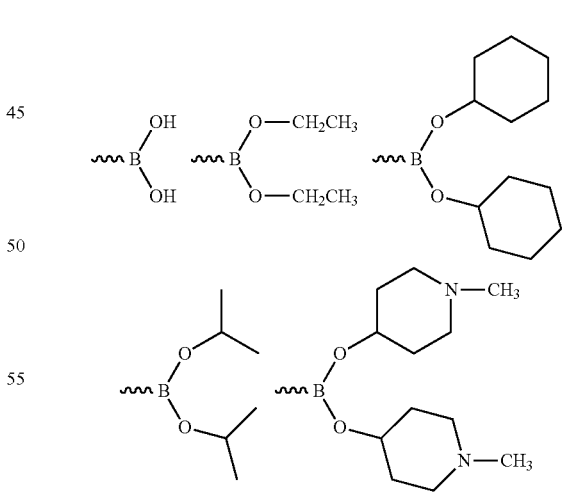

In yet another embodiment, Y and Z are branches of a homocyclic or heterocyclic structure, which incorporates the B atom and which contains up to 20 atoms chosen from C, O, N, and S atoms. Examples of such embodiments are shown below. The wavy line represents the bond connecting the B atom to the other part of the molecule:

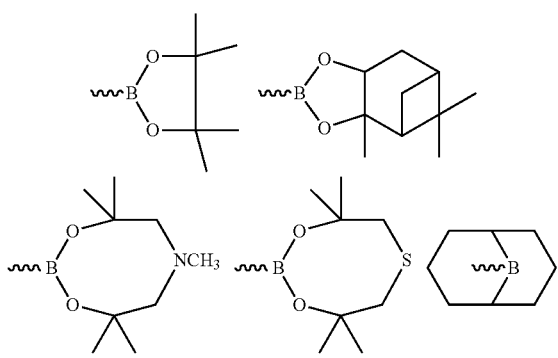

In yet another embodiment, Z is a linear or branched or cyclic alkyl group containing from 1 to 15 carbon atoms. Optionally, the linear or branched alkyl group for Z is substituted with one or more heteroatoms such as N, O, S and halogen. Examples of such Z groups are shown in the following representative embodiments, where the wavy lines represent the bond connecting Z to the other part of the molecule:

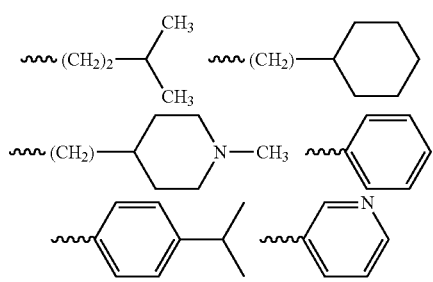

In yet another embodiment, the W—X—C—N(C=O)—$R^2$ part of the compound having formula I or II (structure bearing the boron atom) is an amino acid residue positively charged. An amino acid residue positively charged may be selected among arginine, lysine, ornithine or a derivative of one of these three amino acid residues as defined above.

In yet another aspect, the present invention relates to a compound based on boroarginine and having the following formula III:

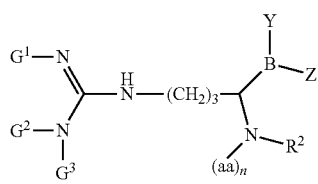

wherein
B represents a boron atom;
Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;
Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;
$R^2$ is either H, or a linear or branched or cyclic alkyl group containing from 1 to 10 carbon atoms, or an OR group wherein R may be H or a linear or branched or cyclic alkyl group containing from 1 to 10 carbon atoms;
$G^1$, $G^2$ and $G^3$ are, independently, H, or linear or branched or cyclic alkyl groups containing from 1 to 10 carbon atoms, or branches of a ring system that incorporates the N atom and that contains a total of up to 15 atoms; and
"aa" refers to any amino acyl residue or derivative thereof, and n is at least two.

Another embodiment of a compound based on boroarginine is a compound of formula IV, wherein at least one of $R^2$, $G^1$, $G^2$ and $G^3$ is H. Alternatively or in combination with the previous embodiment, at least one of $R^2$, $G^1$, $G^2$ and $G^3$ is a protecting group as defined above.

In another embodiment of a compound based on boroarginine is a compound of formula III, wherein $G^1$, $G^2$ and $G^3$ are H and having the following formula:

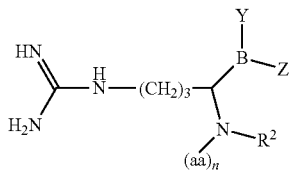

A compound based on boroarginine is a compound of formula III, wherein $R^2$, $G^1$, $G^2$ and $G^3$ are H and having the following formula:

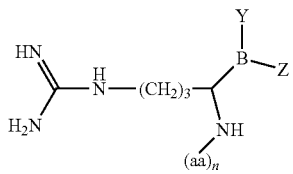

In yet another embodiment, the compound of the invention is based on borolysine or boroornithine and has the following formula IV:

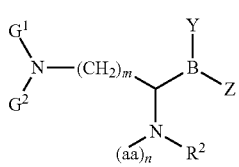

wherein
B represents a boron atom;
Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;

Z is an OH, or an is OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;

$R^2$ is either H, or a linear or branched or cyclic alkyl group containing from 1 to 10 carbon atoms, or an OR group wherein R may be H or a or a linear or branched or cyclic alkyl group containing from 1 to 10 carbon atoms;

$G^1$ and $G^2$ are, independently, H, or linear or branched or cyclic alkyl groups containing from 1 to 10 carbon atoms, or branches of a ring system that incorporates the N atom and that contains a total of up to 15 atoms;

"aa" refers to any amino acid residue or derivative thereof, and n is at least two; and m equals to 3 or 4.

In a embodiment, the compound is based on borolysine (m equals 4), and has the following formula (V)

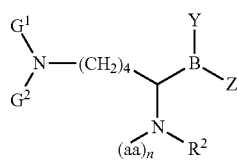

V wherein

B represents a boron atom;

Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;

Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;

$R^2$ is either H, or a linear or branched or cyclic alkyl group containing from 1 to 10 carbon atoms, or an OR group wherein R may be H or a or a linear or branched or cyclic alkyl group containing from 1 to 10 carbon atoms;

$G^1$ and $G^2$ are, independently, H, or linear or branched or cyclic alkyl groups containing from 1 to 10 carbon atoms, or branches of a ring system that incorporates the N atom and that contains a total of up to 15 atoms; and "aa" refers to any amino acid residue or derivative thereof, and n is at least two.

In another embodiment, the compound is based on boroornithine (m equals 3), and has the following formula (VI)

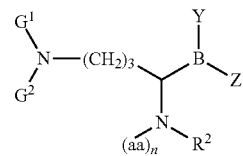

VI wherein

B represents a boron atom;

Y is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms;

Z is an OH, or is an OR group wherein R is a linear, branched or cyclic alkyl group incorporating from 1 to 10 carbon atoms, or is a branch of a homocyclic or heterocyclic structure, which incorporates the B atom and which contains up to 20 atoms chosen from C, O, N, and S atoms, or is a linear or branched or cyclic alkyl group containing from 1 to 15 carbon atoms;

$R^2$ is either H, or a linear or branched or cyclic alkyl group containing from 1 to 10 carbon atoms, or an OR group wherein R may be H or a or a linear or branched or cyclic alkyl group containing from 1 to 10 carbon atoms;

$G^1$ and $G^2$ are, independently, H, or linear or branched or cyclic alkyl groups containing from 1 to 10 carbon atoms, or branches of a ring system that incorporates the N atom and that contains a total of up to 15 atoms; and "aa" refers to any amino acid residue or derivative thereof, and n is at least two.

Another compound is a compound of formula IV, V or VI, wherein at least one of $R^2$, $G^1$ and $G^2$ is H. Alternatively or in combination with the previous embodiment, at least one of $R^2$, $G^1$ and $G^2$ is a protecting group as defined above.

Other compounds based either on formula IV, V or VI are compound wherein $G^1$ and $G^2$ are H and have the following formula:

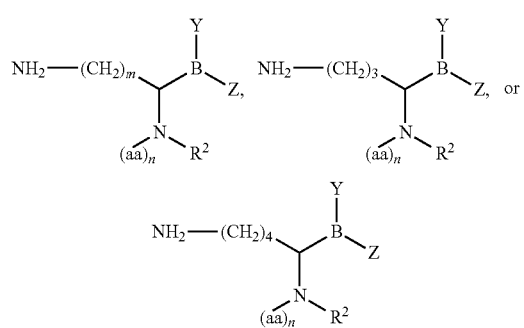

In another embodiment of a compound based on a compound of formula IV, V or VI, wherein $R^2$, $G^1$ and $G^2$ are H and have the following formula:

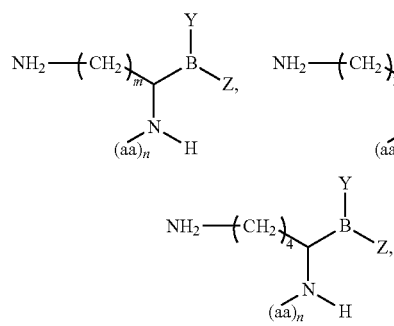

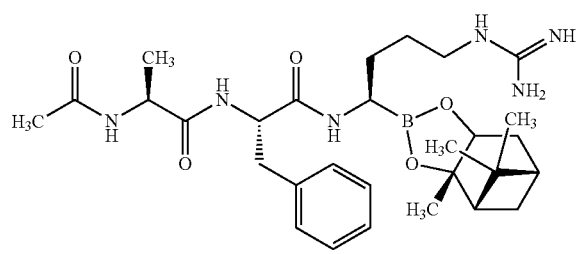

In yet another aspect, the compounds based on boroarginine (based on formula IV), on borolysine (based on formula V) or on boroornithine (based on formula VI), disclosed above, are also characterized by at least one of the following:

- at least one of Y or Z is OH. In an embodiment, Y and Z are OH.
- n is at least 2, and in another aspect is between 2 and 20, in another embodiment between 2 and 15, in another embodiment between 2 and 10, and in another embodiment between 2 and 5. In yet another aspect equals 2, 3, 4 or 5. When n equals 2, the resulting molecule is called a triboropeptide; when n equals 3, the resulting molecule is called a tetraboropeptide. The particular amino acid residues or derivative thereof that may constitute the triboropeptides or tetraboropeptides of the invention as well as the particular combination of amino acids residues have already been disclosed above for the definition of the compound of formula II, and apply in the same manner for the present triboropeptides and tetraboropeptides; and
- the first N-terminal amino acid residue of the n amino acids bears a protecting group as defined above. In another embodiment, the protecting group is linked to the free $NH_2$ group of the first N-terminal amino acid.

Examples of the compounds of formula I indicated are the following triboropetides and tetraboropetides: Tyr-Pro-BoroArg, Ala-Phe-BoroArg, Arg-Glu-BoroArg, Glu-Gly-BoroArg, Trp-Glu-BoroArg, Thr-Pro-BoroArg, Leu-Leu-BoroArg, Phe-Arg-Val-BoroArg, Arg-Cys-Thr-BoroArg, Gly-Cys-Pro-BoroArg, Gly-Pro-Cys-BoroArg, Gly-Cys-Asn-BoroArg and Lys-Gly-Asp-BoroArg.

Other compounds are Ala-Phe-BoroArg, Ac-Ala-Phe-BoroArg, Glu-Gly-BoroArg and Ac-Glu-Gly-BoroArg, as disclosed respectively in formulas VII, VIII, IX and X.

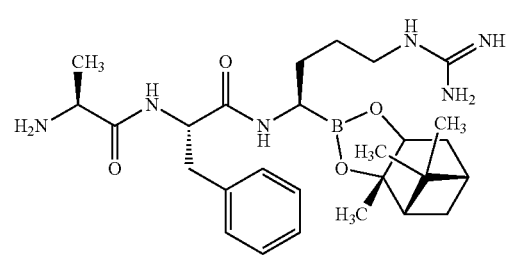

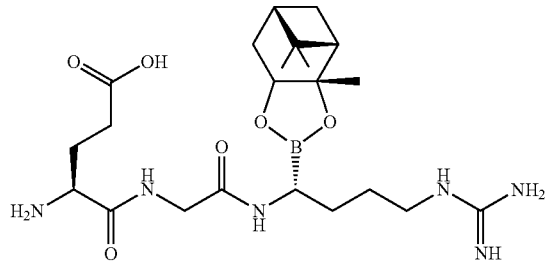

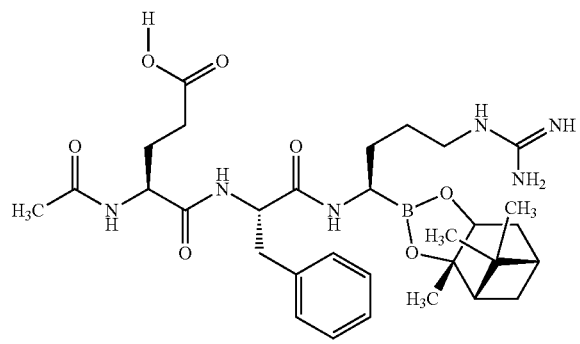

All the compounds of the invention disclosed in the present application are under a free base form or are pharmaceutically acceptable salts thereof.

In contrast, the compounds of the invention are not at least one of the following:

Ac-(D,L)Phe-boroArg-$C_{10}N_{16}$.BSA (benzene sulfonic acid), Ac-Phe-boroOrn-$C_{10}H_{16}$.BSA, Ac-Phe boroArg-$C_{10}H_{16}$.HCl, H-(D)Phe-Pro-boroIrg-$C_{10}H_{16}$.HBr.HCl, Boc-(D)Phe-Pro-boroIrg-$C_{10}H_{16}$. HBr, Ac-Phe-boroIrg-$C_{10}H_{16}$.HBr, Ac-Ala-Lys(Boc)-boroOrn-$C_{10}H_{16}$.BSA, Ac-Ala-Lys(Boc)-boroIrg-$C_{10}H_{16}$.HBr, Boc-(D)Phe-Pro-boroArg-$C_{10}H_{16}$.BSA, Boc-(D)Phe-Phe-BoroIrg-$C_{10}H_{16}$.HBr, H-(D)Phe-Pro-boroArg-$C_{10}H_{16}$.HCl, Boc-(D)Phe-Phe-boroOrn-$C_{10}H_{16}$.BSA, Boc-(D)Phe-Phe-boroArg-$C_{10}H_{16}$.BSA, Ac-Ala-Lys(Boc)-boroArg-$C_{10}H_{16}$.BSA, Ac-(D)Phe-Pro-boroArg-$C_{10}H_{16}$.HCl, Ac-(D)Phe-Pro-boroArg-OH.HCl, Boc-Leu-Gly-Leu-Ala-boroIrg-$C_{10}H_{16}$.HBr, Boc-Leu-Gly-Leu-Ala-boroOrn-$C_{10}H_{16}$.BSA, Boc-Leu-Gly-Leu-Ala-boroArg-$C_{10}H_{16}$.BSA, Bz-Pro-Phe-boroOrn-$C_{10}H_{16}$.BSA, Bz-Pro-Phe-boroArg-$C_{10}H_{16}$.BSA, Boc-Ala-Phe-(D,L)boroIrg-$C_{10}H_{12}$.HBr, Bz-Glu(OBu)-Gly-boroIrg-$C_{10}H_{16}$.HBr, Bz-Glu-Gly-boroArg-$C_{10}H_{16}$.BSA, Bz-Glu(OBu)-Gly-boroOrg-$C_{10}H_{16}$.BSA, Bz-Glu(OBu)-Gly-boroArg-$C_{10}H_{16}$.BSA, Bz-Pro-Phe-boroIrg-$C_{10}H_{16}$.H Br, Z-Phe-Gly-Gly-boroIrg-$C_{10}H_{16}$.HBr, Boc-Ala-Phe-(D,L)borohomoIrg-$C_{10}H_{12}$.HBr, Bz-Pro-Phe-boroArg- OH.HCl, Bz-Pro-Phe-boroArg-F, H-(D)Phe-Pro-boroArg-$C_{10}H_{16}$.2HCl, H-(D)Phe-Phe-boroArg-$C_{10}H_{16}$.2HCl, Ac-Ala-Lys-boroArg-$C_{10}H_{16}$.2HCl, H-Leu-Gly-Leu-Ala-boroArg-$C_{10}H_{16}$.HCl.BSA, Boc-Ala-Phe-(D,L)boroLys-$C_{10}H_{12}$.HCl, H-Ala-Phe-(D,L)boroLys-$C_{10}H_{12}$.2HCl, Boc-(D)Val-Leu-boroLys-$C_{10}H_{12}$.HCl, Ac-Phe-boroLys-$C_{10}H_{12}$.HCl, Bz-Glu-Gly-boroArg-$C_{10}H_{16}$.BSA, H-(D)Phe-Phe-boroIrg-$C_{10}H_{16}$.2HBr, H-Leu-Gly-Leu-Ala-boroIrg-$C_{10}H_{16}$.2HBr, H-Ala-Phe-(D,L)boroIrg-$C_{10}H_{12}$.2HBr, Bz-Glu-Gly-boroIrg-$C_{10}H_{16}$.HBr, H-Ala-Phe-(D,L)boroHomoIrg-$C_{10}H_{12}$.2HBr, Ac-Ala-Lys-boroIrg-$C_{10}H_{16}$.2HBr, Bz-boroIrg-$C_{10}H_{12}$.HBr, Bz-boroOrn-$C_{10}H_{12}$.BSA, Bz-boroArg-$C_{10}H_{12}$.BSA, Ac-Leu-Thr(OBu)-boroOrn-$C_{10}H_{16}$.BSA, Ac-Leu-Thr(OBu)boroArg-$C_{10}H_{16}$.BSA, Ac-Leu-Thr-boroArg-$C_{10}H_{16}$.BSA, Ac-Lys(Boc)-Pro-boroOrn-$C_{10}H_{16}$.BSA, Ac-Lys(Boc)-Pro-boroArg-$C_{10}H_{16}$.BSA, Ac-Lys-Pro-boroArg-$C_{10}H_{16}$.BSA, Ac-Ala-Glu(OBu)-boroOrn-$C_{10}H_{16}$.BSA, Ac-Ala-Glu(OBu)-boroArg-$C_{10}H_{16}$.BSA, Ac-Ala-Glu-boroArg-$C_{10}H_{16}$.BSA, Boc-Val-Val-boroLys-$C_{10}H_{12}$.BSA, H-Val-Va]-boroLys-$C_{10}H_{12}$.BSA.TFA, Boc-(D)Phe-Phe-boroLys-$C_{10}H_{12}$.BSA, H-(D)Phe-Phe-boroLys-$C_{10}H_{12}$.BSA.TFA, Boc-Glu-Phe-boroLys-$C_{10}H_{12}$.BSA and PyroGlu-Phe-boroLys-$C_{10}H_{12}$.BSA, disclosed in U.S. Pat. No. 5,187,157;

Ac-boroArg-OH.HCl, disclosed in Lebarbier et al.; (1998) Biorganic and Medicial Chemistry letters 8: 2573-2576;

Ac-(D)-Phe-Pro-boroArg-OH, disclosed in Quan et al.; (1997) Biorganic and Medicial Chemistry letters 7(13): 1595-1600;

Ac-Ala-Lys-boroArg-$OH_2$, disclosed in Holyoak et al. (2003); Biochemistry 42: 6709-6718.

Pro-Phe-BoroArg-OH, disclosed in Stadnicki et al. (1998); The FASEB Journal 12: 325-333.

Bz-Nle-Lys-Lys-boroArg-$OH_2$, disclosed in Yien et al. (2006); Biorganic and Medicial Chemistry letters 16: 36-39.

H-Phe-Pro-BoroArg, disclosed in Kettner et al. (1990); The Journal of Biological Chemistry 265(30): 18289-18297.

Ac-Arg-Glu-Lys-boroArg pinanediol, disclosed in Komiyama et al. (2005); Antimicrobial Agents and Chemotherapy 49(9): 3875-3882.

(BOC)-Ala-Val-Lys-boronate, disclosed in Katz et al. (1995); Biochemistry 34: 8264-8280.

Figure 7A:
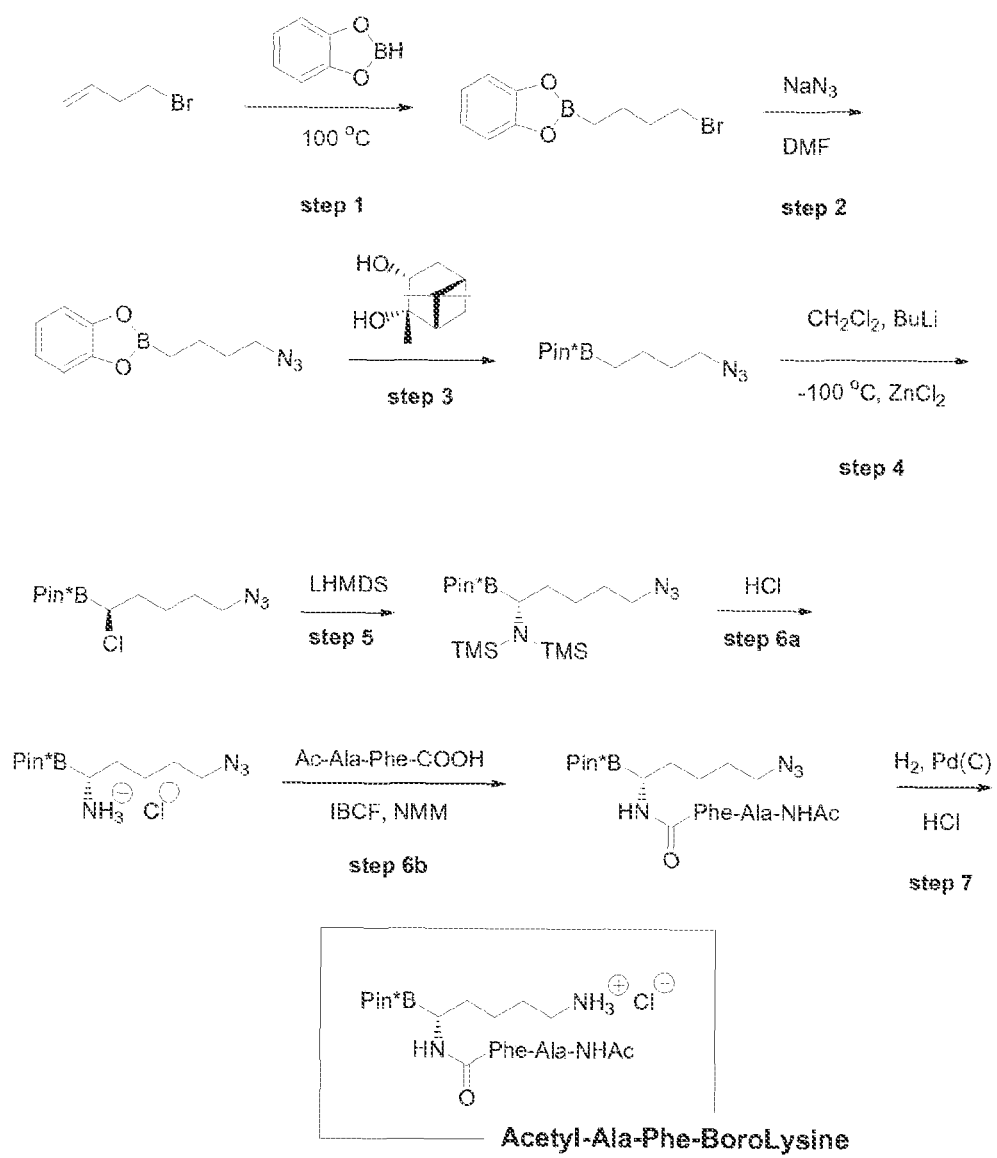
Figure 7D:
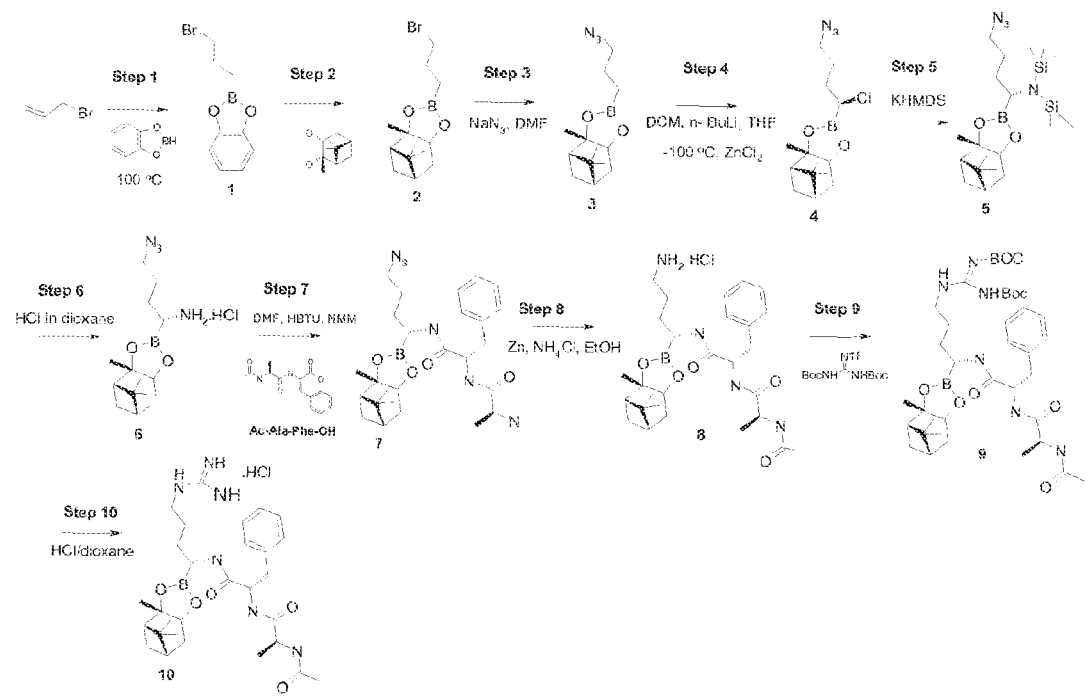
Figure 7E:
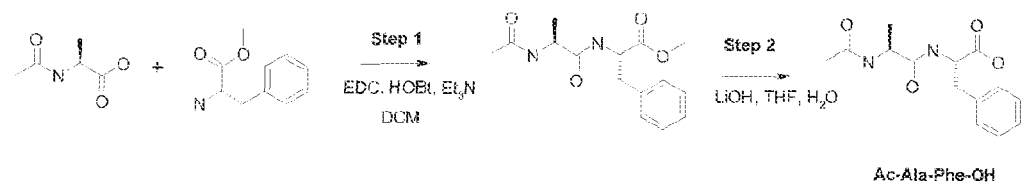

The molecules of the invention are synthesized using well-know processes. As an example, FIG. 7 discloses various processes to synthesize any compound of the present invention. The examples disclosed relates to the synthesis of a borolysine tripeptide (7A), a bororarginine tripeptide and a boroornithine tripeptide (7B to 7E). These examples may be easily applied to synthesize other compounds disclosed herein. Especially, the person skilled in the art may replace the nature and number of amino acid residues to link to the boroarginine, borolysine or boroornithine moiety.

Besides their structural feature, the compounds of the invention, and especially the tri or tetraboropeptides, have the capacity to specifically inhibit the activity of serine proteases and especially the activity of trypsin-like subtype serine proteases. In another embodiment, the compounds of the invention, and especially the tri or tetraboropeptides, have the capacity to selectively inhibit, the activity of enteropeptidase, especially mammalian enteropeptidases, and more especially human enteropeptidase. The sequence of the human enteropeptidase is disclosed in FIG. 6.

In a second embodiment, the invention relates to a composition comprising one or more than one compound of the invention, especially 2, 3 or 4 compounds.

Such composition can take the form of a pharmaceutical composition which can be formulated using pharmaceutically acceptable carriers well known in the art, in suitable dosages.

In a particular embodiment, the composition further comprises a pharmaceutically suitable excipient or carrier and/or vehicle, when used for enteral or oral administration.

Such carriers enable the pharmaceutical compositions to be formulated as tablets, pills, dragees, capsules, liquids, gels, syrups, slurries, suspensions, and the like.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize, wheat, rice, or potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

In addition to the active ingredients, these pharmaceutical compositions may also contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Pubiishing Co., Easton, Pa.).

In an embodiment of the invention, the compounds of the present invention may be administered in combination with at least one other drug, to achieve enhanced effects, for example with other drugs targeting enzymes different from the enteropeptidase. As an example, the compounds of the invention may be combined with drug(s) able to inhibit the adsorption or the metabolism of triglycerides.

In a third embodiment, the present invention relates to the use of any compound as defined above, and particularly any compound of the formula I to VI for the treatment of obesity, excess weight and diseases associated with an abnormal fat metabolism. Therefore, the compounds of the invention, particularly the compounds of the formula I to VI for use as drug, particularly for use in the treatment of obesity, excess weight and/or diseases associated with an abnormal fat metabolism, are part of the invention, as well as the use of a compound or a composition of the invention for the manufacture of a drug to treat obesity, excess weight and/or diseases associated with an abnormal fat metabolism.

The invention is also directed to a method to treat a mammal having obesity, having excess weight and/or suffering from diseases associated with an abnormal fat metabolism, comprising administrating at least one compound or a composition of the invention to a mammal in need thereof.

In an embodiment, any compound of the invention may be used to decrease the in vivo absorption of proteins. In another embodiment, any compound of the invention may be used to decrease the in vivo absorption of triglycerides. In a further embodiment, any compound of the invention may be used to decrease the in vivo absorption of proteins and the in vivo absorption of triglycerides.

In a further aspect, independently or in combination with the use of the compounds of the invention in absorption decrease, any compound of the invention may be used to decrease the food intake, i.e; to decrease the appetite (appetite blocker).

The compound or the composition of the invention may be used in dosage ranging from 10 mg to 10 g per day, or from 100 mg to 1 g per day, one or several times daily. The amount of compound(s) or the composition of the present invention may be administered in dosages according to the severity of the obesity, the amount of excess weight, the age of the mammal and/or the general health of the mammal.

The compounds or compositions of the invention are suitable for treating various forms of obesity and in particular obesity resulting from environmental causes (excessive nutrient intake and/or a sedentary lifestyle), resulting from genetic alterations (such as FTO gene), resulting from medical illness (such as hypothyroidism, Cushing's syndrome, growth hormone deficiency), resulting from smoking cessation, resulting from medications (such as steroids, atypical antipsychotics or some fertility medication), and resulting from neurological disorders.

The treatment by at least one the compounds or by the compositions of the invention of diseases associated with an abnormal fat metabolism is also contemplated. Such diseases are the following: gout disease (metabolic arthritis), type II diabetes, hyperglycemia, hyperinsulinemia, elevated blood levels of fatty acids or glycerol, syndrome X, diabetic complications, dysmetabolic syndrome and related diseases, hypercholesterolemia, atherosclerosis, hypertension, pancreatitis, hypertriglyceridemia, hyperlipidemia, stroke, coronary heart diseases, peripheral vascular diseases, peripheral arterial diseases, vascular syndromes, cholesterol-related disorders (e.g., LDL-pattern B and LDL-pattern L) and drug-induced lipodystrophy.

The invention also concerns an animal model in which the enteropeptidase gene has been inactivated. This model encompasses a mammal model (non-human) or a murine model (such as a mouse). By "inactivated", is meant that an enteropeptidase gene incorporated in this model encodes a protein having less than 50% enteropeptidase activity as compared to the wild type enteropeptidase. In one embodiment, the inactivated enteropeptidase has less than 40% enteropeptidase activity as compared to the wild type enteropeptidase. In another embodiment, the enteropeptidase of the animal model has less than 30% enteropeptidase activity as compared to the wild type enteropeptidase. In yet another embodiment, the enteropeptidase of the animal model has less than 20% or less than 10% enteropeptidase activity as compared to the wild type enteropeptidase. In still another embodiment, the inactivated enteropeptidase has no peptidase activity at all. In another aspect, the percentage of enteropeptidase activity is defined according to the conversion of trypsinogen into trypsin.

The animal model having an inactivated enteropeptidase gene may be obtained by any conventional techniques known to the person skilled in the art to obtain a knockout (KO) animal model, such as by inserting one or more amino acid substitution(s) affecting the peptidase activity of the enteropeptidase or by deleting one or several exons of the enteropeptidase gene. When the animal model is a rodent, such as a mouse, mutations may be, for example, a deletion of exons 23-28 of the prss7 gene i.e., the murine counterpart of human enteropeptidase.

The invention is also directed to the use of this animal model in drug development, for example in the screening of drugs or molecules having effects on weight. Therefore, the model can be used in a process to determine the effect of a drug or a molecule on weight comprising (a) administrating a drug to the model and (b) measuring the weight of the animal. The effect of the drug is determined by comparing the weight of the animal administered with said drug with control animals (which are administered with known molecules or with a placebo).

The expression "effect on weight" means that the drug or molecule is able to increase the weight of the animal model as compared to a placebo, or in contrast to decrease the weight of the animal model as compared to a placebo. The effect of the molecule may be observed under a low, normal or high caloric regimen.

The administration of the drug or the molecule to the animal model may be carried out orally intravenously, intraperitonally, intramuscularly, intraarterially or by sustained release systems.

A number of embodiments of the invention have been described. Nevertheless, it will be understood that various modifications may be made without departing from the spirit and scope of the invention.

EXAMPLES

A. In Vitro Experiments

1. Materials
1.1. Buffer:
TN: Tris 50 mM pH=7.5 NaCl 150 mM (Tris: Euromedex Ref 26-128-3097; NaCl: Euromedex Ref 1112);
TCN: Tris 50 mM pH=7.5 NaCl 150 mM $CaCl_2$ 10 mM;
TCNB: Tris 50 mM pH=7.5 NaCl 150 mM, $CaCl_2$ 10 mM, 0.05% Brij 35 (Brij: sigma Ref B4184);
Tris 25 mM pH 8;
Pancreatic lipase Buffer: 25 mM Tris pH 9.2—0.1 mM $CaCl_2$—20 mM sodium;
Deoxycholate;
Thermolysine (Sigma, ref T7902);
Phosphoramidon disodium salt (Sigma, ref R7385);
Acetic Acid (Sigma ref A0808)
1.2. Plates
Microplate 384 small volume, clear (Greiner, ref 784101)

Microplate 384 flat bottom black (Corning, ref 3573)
Plate 96 black Nunc (VWR, ref 13634.01)
Plate 96-½ area (Corning, Ref 3695)
Microplate 96 well 800 µl unifilter (Whatman, Ref 7700-1804)

1.3. Compounds

Table I below lists four compounds of the invention (triboropeptides) and their names.

TABLE I

| Name | Compound/Composition | Protection |
|---|---|---|
| Obe 1999 | Ala-Phe-BoroArg 10 mM DMSO | No |
| Obe 2000 | Glu-Gly-BoroArg 10 mM DMSO | No |
| Obe 2001 | Acetyl-Ala-Phe-BoroArg 10 mM DMSO | Yes (Acetyl on the first Ala) |
| Obe 2002 | Acetyl-Glu-Gly-BoroArg 10 mM DMSO | Yes (Acetyl of the first Glu) |

1.4. Enzymes:

Table II below lists the enzymes tested for inhibition by the compounds of the invention, as well as the suppliers and the associated commercial references.

TABLE II

| Enzyme | Supplier, reference |
|---|---|
| Recombinant human enteropeptidase | RD system, ref 1585SE |
| Trypsin from human pancreas | SIGMA, ref T6424 |
| Thrombin from human plasma | SIGMA, ref T1063 |
| Kallikrein from human plasma | SIGMA, ref K2638 |
| Plasmin from human plasma | SIGMA, ref P1867 |
| Elastase | Calbiochem, ref 324682 |
| Chymotrypsin | Sigma, ref C8946 |
| DPPIV (Dipeptidyl peptidase IV) | RD System, ref 1180-SE |
| Recombinant human Carboxypeptidase A1 | RD System, ref 2856-ZN |
| Recombinant human Carboxypeptidase B1 | RD System, ref 2897-ZN |
| Alpha Amylase from human pancreas | Sigma, ref A9972 |
| Lipase | Sigma, ref L0382 |

1.5. Substrates:

Table III below lists the substrates used for testing the inhibition of the above enzymes by the compounds of the invention, as well as the suppliers and the associated commercial references.

TABLE III

| Substrate | Supplier, reference | Corresponding enzyme |
|---|---|---|
| N-p-Tosyl-Gly-Pro-Arg-pNa | SIGMA, ref T1637 | Enteropeptidase, Trypsin and Thrombin |
| H-D-Pro-Phe-Arg-pNa | Chromogenix, ref S-2302 | Kallikrein |
| D-Ile-Phe-Lys-pNa | SIGMA, ref I6886 | Plasmin |
| N-Succinyl-Ala-Ala-Pro-Phe-pNA | Sigma, ref S7388 | Chymotrypsin |
| Suc-Ala-Ala-Pro-Abu-pNA | Calbiochem, ref 324699 | Elastase |
| Ala-Pro-7-amido-4-trifluoromethylcoumarin | Calbiochem, ref 125510 | DPPIV |
| N-(4-Methoxyphenylazoformyl)-Phe-OH potassium salt | Bachem, ref M2245 | Carboxypeptidase A1 |
| N-(4-Methoxyphenylazoformyl)-Arg-OH HCl | Bachem, ref M2525 | Carboxypeptidase B1 |
| 6,8-difluoro-methylumbelliferyl octanoate (DIFMu) | InVitrogen, ref D12200 | Lipase |
| Starch Azur | Sigma, ref S7629 | Alpha Amylase |

2. Protocols 2.1. Enteropeptidase Assay

Activation of the Enteropeptidase

A mix of enteropeptidase at 58.8 nM (final) and thermolysine at 1.58 ng/I (final) in TCN buffer was prepared; the mix was incubated at 37° C. during 30 minutes for activation. Phosphoramidon (10 µM final) was added to stop the activation by thermolysine.

Measurement of Enteropeptidase Activity without Inhibitor (Positive Control)

In 17 µl of TCN, 1 µl of active enzyme (2.9 nm final) and 2 µl Np Tosyl Gly Pro Arg pNa (1 mM final) were mixed, just before reading. The Absorbance was measured at 405 nm on EnVision (Perkin Elmer).

Inhibition in 384 Well Plate Small Volume (200 Final)

In 15 µl of TCN, 1 µl of active enzyme and 2 µl of Inhibitor (compound of the invention) at different concentrations were mixed, and incubated at RT (room temperature) for 30 minutes; 2 µl Np Tosyl Gly Pro Arg pNa (1 mM final) was added just before reading. The Absorbance was measured at 405 nm on EnVision (Perkin Elmer).

2.2. Thrombin, Trypsin, Kallikrein, Plasmin, Chymotrypsin and Elastase Assay

Table IV below lists the final concentrations of the tested enzymes and the corresponding substrates, in the determination of the $IC_{50}$ without inhibitor (positive control) and in inhibition protocols:

TABLE IV

| Enzyme | Susbstrate |
|---|---|
| Trypsin 10 nM | N-p-Tosyl-Gly-Pro-Arg-pNa 1 mM |
| Thrombin 10 nM | N-p-Tosyl-Gly-Pro-Arg-pNa 0.75 mM |
| Plasmin 50 nM | D-Ile-Phe-Lys-pNa 1 mM |
| Kallikrein 10 nM | H-D-Pro-Phe-Arg-pNa 1 mM |
| Chymotrypsin 50 nM | N-Succinyl-Ala-Ala-Pro-Phe-pNA 0.5 mM |
| Elastase 25 nM | Suc-Ala-Ala-Pro-Abu-pNA 0.5 mM |

Measurement without Inhibitor (Positive Control)

In 17 µl of TN, 1 µl of enzyme and 2 µl of substrate was mixed, just before reading; The Absorbance was measured at 405 nm on EnVision (Perkin Elmer).

Inhibition in 384 Well Plate Small Volume (200 Final)

In 15 µl of TN, 1 µl of enzyme and 2 µl of Inhibitor (compound of the invention) at different concentrations were mixed and incubated at RT for 30 minutes; 2 µl of substrate was added, just before reading; The Absorbance was measured at 405 nm on EnVision (Perkin Elmer).

2.3 Carboxypeptidase A1 and B1 Assay

Activation of Carboxypeptidase A1

In 20 µl of TCNB, Carboxypeptidase A1 (100 µg/ml final) and trypsin (1 µg/ml final) were mixed and incubated at RT for 2 hours.

Activation of Carboxypeptidase B1

In 20 μl of TCNB, Carboxypeptidase B1 (100 μg/ml final) and trypsin (1 μg/ml final) were mixed and incubated at RT for 1 hour.

Table V below lists the final concentrations of the tested enzymes and the corresponding substrate, in the determination of the $IC_{50}$ without inhibitor (positive control) and in inhibition protocols:

TABLE V

| Enzyme | Susbstrate |
|---|---|
| Carboxypeptidase A1, 20 nM | N-(4-Methoxyphenylazoformyl)-Phe-OH, potassium salt 100 μM |
| Carboxypeptidase B1, 20 nM | N-(4-Methoxyphenylazoformyl)-Arg-OH, HCl 100 μM |

Measurement without Inhibitor (Positive Control)

In 17 μl of TN, 1 μl of activated enzyme and 2 μl substrate were mixed, just before reading; The Absorbance was measured at 355 nm on EnVision (Perkin Elmer).

Inhibition in 384 Well Plate Small Volume (20 μl Final)

In 15 μl of TN, 1 μl of activated enzyme and 2 μl of Inhibitor (compounds of the invention) at different concentrations were mixed, and incubated at RT for 30 minutes; 2 μl of substrate was added, just before reading; The Absorbance was measured at 355 nm on EnVision (Perkin Elmer).

2.4. DPPIV Assay

Measurement without Inhibitor (Positive Control)

In 17 μl of Tris 25 mM pH 8, 1 μl of enzyme (1 nM final) and 2 μl of substrate (Ala-Pro-7-amido-4-trifluoromethyl-coumarin, at 100 μM final) were mixed, just before reading. The Absorbance was measured on EnVision (Perkin Elmer) (Excitation 400 nm/Emission 505 nm).

Inhibition in 384 Well Plate Black (20 μl Final)

In 15 μl of Tris 25 mM pH 8, 1 μl of enzyme (1 nM final) and 2 μl of Inhibitor (compounds of the invention) at different concentrations were mixed, and incubated at RT for 30 minutes. 2 μl of substrate (Ala-Pro-7-amido-4-trifluoromethylcoumarin, at 100 μM final) was added, just before reading. The absorbance was measured on EnVision (Perkin Elmer) (Excitation 400 nm/Emission 505 nm).

2.5. Pancreatic Amylase Assay

Measurement without Inhibitor (Positive Control)

In 50 μl, 5 μl Amylase (at a starting concentration of 0.25 mg/ml) and 45 μl of Starch Azur (at a starting concentration of 2% in 20 mM NaH2PO4/50 mM Na Cl pH 7) were mixed and incubated 1 h at 37° C. with shaking. 20 μl Acetic Acid Solution (starting concentration of 2.75 M) was added, and the suspension filtered. The absorbance was measured in microplate 96 well unifilter Whatman at 595 nm.

Inhibition in 96 Well Plate Black

In 35.5 μl buffer (NaH$_2$PO$_4$/50 mM NaCl pH 7-37° C.), 5 μl of amylase (0.25 mg/ml) and 5 μl of Inhibitor (compounds of the invention) at different concentrations were mixed and incubated 30 minutes at RT. 4.5 μl of substrate (Starch Azur 20% in buffer) were added and incubated 1 hour at 37° C. under shaking. Then, 20 μl of Acetic Acid Solution (2.75 M) were added and the suspension was filtered in a microplate 96 well unifilter Whatman. Absorbance was read at 595 nm on EnVision (Perkin Elmer).

2.6. Lipase Assay

Measurement without Inhibitor (Positive Control)

In 85 μl of lipase buffer, 5 μl of lipase (56 U/ml final) and 10 μl of substrate (DiFMu at 10 μM final) were mixed, just before reading. The florescence was measured on EnVision (Perkin Elmer) (Excitation 358 nm/Emission 452 nm).

Inhibition in 96 Well Plate Black (200 Final)

In 80 μl of lipase buffer, 5 μl of lipase (56 U/ml final) and 5 μl of Inhibitor (compounds of the invention) at different concentrations were mixed, and incubated at RT for 30 minutes. Add 10 μl of substrate (DiFMu at 10 μM final) just before reading. The fluorescence was measured on EnVision (Perkin Elmer) (Excitation 358 nm/Emission 452 nm).

3. Results

As shown in FIGS. 1 to 4, the 4 compounds (OBE1999 to OBE2000), belonging to the boropeptide family, are particularly efficient in vitro against enteropeptidase and inhibit the activity of enteropeptidase, with a high IC50 inhibition constant, at a nanomolar range from 7 to 63 nM. Moreover, these four compounds are specific of serine proteases, sub-type trypsin-like, and in contrast do not inhibit chymotrypsin-like serine proteases, metallo-proteases or glucosidases (FIG. 5).

More specifically, OBE1999 is a very good inhibitor of enteropeptidase (IC50 of 33 nM). However, it also inhibits with a good IC50 (7.5 to 29.8 nM) other enzymes such as trypsin, kallikrein and plasmin. Since the enteropeptidase is specifically located in the luminal intestine and this compound is non-absorbable, this compound is an excellent molecule to selectively inhibit the enteropeptidase, and is thus not expected to inhibit in vivo other serine protease (whose location is non-intestinal). As far OBE2001 is concerned, this compound shares the same profile as the one of OBE 1999 and therefore fulfils the same specificity and selectivity criteria.

OBE2000 is more specific for enteropeptidase and trypsin than the compounds OBE1999 and OBE2001, with low value of IC50 for enteropeptidase, and high value of IC50 not only for thrombin but also for plasmin (7100 nM) and kallikrein (260 nM). OBE2002 presents the same profile as OBE2000, except for the low IC50 value against kallikrein and plasmin as compared to OBE2000.

Consequently, these results also clearly show that all tested compounds have a remarkable efficiency in the in vitro inhibition of enteropeptidase, and can be considered as promising molecules for future in vivo experiments in animals and/or in humans. These compounds have been shown to fulfil at least two requirements necessary for treatment: the specificity of inhibition to trypsin-like subtype serine proteases, and the selectivity of the inhibition for the enteropeptidase.

B. In Vivo Experiments

1. Effect of OBE2001 on Weight

The aim of this first in vivo experiment is to determine the anti-obesity effect of OBE2001 in a model of obesity induced by a hyperlipidic diet in mice.

OBE2001 (Acetyl-Ala-Phe-BoroArg) was provided under salt form (molecular weight of 568.3 g/mol). Swiss male mice, 4 weeks of age, were divided into 2 groups of 10 animals each, receiving the following:

| Group number | Diet | Dosing |
|---|---|---|
| 1 | Hight fat, ad libitum | Vehicle (water) |
| 2 | Hight fat, ad libitum | OBE2001 (40 mg/kg/day) |

Administration of OBE2001 was carried out as a solution in water. Both OBE2001 or vehicle (water used a negative control) were administrated to the animals daily by the oral route in an administration of 5 ml/kg body weight.

Concerning the feeding of the animals, before the experiments (acclimation period), normal diet (reference No. 824050 SDSIDIETEX food) was available ad libitum during the acclimation period. 7 days before the beginning of the study, a hypercaloric High Fat diet (45% proteins, 4.73 Kcal/g; reference 824053 SDSIDIETEX) was given to groups 1 and 2.

Animals were weighed daily from at D-8 (8 days before the beginning of the experiment) then from D-5 to the end of the study. From D1 (first day of the experiment), food was given ad libitum.

Results

Figure 8:
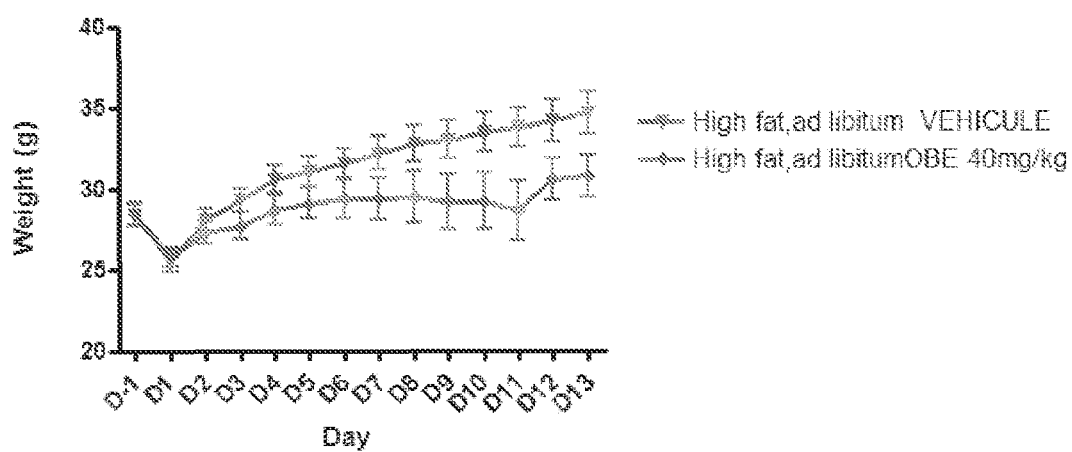
FIG. 8 is a graph illustrating the follow up in days of the weight (in grams) of mice having received water (vehicle) as compared to mice having received OBE2001 at a concentration of 40 mg/kg/day (B).

The initial body weight (in g) of mice of groups 1 and 2 at D-1 (one day prior to the experiment) as well as the gain or loss of weight according to the initial weight (for D1 to D13) are summarized in the following table and represented on FIG. 8.

| Group | | D-1 | D1 | D2 | D3 | D4 | D5 | D6 | D7 |
|---|---|---|---|---|---|---|---|---|---|
| 1 | Mean | 28.3 | −2.8 | −0.3 | 1.0 | 2.3 | 2.7 | 3.2 | 3.9 |
|   | SEM  | 0.7  | 0.2  | 0.1  | 0.2 | 0.3 | 0.4 | 0.4 | 0.5 |
| 2 | Mean | 28.5 | −2.7 | −1.2 | −0.8| 0.2 | 0.7 | 1.0 | 0.9 |
|   | SEM  | 0.7  | 0.2  | 0.2  | 0.3 | 0.5 | 0.6 | 0.9 | 1.0 |
|   | p    | NS   | NS   | NS   | NS  | *   | *   | *   | *   |

| Group | | D8 | D9 | D10 | D11 | D12 | D13 |
|---|---|---|---|---|---|---|---|
| 1 | Mean | 4.4 | 4.7 | 5.1 | 5.4 | 5.9 | 6.3 |
|   | SEM  | 0.6 | 0.7 | 0.7 | 0.8 | 0.8 | 0.8 |
| 2 | Mean | 1.3 | 1.0 | 1.1 | 0.5 | 1.8 | 2.0 |
|   | SEM  | 1.3 | 1.3 | 1.4 | 1.5 | 1.0 | 1.1 |
|   | p    | **  | **  | **  | **  | **  | **  |

Mean: mean weight of the 10 mice per group;
SEM: standard error of the mean;
NS: non significant difference between the two groups ($p > 0.05$);
*: $p \leq 0.05$;
: $p \leq 0.01$ As shown in FIG. 8**, this experiment showed that the weight of mice having received the OBE2001 compound is significantly lower than the weight of the control group mice. This difference is significant from day 4 and highly significant from day 8 (see Table). Consequently, the administration of OBE 2001 in mice results in the decrease of the weight as soon as day 4.

2. Effect of OBE2001 on Triglyceride Absorption

The scope of this second in vivo experiment was to analyse the effects of the OBE2001 compound on triglycerides absorption. To that purpose, mice were injected with OBE2001, before and/or after gavage with a solution enriched with cholesterol and free fatty acids (clinoleic at 20%).

In this study, 7 week old Swiss CD1 male mice were weighed and randomized for body weight; 3 groups of 5 mice were then constituted of:

Group 1 (solvant): control group. Vehicle ($H_2O$+2% DMSO) at t-5 min+solution A (clinoleic 20%+cholesterol) at t0.

Group 2 (OBE 25+25): OBE2001 25 mg/kg (before and after gavage). OBE2001 25 mg/kg (solution B) at t-5 min+OBE2001 25 mg/kg in solution A (solution C) at t0.

Group 3 (OBE 25): OBE2001 25 mg/kg (before gavage). Vehicle ($H_2O$+2% DMSO) at t-5 min+OBE2001 25 mg/kg in solution A (solution C) at t0.

30 minutes before treatment (with solution A, B or C) blood was collected by retro orbital puncture after a slight anaesthesia (Isoflurane), to determine basal (t0) triglycerides levels. All solutions were then administered by oral gavage at t-5 (vehicle or solution B) or t0 (solution A or C). After administration of the solution A or C (containing fatty acids+cholesterol), blood was collected again by retro orbital puncture after a slight anaesthesia (Isoflurane) at time 60, 120, 180, 300 and 360 minutes for measurement of triglycerides levels. At time 360 minutes, mice were sacrificed.

Results:

The following values were obtained at different times after administration of the solution:

| | % of basal value | | | | | |
|---|---|---|---|---|---|---|
| Time (min) | 0 | 60 | 120 | 180 | 300 | 360 |
| Group 1 | 100.00 | 227.30 | 298.72 | 203.76 | 109.67 | 89.41 |
| Group 2 | 100.00 | 243.39 | 202.34 | 127.81 | 62.35 | 56.71 |
| Group 3 | 100.00 | 293.17 | 269.24 | 126.45 | 70.22 | 60.92 |

Figure 9:
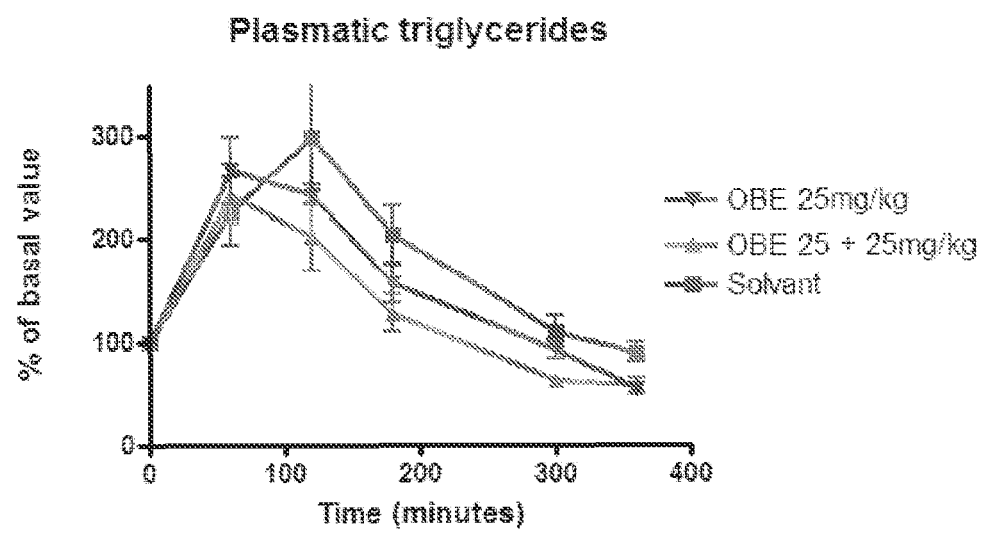
FIG. 9 is a graph illustrating the follow up in minutes of the triglycerides present in the plasma of mice having received water (solvent), one dosage of OBE2001 (OBE 25 mg/kg) or two dosages of OBE2001 (OBE 25+25 mg/kg).

Oral gavage with a solution of clinoleic at 20% led to an increase in triglycerides blood levels in all study groups the three first hours. Mice treated with OBE2001 at 25 mg/kg in group 2 and 3 show a decrease in triglyceride absorption as compared to the control group 1 (FIG. 9).

Moreover, for each group, the area under the curve was calculated according to the values of the above Table.

| Area under the curve | | % of decrease |
|---|---|---|
| Group 1 | 65453 | |
| Group 2 | 48559 | Group 2/group 1 | 26% |
| Group 3 | 56273 | Group 3/group 1 | 14% |

This calculation demonstrated that the overall triglycerides absorption is reduced by 26% in group 2 as compared to group 1, and of 14% in group 3 as compared to group 1. Consequently, these results demonstrate that OBE2001 is able to inhibit the enteropeptidase and reduces significantly the absorption of triglycerides in treated animals.

3. Effect of OBE2001 on Protein Absorption

This third in vivo experiment was designed to obtain information on the absorption of $^{14}C$-proteins in absence or in presence of OBE2001 at two different doses (5 mg/Kg or 50 mg/Kg) after an oral administration to male Swiss mice.

15 male Swiss (CD-1) mice, 5 weeks-old and having a mean body weight of 0.021±0.002 kg were divided in 3 groups:

Control Group (G1; solvant) containing 5 mice, received water at 5 mL/Kg at t-5 min and $^{14}C$-proteins at 10 mL/Kg at T=0 min;

Group 2 (G2) containing 5 mice (OBE 5 mg/Kg), received OBE2001 at 5 mg/Kg at t-5 min and $^{14}C$-proteins at 10 mL/Kg at T=0 min;

Group 3 (G3) containing $5^2$ mice (OBE 50 mg/Kg), received OBE2001 at 50 mg/Kg at t-5 min and $^{14}C$-proteins at 10 mL/Kg at T=0 min.

A preparation containing 5 ml of Clinoleic 20 (Baxter Ref DDB9500) with 1 g of glucose (Sigma; ref:G8270) and 1 g of casein (Sigma; ref: C3400) was prepared. Water was added until the solution reached 10 ml. After concentration of the radioactive solution containing the $^{14}C$ proteins (GE Healthcare; ref: CFA626) (×10), 200 μl of this radioactive solution was added to 2.8 ml of the preparation, in order to reach a concentration of ca 3.3 μCi/ml. The animals were starved before administration of this radioactive preparation.

The radioactive preparation was orally administered by intragastric gavage with a single dosing (ca 33.3 µCi/kg) in a volume of ca 10 ml/kg of body weight.

OBE2001 was provided in a mixture of two salts (HCl and TFA) with a 90% purity. OBE2001 was orally administered by intragastric gavage with a single dosing of 5 mg/Kg for G2 and 50 mg/Kg for G3 in a volume of ca 5 mL/kg body-weight.

Plasma aliquots were removed and placed into 6 ml pre-weighed plastic vials, at t+15, t+30, t+60, t+120 and t+240 min. About 4 ml Pico-fluor 40 was added and after shaking, the total radioactivity contained within the different samples was determined by liquid scintillation using a Packard 1900 CA spectrometer equipped with an external standard system (spectral analysis). A quenching curve for calibration purposes was set up using a $^{14}C$ quenched set supplied by Packard Instruments.

Liquid scintillation (LS) Counting was carried out with 2 sigma=2%, and for a maximum duration of 5 minutes (according to the method created in the 1900CA® software). Dpm (disintegration per minute) values of less than twice the background level of blank biological medium were reported as BLQ (Below the Limit of Quantitation).

Results:

During this animal experiment, no sign of morbidity or mortality occurred, and no particular effect related to dosage regimen was observed.

Figure 10:
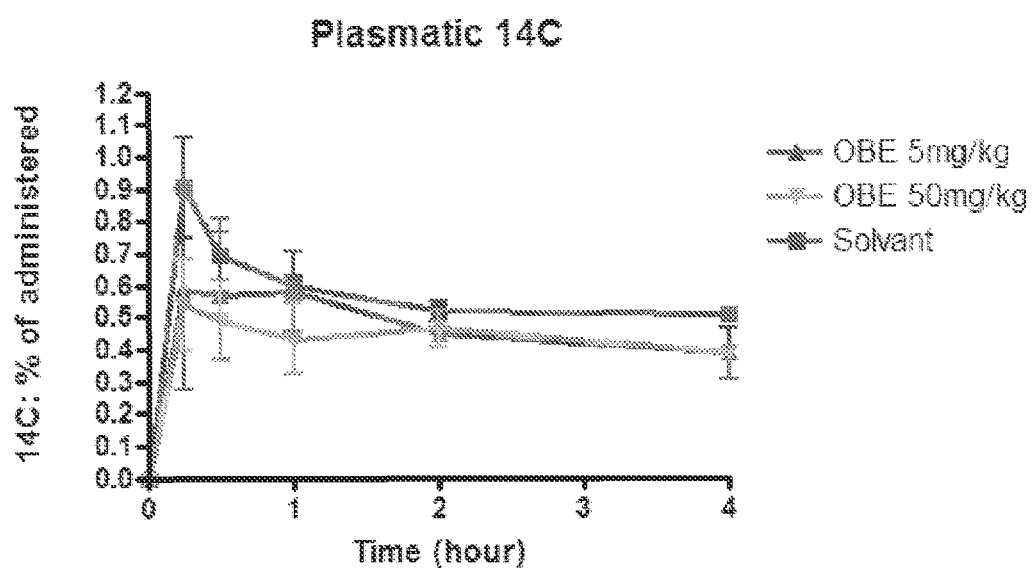
FIG. 10 is a graph illustrating the follow up in hours of labelled proteins in plasma of mice having received water (solvent), one dosage of OBE2001 (OBE 5 mg/kg) or two dosages of OBE2001 (OBE 50 mg/kg).

A Cmax of 0.9%±0.27 administered dose/g occurring at 15 min was observed for group 1 (control), while the Cmax for the treated groups tended to be lower. Indeed, for treated groups (5 mg/kg and 50 mg/kg), the Cmax were 0.58%±0.54, and 0.54%±0.24 of administered dose/g respectively. The kinetic data tended to a plateau at concentrations from 1 h to 4 h post-administration reaching respectively 0.5% administered dose/g for group 1 and 0.4% administered dose/g for groups 2 and 3 (FIG. 10).

The AUC mean for group 1 was 2.214±0.1875% dose.h.g-1. AUC mean for two others groups was respectively 1.841±0.6402% dose.h.g-1 and 1.718±0.4366% dose.h.g-1.

This result demonstrates that protein absorption is greatly decreased in mice having received OBE2001 as compared to control mice, in the first 30 minutes following protein administration, and that this decrease is maintained during at least 4 hours.

C. Generation of a Constitutive Knock Out (KO) Mice for Enteropeptidase

In order to check that enteropeptidase is a correct target protein in counteracting obesity, a knockout (KO) mouse mimicking the enteropeptidase deficiency has been produced to first validate the target and for use as an animal model for drug development.

The generation of Constitutive Knock Out mice consists of the following steps:
1. Targeting Vector Design and Construction;
2. Targeted C57BL/6 embryonic stem (ES) cells;
3. Generation of heterozygous mice for the Constitutive Knock Out;
4. Generation of homozygous mice for the Constitutive Knock Out.

1. Targeting Vector Design and Construction

The murine counterpart of human enteropeptidase is called Prss7 and is located on mouse chromosome 16.

Figure 11:
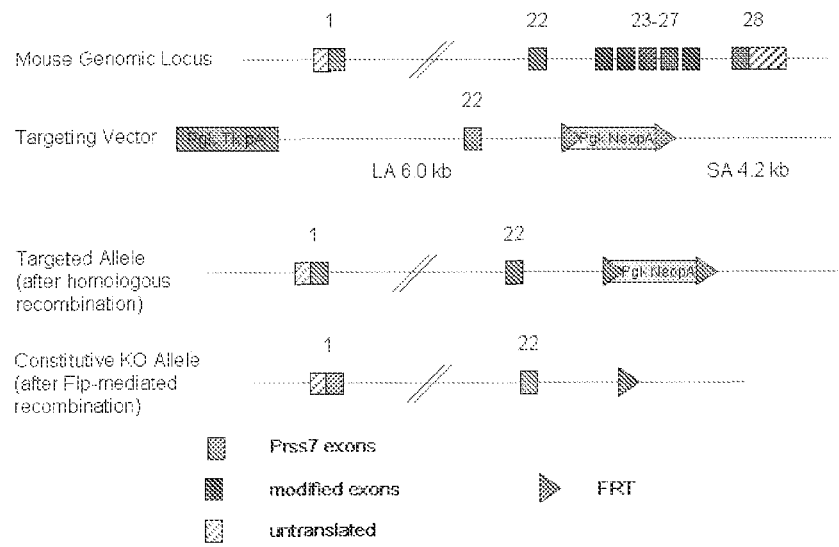
FIG. 11 is a schematic representation of the process used to obtain a constitutive enteropeptidase knockout (KO) allele in mice, using the deletion of the exons 23-28 of the Prss7 gene.

In order to inactivate the enteropeptidase gene, exons 23-28, which encode the catalytic domain, have been replaced by an FRT-flanked NeoR cassette. The constitutive KO allele (exons 1-22) encodes a C-terminally truncated protein which lacks the catalytic domain. The NeoR cassette has been excised through in vivo Flp-mediated recombination. Interference with the expression of the tail-to-tail positioned gene (Chodl) through this modification of the Prss7 gene cannot be excluded completely. The replacement of exons 23-28 (approximately 15 kb) with a FRT-Neo cassette (approximately 2 kb) decreases the efficiency of homologous recombination. A review of the KO allele construction is disclosed on FIG. 11.

Figure 12A:
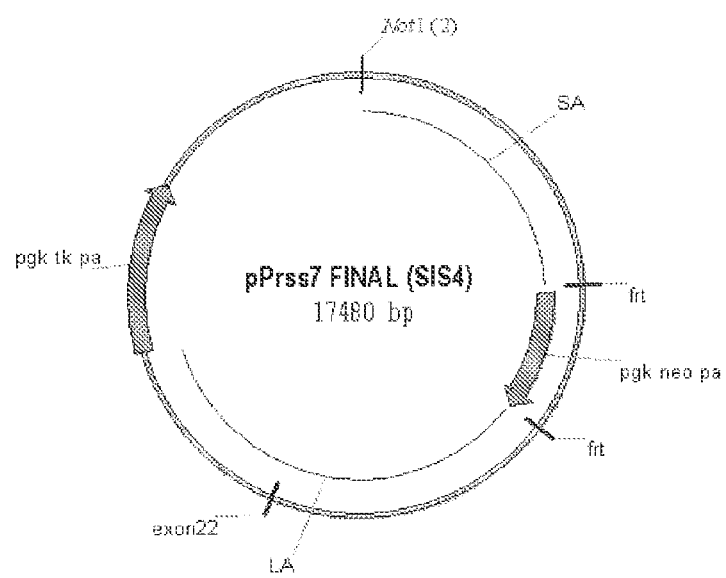
FIG. 12A is a schematic representation of a vector comprising the constitutive enteropeptidase knockout (KO) allele.

This targeting strategy allowed the construction of a vector comprising a constitutive enteropeptidase KO allele (sequence and scheme depicted in FIG. 12).

2. Targeted C57BL/6 Embryonic Stem (ES) Cells

In a second step, C57BL/6N embryonic stem (ES) cells were transfected by the vector comprising the constitutive enteropeptidase KO allele by electroporation. The transformed cells were selected for their resistance to G418 and gancyclovir. Up to 251 individual ES clones were picked and 2 positive ES clones were obtained (A-D2 and A-E8). In this step, all ES Cells (ESCs) were cultured on multi-drug resistant embryonic feeder cells without antibiotics and were regularly monitored by PCR and luminometric assays for absence of contaminating bacterias and mycoplasma. Quality control (QC) also included karyotyping (chromosome count) of all expanded ES clones and lines (for an example of a publication reporting the generation of KO mice, see Roberds et al. Human molecular Genetics, 2001, Vol 10, No 12, 1317-1324).

Before being injected into blastocysts, ES cell clones were extensively validated by Southern Blot Analysis with various probes. Therefore, genomic DNA from WT cells and A-D2 or A-E8 clones was digested with Afill, run on a gel and the transfer membrane hybridized with one of these probes, probe 5e2 (sequence: GCCGCACTATTTGCAGCATG) (FIG. 13). The deletion of exons 23-28 of Prss7 resulted in an Afill fragment of 11.7 kb (from position 5373 to position 17180) instead of the wild type (WT) allele of 18.8 kb (from position 5373 to position 24211).

Figure 14:
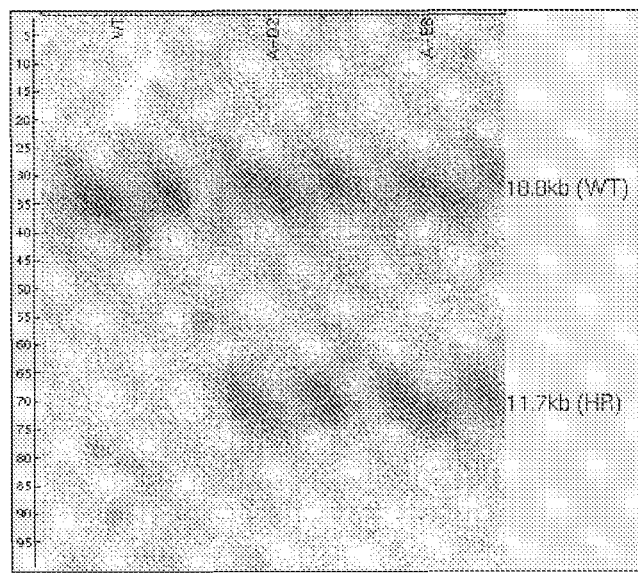
FIG. 14 is a Southern Blot obtained with genomic DNA from embryonic stem (ES) cells successfully transformed with the enteropeptidase KO allele (A-D2 and A-E8) and obtained with the genomic DNA of non transformed cells (WT).

As shown in FIG. 14, AD-2 and A-E8 clones have a wild type allele (18.8 kb) as well as a KO allele (11.7 kb). In contrast, wild type (WT) cells have two WT (non deleted) alleles (18.8 kb).

These results confirm that the AD-2 and A-E8 clones have successfully incorporated the KO allele.

3. Generation of Heterozygous Mice for the Constitutive Knock Out

In a third step, 2 ES cell clones were injected into diploid host blastocysts, and the injected blastocyst transferred in pseudopregnant recipients (microoperation under specific pathogen free (SPF) conditions). Therefore, heterozygote (>50%) coat color chimeras were generated and breeded to heterozygosity.

To control the success of this third step, offspring were genotyped by the following PCR protocol. Genomic DNA, extracted from mouse tail, was amplified simultaneously with a first set of primers (primer 1472_23 with sequence: CGTTACTATCCATCACCTAAGC and primer 1472_24 with sequence GGGAATTCAGCTGTGTCTGAAC) corresponding to the enteropeptidase KO allele, and a second set of primers (primer 1260_1: GAGACTCTGGCTACTCATCC and primer 1260_2: CCTTCAGCAAGAGCTGGGGAC) corresponding to an internal control. The size of the enteropeptidase KO allele was 412 bp (cony), and the size of the internal control was 585 bp (c).

Figure 15:
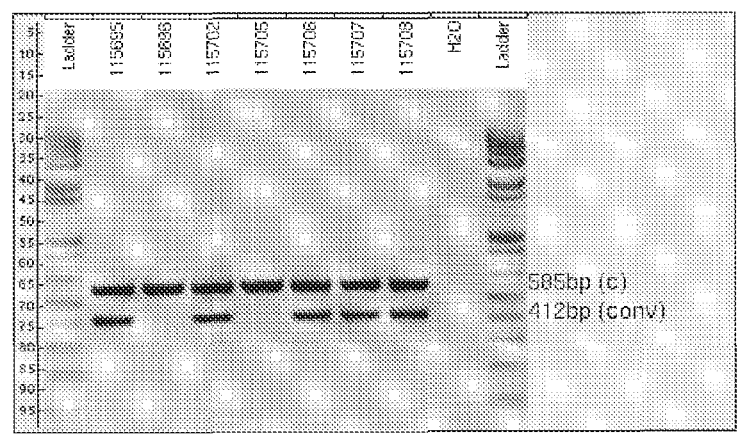
FIG. 15 is a blot in which PCR fragments have been run, from a simultaneous amplification with primers 1260_1 and 1260_2, and 1472_23 and 1472_24. Genomic DNA has been extracted from heterologous mice (115695, 115702, 115706, 115707 and 115708) or wild type mice (115696 or 115705). 585 bp (c): control fragment; 412 bp (cony): KO allele.

As expected, the amplification of genomic DNA from WT mice (115696 and 115705) gave a unique band at 585 bp. In contrast, the amplification of genomic DNA from heterozygous mice (115695, 115702, 115706, 115707 and 115708) gave two bands, one for the control allele (585 bp) and one for the KO allele (412 bp) (FIG. 15).

4. Generation of Homozygote Pups for Enteropeptidase

In a last step, homozygote pups for enteropeptidase KO were generated.

Enteropeptidase KO heterozygotes were crossed and 46 pups were obtained. Among the newborns, 30% (14 pups) were homozygote for the enteropeptidase KO, 50% were heterozygotes (22 pups) and 20% were wild type (homozygote dominant for the enteropeptidase gene).

The presence of the KO enteropeptidase in a homozygous strain was checked by PCR analysis, from genomic DNA, extracted from mouse tail. Genomic DNA was simultaneously amplified with a first set of primers (primer 1472_23 with sequence: CGTTACTATCCATCACCTAAGC and primer PRRS7 with sequence ATCAAGGAATCTTGGGAGCA) corresponding to the WT enteropeptidase allele, and a second set of primers (actin forward primer: CGGAACCGCYCATTGGC and actin backward primer: ACCCACACTGTGCCCATCTA) corresponding to the actin control. The size of the enteropeptidase allele was 533 bp, and the size of the actin control was 300 bp.

Figure 16:
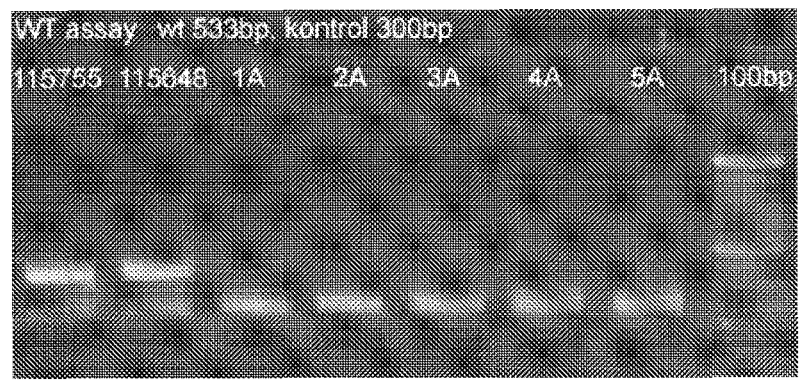
FIG. 16 is a blot in which PCR fragments, obtained from a simultaneous amplification with primer 1472_23 and primer PRRS7 WT, and beta actin forward and beta actin backward primers, have been run. Genomic DNA has been extracted from heterologous mice (115755 and 115648) or KO homologous pups (1A, 2A, 3A, 4A and 5A); 533 bp (c): WT enteropeptidase allele; 300 bp: control allele (actin).

As can be seen from FIG. 16, the amplified fragments from heterozygous mice, in lanes named 115755 and 115648, present two bands, one corresponding to the actin control (300 bp) and one to the WT enteropeptidase allele (533 bp). In contrast, fragments amplified from newborns 1A, 2A, 3A, 4A and 5A has a size of 300 bp and thus correspond to the sole actin control, demonstrating that they lack a WT enteropeptidase allele.

5. Phenotypic Observations

Newborns, obtained from the crossing of enteropeptidase knockout (KO) heterozygotes, were grown during 7 days and their size compared.

Figure 17:
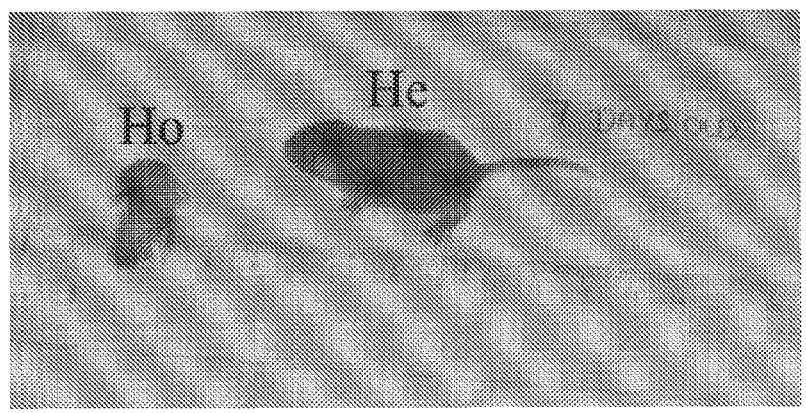
FIG. 17 is a photograph showing a mouse homozygous for the enteropeptidase knockout allele (Ho) and a mouse heterozygous for the enteropeptidase knockout allele (He), both 7 days old.

As can be shown in FIG. 17, the mouse homozygous for the enteropeptidase KO (Ho) is twice smaller than the mouse heterozygous for the enteropeptidase KO (He).

These results demonstrated that enteropeptidase is a good target to fight obesity, since its complete specific inhibition results in a significant size decrease.

---

What is claimed is:

1. A method of treating a mammal having obesity or excessive weight, or a mammal suffering from abnormal fat metabolism disease selected from type II diabetes and hypertriglyceridemia, comprising the step of administering to said mammal at least one compound which inhibits the enzymatic activity of an enteropeptidase, wherein the compound is selected from the group consisting of: Glu-Gly-BoroArg, Ala-Phe-BoroArg, Glu-Gly-BoroLys, Ala-Phe-BoroLys, Ac-Glu-Gly-BoroArg, Ac-Ala-Phe-BoroArg, Ac-Glu-Gly-BoroLys, and Ac-Ala-Phe-BoroLys, wherein Ac is acetyl, Glu is glutamic acid, Gly is glycine, Ala is alanine, Phe is phenylalanine, BoroArg is boro-arginine, and BoroLys is borolysine; the BoroArg or BoroLys moieties having a functional group of selected from the group consisting of:

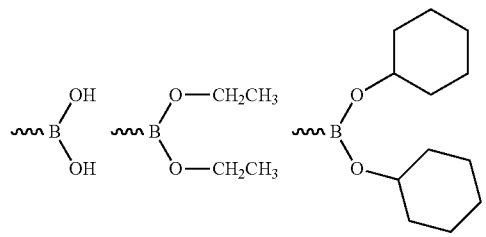

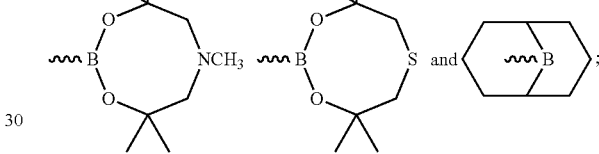

wherein the compound is non-absorbable, and selectively inhibits the enzymatic activity of an enteropeptidase localized in the intestine over other, systemically localized serine proteases.

2. The method of claim 1, wherein the BoroArg or BoroLys moieties have a group of the formula:

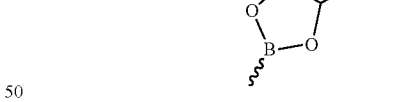

3. The method of claim 1, wherein the compound is selected from the group consisting of:

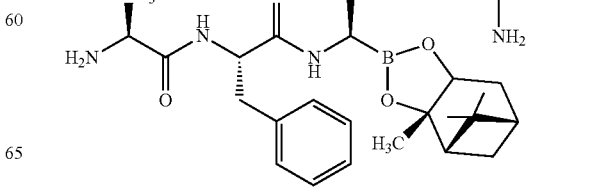

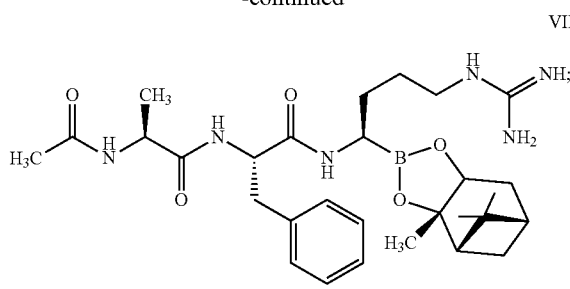

VIII

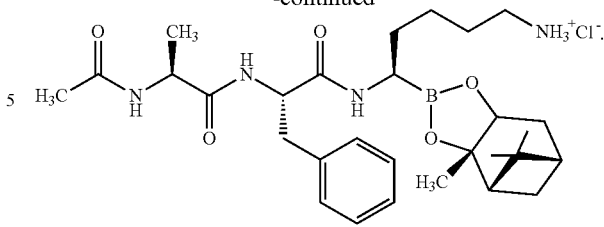

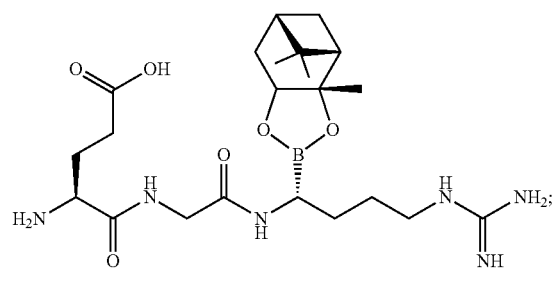

IX

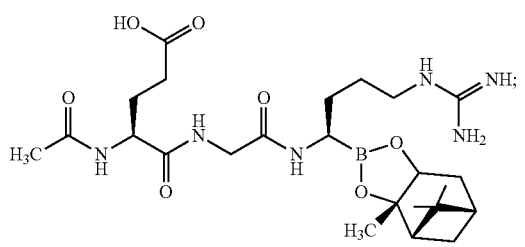

X and

4. The method of claim 1, wherein the compound is in a free base form or is a pharmaceutically acceptable salt thereof.

5. The method of claim 1, wherein the Glu, Gly, Ala and Phe amino acid is each an (L)-amino acid.

6. The method of claim 1, wherein the compound is administered in a pharmaceutical composition further comprising a pharmaceutically acceptable carrier, wherein the composition is formulated for oral or enteral administration.

7. The method according to claim 1, wherein the compound is administered in combination with at least one other drug.

8. The method of claim 1, wherein the mammal is a human.

9. The method of claim 1, wherein the obesity results from environmental causes, from genetic alterations, from medical illness, from smoking cessation, from medications or from neurological disorders.

\* \* \* \* \*